US010869877B2

(12) United States Patent
Lukas et al.

(10) Patent No.: US 10,869,877 B2
(45) Date of Patent: *Dec. 22, 2020

(54) CONTROLLED RELEASE DOXYCYCLINE

(71) Applicant: Mayne Pharma International Pty Ltd., Salisbury South (AU)

(72) Inventors: Stefan Lukas, Manningham (AU); Angelo Lepore, Rostrevor (AU); Stuart Mudge, Northcote (AU)

(73) Assignee: Mayne Pharma International Pty. Ltd., Salisbury South (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,410

(22) Filed: Mar. 8, 2019

(65) Prior Publication Data

US 2019/0201421 A1 Jul. 4, 2019

Related U.S. Application Data

(63) Continuation of application No. 15/369,252, filed on Dec. 5, 2016, now abandoned, which is a continuation-in-part of application No. 14/973,149, filed on Dec. 17, 2015, now Pat. No. 9,511,031, which is a continuation-in-part of application No. 14/521,998, filed on Oct. 23, 2014, now Pat. No. 9,295,652.

(60) Provisional application No. 62/061,481, filed on Oct. 8, 2014.

(51) Int. Cl.
| | | |
|---|---|---|
| *A61K 9/28* | (2006.01) | |
| *A61K 31/65* | (2006.01) | |
| *A61K 9/50* | (2006.01) | |
| *A61K 9/20* | (2006.01) | |

(52) U.S. Cl.
CPC ............ *A61K 31/65* (2013.01); *A61K 9/2054* (2013.01); *A61K 9/2081* (2013.01); *A61K 9/5042* (2013.01); *A61K 9/5047* (2013.01)

(58) Field of Classification Search
CPC ...... A61K 9/16; A61K 9/1605; A61K 9/1611; A61K 9/1652; A61K 9/20; A61K 9/2004; A61K 9/2009; A61K 9/2013; A61K 9/2054; A61K 9/28; A61K 9/2806; A61K 9/2866; A61K 9/286; A61K 9/2886
See application file for complete search history.

(56) References Cited

U.S. PATENT DOCUMENTS

| | | |
|---|---|---|
| 2,196,768 A | 4/1940 | Hiatt |
| 3,141,792 A | 7/1964 | Lachman et al. |
| 4,347,235 A | 8/1982 | Daunora |
| 4,684,516 A | 8/1987 | Bhutani |
| 4,837,030 A | 6/1989 | Valorose, Jr. et al. |
| 4,966,770 A | 10/1990 | Giannini et al. |
| 5,009,897 A | 4/1991 | Brinker et al. |
| 5,068,110 A | 11/1991 | Fawzi et al. |
| 5,167,964 A | 12/1992 | Muhammad et al. |
| 5,169,642 A | 12/1992 | Brinker et al. |
| 5,188,836 A | 2/1993 | Muhammad et al. |
| 5,225,202 A | 7/1993 | Hodges et al. |
| 5,268,182 A | 12/1993 | Brinker et al. |
| 5,288,501 A | 2/1994 | Nurnberg et al. |
| 5,413,777 A | 5/1995 | Sheth et al. |
| 5,468,286 A | 11/1995 | Wai-Chiu et al. |
| 5,508,276 A | 4/1996 | Anderson et al. |
| 5,817,338 A | 10/1998 | Bergstrand et al. |
| 5,855,914 A | 1/1999 | Koyama et al. |
| 6,054,145 A | 4/2000 | Vromans et al. |
| 6,136,344 A | 10/2000 | Depui et al. |
| 6,224,911 B1 | 5/2001 | Chowhan et al. |
| 6,346,269 B1 | 2/2002 | Hsiao et al. |
| 6,475,521 B1 | 11/2002 | Timmins et al. |
| 6,669,879 B1 | 12/2003 | Spengler et al. |
| 6,723,348 B2 | 4/2004 | Faham et al. |
| 6,958,161 B2 | 10/2005 | Hayes et al. |
| 7,232,572 B2 | 6/2007 | Ashley |
| 7,910,128 B2 | 3/2011 | Chang et al. |
| 8,470,364 B2 | 6/2013 | Chang et al. |
| 8,603,506 B2 | 12/2013 | Ashley |
| 8,652,516 B1 | 2/2014 | Etchegaray et al. |
| 8,715,724 B2 | 5/2014 | Lukas |
| 9,295,652 B1 | 3/2016 | Lukas et al. |
| 9,446,057 B2 | 9/2016 | Lukas et al. |
| 9,511,031 B2 | 12/2016 | Lukas et al. |
| 2002/0015731 A1 | 2/2002 | Appel et al. |
| 2003/0099700 A1 | 5/2003 | Faham et al. |
| 2004/0142035 A1 | 7/2004 | Chang et al. |

(Continued)

FOREIGN PATENT DOCUMENTS

| | | | |
|---|---|---|---|
| EP | 0502642 A1 | 9/1992 | |
| EP | 0609661 A1 * | 8/1994 | ............... B24C 3/26 |

(Continued)

OTHER PUBLICATIONS

NDA Application # 50-795 Clinical Pharmacology and Biopharmaeuctics Review (Year: 2005).*
NDA Application No. 50-795 (Clinical Pharmacology and Biophrmeutics Review 2005) (Year: 2005).*
NDA Application No. 50-795 (Clinical Pharmacology and Biopharmeutics Review, 2005) (Year: 2005).*
Robinson, J., and V.H. Lee, "Controlled Drug Delivery: Fundamentals and Applications," from "Drugs and the Pharmaceutical Sciences," Marcel Dekker, Inc., NY, 1987, pp. 293-334, 44 pages.
Saivin, S., and G. Houin, "Clinical Pharmacokinetics of Doxycycline and Minocycline," Clinical Pharmacokinetics 15(6):355-366, 1988.
Solodyn (minocycline HCI, USP), extended release tablets, Center for Drug Evaluation and Research (2006), NDA No. 50-808, Labeling and Patient Information, Manufactured for: Medicis, The Dermatology Company, Scottsdale, AZ, By: AAIPharma Inc., Wilmington, NC, 30 pages.

(Continued)

*Primary Examiner* — Micah Paul Young
(74) *Attorney, Agent, or Firm* — Christensen O'Connor Johnson Kindness PLLC

(57) ABSTRACT

The disclosure provides controlled release compositions comprising tetracyclines and in some embodiments, doxycycline. The controlled release doxycycline compositions of the invention exhibit a superior dissolution profile and provide reduced side effects such as nausea and irritation.

25 Claims, 17 Drawing Sheets

(56) References Cited

U.S. PATENT DOCUMENTS

| | | | |
|---|---|---|---|
| 2004/0228912 A1* | 11/2004 | Chang | A61K 31/65 424/464 |
| 2005/0053654 A1 | 3/2005 | Faham et al. | |
| 2005/0164993 A1 | 7/2005 | Ashley | |
| 2006/0252731 A1 | 11/2006 | Pfeiffer et al. | |
| 2009/0136568 A1 | 5/2009 | Lukas | |
| 2010/0330180 A1 | 12/2010 | Lukas | |
| 2012/0100214 A1 | 4/2012 | Segura et al. | |
| 2014/0274970 A1 | 9/2014 | Chandran et al. | |
| 2015/0098995 A1 | 4/2015 | Lukas | |
| 2016/0101052 A1 | 4/2016 | Lukas et al. | |
| 2016/0101060 A1 | 4/2016 | Lukas et al. | |
| 2016/0101119 A1 | 4/2016 | Lukas et al. | |
| 2016/0263129 A1 | 9/2016 | Lukas et al. | |

FOREIGN PATENT DOCUMENTS

| | | | | |
|---|---|---|---|---|
| EP | 0609961 A1 * | 8/1994 | | A61K 31/485 |
| EP | 0609961 A1 | 8/1994 | | |
| EP | 0630646 A1 | 12/1994 | | |
| EP | 0609961 B1 | 6/1998 | | |
| WO | 2006/045152 A1 | 5/2006 | | |

OTHER PUBLICATIONS

Story, M.J., et al., "Doxycycline Tolerance Study: Incidence of Nausea After doxycycline Administration to Healthy Volunteers: A Comparison of 2 Formulations (Doryx' vs Vibramycin')," European Journal of Clinical Pharmacology 40(4):419-421, 1991.

Teng, Y., and Z. Qiu, "Fluid Bed Coating and Granulation for CR Delivery," in Fl Wen et al. (eds.), "Oral Controlled Release Formulation Design and Drug Delivery: Drug to Practice," John Wiley & Sons, Hoboken, N.J., 2010, 121, 13 pages.

The United States Pharmacopeia National Formulary (2000), USP 24, NF 19, Doxycycline / Official Monographs, pp. 609-612, 6 pages.

The United States Pharmacopeia National Formulary Supplement (1998), USP 23, Supplement 8, NF 18, pp. 4281-4446, 168 pages.

Whelton, A., et al., "Doxycycline Pharmacokinetics in the Absence of Renal Function," Kidney International 5(5):365-371, 1974.

Wollina, U., "Rosacea and Rhinophyma in the Elderly," Clinics in Dermatology 29(1):61-68, 2011.

Basak, S.C., et al., "Doxycycline Hyclate Delayed Release Capsules With Sodium Starch Glycolate," Indian Journal of Pharmaceutical Sciences 66(5):704-707, 2004.

Berger, R.S., "A Double-Blind, Multiple-Dose, Placebo-Controlled, Cross-Over Study to Compare the Incidence of Gastrointestinal Complaints in Healthy Subjects Given Doryx Rand Vibramycin R," Journal of Clinical Pharmacology 28(4):367-370, 1988.

Bodmeier, R., "Tableting of Coated Pellets," European Journal of Pharmaceutics and Biopharmaceutics 43:1-8, 1996.

Bravo, S.A., et al., "In-vitro studies of diclofenac sodium controlled-release from biopolymeric hydrophilic matrices," Journal of Pharmacy & Pharmaceutical Science 5(3):213-219, 2002. (see in particular "Materials and Methods," "Preparation and Characterization of Matrix Tablets," and "Results and Discussion" "Physical characterization of the matrix tablets".).

Cabot Corporation, "Applications of CAB-O-SIL® M-5P Fumed Silica in the Formulation and Design of Solid Dosage Forms," 2004, see in particular the Summary, 5 pages.

Cabot Corporation, "Influence of CAB-O-SIL® M-5P on the Angle of Repose and Flow Rates of Pharmaceutical Powders," 2004, see in particular the second paragraph in passage entitled "Background," 10 pages.

Cabot Corporation, "Properties of CAB-O-SIL® M-5P Fumed Silica," 2004, see in particular the passage entitled "Flow Properties," 6 pages.

Cunha, B.A., et al., "Doxycycline," Therapeutic Drug Monitoring 4(2):115-135, 1982.

Del Rosso, J.Q., "Systemic Therapy for Rosacea: Focus on Oral Antibiotic Therapy and Safety," Cutis 66(4 Suppl):7-13, 2000.

Dey, S., et al., "Multiparticulate Drug Delivery Systems for Controlled Release," Tropical Journal of Pharmaceutical Research 7(3):1067-1075, 2008.

Federal Register 21446-21453, vol. 65, No. 78, Apr. 21, 2000, 8 pages.

Hill, P.M., "Effect of Compression Force and Corn Starch on Tablet Disintegration Time," Journal of Pharmaceutical Sciences 65(11):1694-1697, 1976.

Jantratid, E., et al., "Biowaiver Monographs for Immediate Release Solid Oral Dosage Forms: Doxycycline Hyclate," Journal of Pharmaceutical Sciences 99(4):1639-1653, 2010.

Järvinen, A., et al., "Enteric Coating Reduces Upper Gastrointestinal Adverse Reactions to Doxycycline," Clinical Drug Investigations 10(6):323-327, 1995.

Jones, T.M., "The effect of glidant addition on the flowability of bulk particulate solids," Journal of the Society of Cosmetic Chemists 21(7):483-500, 1970; see in particular Table III on pp. 488-489, and p. 496.

Kalin, M., et al., "Three Cases of Canine Leptospirosis in Quebec," Canadian Veterinary Journal 40(3):187-191, 1999.

Katsambas, A.D., et al., "Guidelines for Treating Acne," Clinics in Dermatology 22:439-444, 2004.

Kircik, L.H., and J.B. Bikowski, "Optimizing Outcomes and Enhancing Adherence Through Formulation Advancements," Vehicles Matter, Supplement to Practical Dermatology, 2010), <bmctoday.net/vehiclesmatter/pdfs/1210.pdf>, 16 pages.

Kokubo, H., et al., "Development of Cellulose Derivatives as Novel Enteric Coating Agents Soluble at pH 3.5-4.5 and Higher," Chemical & Pharmaceutical Bulletin 45(8):1350-1353, Aug. 1997.

Kommanaboyina, B., and C.T. Rhodes, "Trends in Stability Testing, With Emphasis on Stability During Distribution and Storage," Drug Development and Industrial Pharmacy 25(7):857-868, 1999.

Maibach, H., "Second-Generation Tetracyclines, A Dermatologic Overview: Clinical Uses and Pharmacology," Cutis 48(5):411-417, 1991.

Muhammad, N.A., et al., "Evaluation of Hydroxypropyl Methylcellulose Phthalate 50 as Film Forming Polymer From Aqueous Dispersion Systems," Drug Development and Industrial Pharmacy 18(16)1787-1797, 1992.

Murthy, K.S., and I. Ghebre-Sellassie, "Current Perspectives on the Dissolution Stability of Solid Oral Dosage Forms," Journal of Pharmaceutical Sciences 82(2):113-126, 1993.

NDA#50-795 (Year:2005).

Nelson, M.L, and S.B. Levy, "The History of Tetracyclines," Annals of the New York Academy of Science 1241:17-32, 2011.

NDA Application #50-795, Coated doxycycline hyclate pellets (Doryx®), DORYX Tablets 100 mg and DORYX Capsules 100 mg, Clinical Pharmacology and Biopharmaceutics Review(s), Center for Drug Evaluation and Research, Submission Dates: Apr. 5, 2004; Nov. 23, 2004; Dec. 10, 2004; Dec. 14 draft, 2004; Dec. 17, 2004; Dec. 20, 2004; Jan. 11, 2005; Feb. 18, 2005; Mar. 10, 2005, 28 pages.

ORACEA (doxycycline, USP), 40 mg (30 mg Immediate Release & 10 mg Delayed Release beads), Center for Drug Evaluation and Research (2006), NDA No. 50-805, Labeling and Patient Information, Collagenex Pharmaceuticals, Inc., Newton, PA 18940, USA, 20 pages.

PCT/AU2005/001663, International Preliminary Report on Patentability dated Dec. 5, 2006, 12 pages.

PCT/AU2005/001663, International Search Report and Written Opinion dated Feb. 8, 2006, 9 pages.

Pharmaceutical Dosage Forms, Tablets, 2nd Edition, 1989, vol. 1, Edited by Herbert A Lieberman et al., Marcel Dekker, Inc., New York, USA. (See in particular Chapter 1 Preformulation Testing, Wadke, DA et al., p. 55 last 4 lines to p. 56 line 2, Chapter 2 Tablet Formulation and Design, Peck, G.E. et al., pp. 110-116 and Chapter 3, Compressed Tablets by Wet Granulation, Sandelin, F.J., pp. 169-179), 29 pages.

Pharmaceutical Dosage Forms, Tablets, 2nd Edition, 1990, vol. 2, Edited by Herbert A. Lieberman et al., Marcel Dekker, Inc., New

(56) References Cited

OTHER PUBLICATIONS

York, USA. (See in particular Chapter 5 Granulation Technology and Tablet Characterization, Gordon, RE. et al., pp. 295-298 and pp. 306-308), 13 pages.
Physicians' Desk Reference: Edition 28, pp. 942-943 (1974), 4 pages.
Physicians' Desk Reference: Edition 54, pp. 944-946 (2000), 4 pages.
Physicians' Desk Reference: Edition 54, pp. 2082-2083; 2384-2086 (2000), 8 pages.
Physicians' Desk Reference: Edition 61, pp. 1000-1002 (2007), 4 pages.
Revised Apr. 2013; NDA #050795, DORYX® (doxycycline hyclate delayed-release tablets), 80 mg, 100 mg, 150 mg, and 200 mg for Oral use. Initial U.S. Approval: 1967. <https://www.accessdata.fda.gov/scripts/cder/daf/index.cfm?event=overview.orocess&Ao o1No=050795>.
Revised Apr. 2016; NDA #050795, Doxycycline Hyclate Delayed-Release Tablets Oral use; 75 mg, 100 mg, 150 mg and 200 mg. Initial U.S. Approval: 1967. <https://www.accessdata.fda.gov/scripts/cder/daf/index.cfm?event=overview.process&ApplNo=050795>.
Revised May 2015; NDA #050795, DORYX® (doxycycline hyclate delayed-release tablets) Oral use; 100 mg, 150 mg, and 200 mg. Initial U.S. Approval: 1967. <https://www.accessdata.fda.gov/scripts/cder/daf/index.cfm?event=overview.process&ApplNo=050795>.
Revised May 2016; NDA #050795, DORYX MPG (doxycycline hyclate delayed-release tablets), for oral use; 60 mg, 120 mg. Initial U.S. Approval: 1967. <https://www.accessdata.fda.gov/scripts/cder/daf/index.cfm?event=overview.process&ApplNo=050795>.
Revised May 2017: NDA #050795, DORYX MPG (doxycycline hyclate delayed-release tablets), 60 mg, 120 mg. <https://www.accessdata.fda.gov/scripts/cder/daf/index.cfm?event=overview.process&ApplNo=050795>.
Revised Sep. 2011; NDA #050795, DORYX® (Doxycycline Hyclate Delayed-Release Tablets, USP), 75 mg, 100 mg and 150 mg for Oral use. Initial U.S. Approval: 1967. <https://www.accessdata.fda.gov/scripts/cder/daf/index.cfm?event=overview.process&ApplNo=050795>.
Revised Sep. 2011; NDA #050795/S-013, DORYX® (Doxycycline Hyclate Delayed-Release Tablets, USP), 75 mg, 100 mg and 150 mg for Oral use. Initial U.S. Approval:1967; FDA Approved Mar. 21, 2011; <https://www.accessdata.fda.gov/drugsatfda.docs/label/2011/050795s0131bl.pdf>.
Revised Aug. 2015; NDA #050582, DORYX® (doxycycline hyclate) Delayed-Release Capsules, 75 mg and 100 mg. Obtained from <https://www.accessdata.fda.gov/drugsatfda_docs/label/2015/050582s0291bl.pdf>.
Revised Dec. 2006; NDA #050795, DORYX® (doxycycline hyclate) Delayed-Release Tablets, 75 mg and 100 mg. <https://www.accessdata.fda.gov/scripts/cder/daf/index.cfm?event=overview.process&ApplNo=050795>.
Revised Jun. 2008; NDA #050795, DORYX® (doxycycline hyclate) Delayed-Release Tablets, 75 mg, 100 mg and 150 mg for Oral use. <https://www.accessdata.fda.gov/scripts/cder/daf/index.cfm?event=overview.process&ApplNo=050795>.
Revised Mar. 2007; NDA #050582, Doryx (doxycycline hyclate) Capsule, Delayed Release Pellets. Mayne Pharma International Pty Ltd (2007); 17 pages.
Revised Mar. 2007; NDA #050795, Doryx (doxycycline hyclate) Capsule, Delayed Release Pellets. Mayne Pharma International Pty Ltd (2007); 13 pages.
Revised May 2005; NDA #050582, DORYX® (doxycycline hyclate) Delayed-Release Capsules, 75 mg and 100 mg. Obtained from <https://www.accessdata.fda.gov/drugsatfda_docs/label/2005/050582s0241bl.pdf>.
Revised May 2005; NDA #050795, DORYX® (doxycycline hyclate) Delayed-Release Tablets, 75 mg and 100 mg. <https://www.accessdata.fda.gov/scripts/cder/daf/index.cfm?event=overview.process&ApplNo=050795>.

\* cited by examiner

CONTROLLED RELEASE DOXYCYCLINE

CROSS-REFERENCES TO RELATED APPLICATION(S)

The present Application is a continuation of U.S. application Ser. No. 15/369,252, filed on Dec. 5, 2016, which is itself a continuation-in-part of U.S. application Ser. No. 14/973,149, filed on Dec. 17, 2015, and that issued as U.S. Pat. No. 9,511,031 on Dec. 6, 2016, which is itself a continuation-in-part of U.S. application Ser. No. 14/521,998, filed on Oct. 23, 2014, and that issued as U.S. Pat. No. 9,295,652 on Mar. 29, 2016, and which claims priority to U.S. Provisional Application No. 62/061,481, filed on Oct. 8, 2014, the entire contents of each of which are hereby incorporated by reference in their entirety.

FIELD

The present disclosure relates to the field of pharmaceutical compositions comprising tetracyclines. In specific aspects, the disclosure provides pharmaceutical compositions comprising doxycycline that have improved controlled release characteristics.

BACKGROUND

Tetracyclines, such as doxycycline, are used as broad spectrum antibiotics to treat various bacterial infections. Tetracyclines interfere with the protein synthesis of Gram positive and Gram-negative bacteria by preventing the binding of aminoacyl-tRNA to the ribosome. Their action is bacteriostatic (preventing growth of bacteria) rather than killing (bactericidal). The doses commonly used for doxycycline to achieve the antibiotic effect are 100 mg and 50 mg.

Doxycycline, as well as other tetracyclines, has other therapeutic uses in addition to its antibiotic properties. For example, doxycycline is known to inhibit the activity of collagen destruction enzymes such as collagenase, gelatinase, and elastase. Its collagenase inhibition activity has been used to treat periodontal disease.

Doxycycline can also inhibit lipase produced by the bacterium *Propionibacterium acnes* and thus reduces the availability of free fatty acids that are involved in inflammation. Doxycycline may also reduce inflammation by reducing cytokine levels so that the integrity of the follicular wall is preserved. Thus, doxycycline has the potential in treating skin diseases, such as acne.

While tetracyclines have proven to be very beneficial and successful antibiotics, this class of compounds suffers from a major drawback associated with administration. Namely, tetracycline antibiotics cause an undesirable degree of gastrointestinal irritation and nausea in subjects taking the medications.

The nausea associated with administration of many tetracyclic antibiotics results from the release of the tetracycline into the lumen of an individual's stomach after ingestion. Since many tetracycline antibiotics are formulated as immediate release tablets, such antibiotic formulations begin to release antibiotic immediately upon administration and release high concentrations of tetracycline upon entering the acidic environment of a patient's stomach. The high localized concentration of the antibiotic in the patient's stomach leads to irritation and nausea.

There have been attempts to provide delayed or extended release pharmaceutical formulations of tetracyclic antibiotics that do not release in an individual's stomach, but rather release in the colon. However, many of these formulations suffer from inadequate dissolution profiles that do not provide an effective dose of antibiotic at the desired concentration and for the desired period of release.

Thus, there is a great need in the art for the development of improved controlled release pharmaceutical formulations of tetracyclic antibiotics.

More particularly, there is a need in the art for controlled release doxycycline antibiotic formulations that provide clinically effective doses of doxycycline with reduced stomach irritation and nausea.

BRIEF SUMMARY

The present disclosure addresses a crucial need in the art, by providing a controlled release pharmaceutical formulation comprising doxycycline. The controlled release doxycycline formulations of the present invention exhibit less than about 10% release of doxycycline at pH levels found in the stomach (e.g., at a pH of about 1.2) when measured after 1 hour under USP <711> conditions, and maintain low release levels at pH values up to 4.5, but have release rates at pH 5 (as disclosed herein) that enable a clinically effective plasma level to be achieved.

The dissolution or release profile of the doxycycline formulations of the present invention is superior to the release profiles of other doxycycline formulations presently in the art. The advantages associated with the disclosure's release profile include, inter alia: increased efficacy of the antibiotic, increased tolerability, and ultimately increased patient compliance with drug administration.

Figure 8:
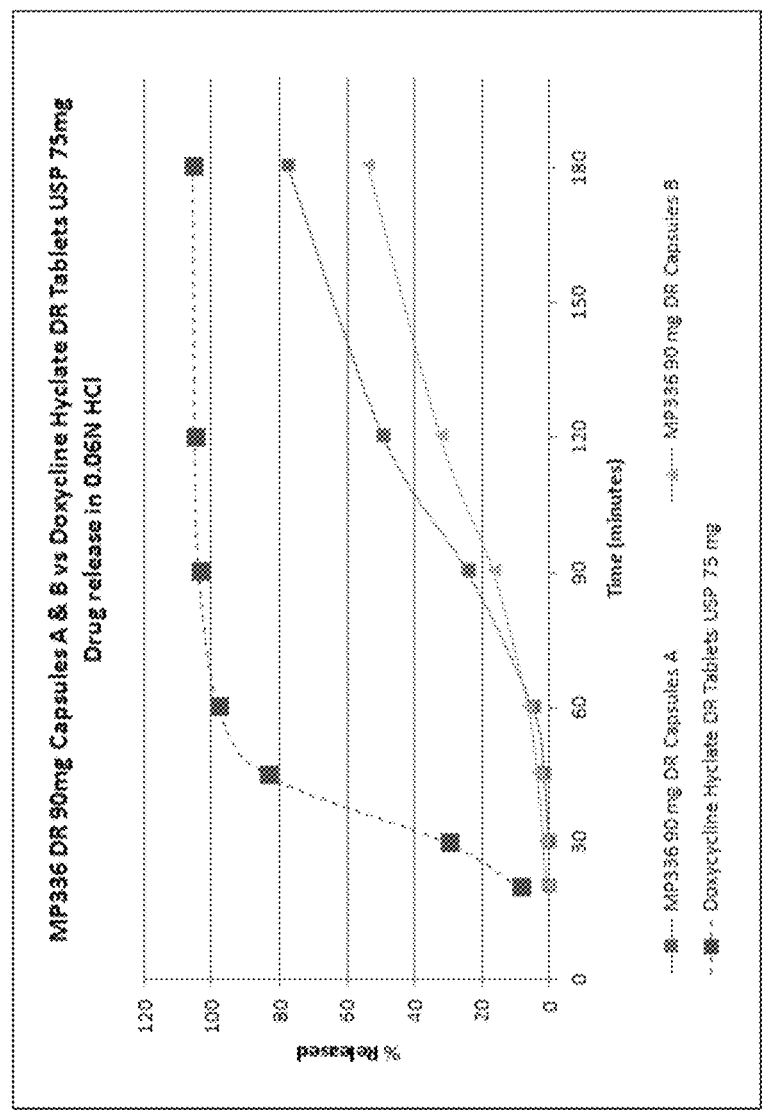

FIG. 8 is a graph illustrating the dissolution profile in 0.06N HCl of controlled release pellet formulation (A or B, 90 mg doxycycline) of the disclosure compared to a control 75 mg DORYX tablet.

Figure 9:
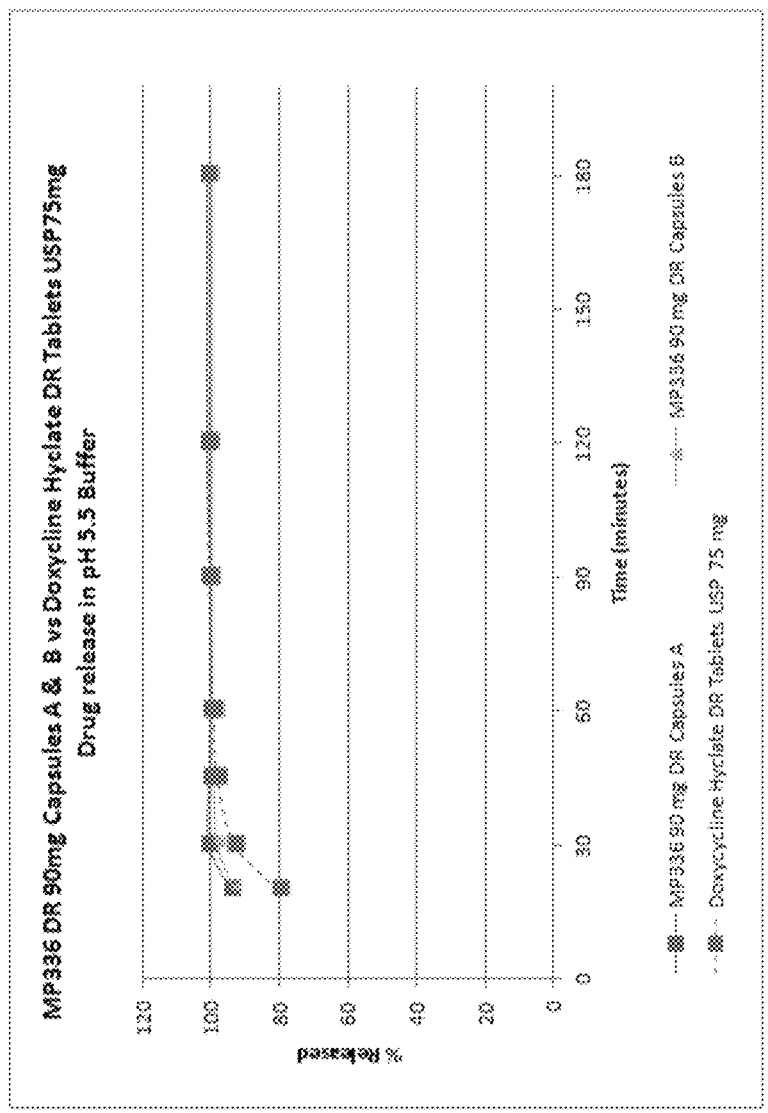

FIG. 9 is a graph illustrating the dissolution profile at pH 5.5 of a controlled release pellet formulation (A or B, 90 mg doxycycline) of the disclosure compared to a control 75 mg DORYX tablet.

Figure 10:
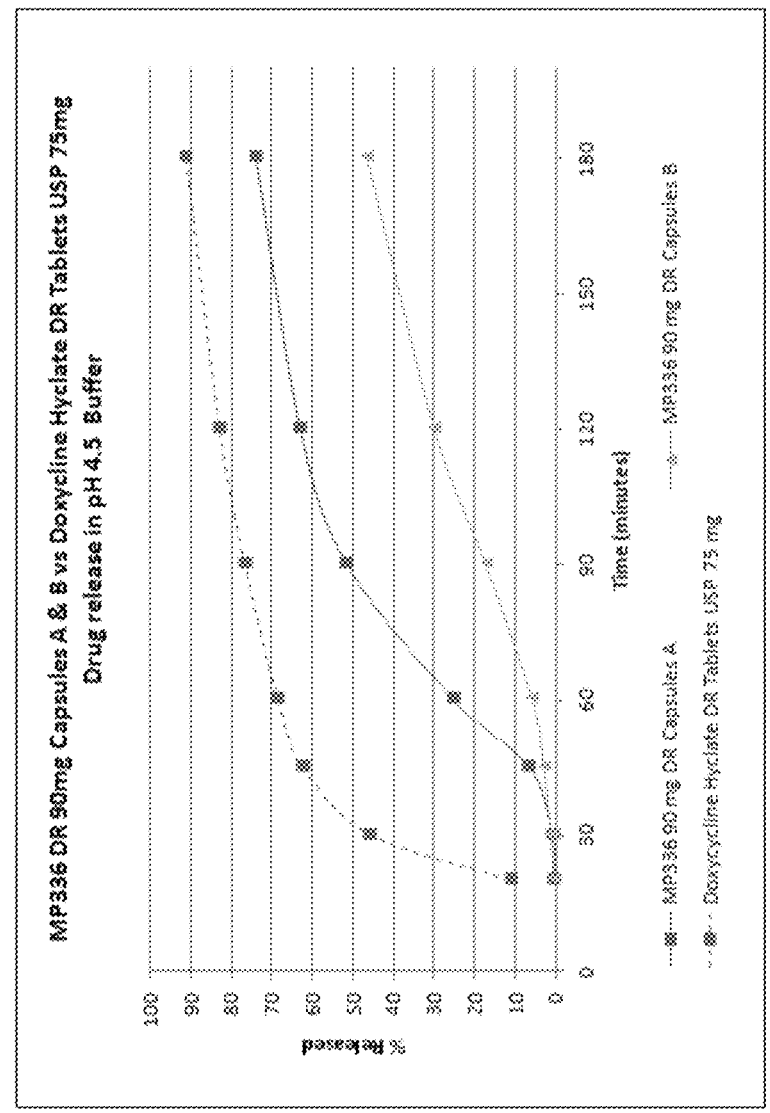

FIG. 10 is a graph illustrating the dissolution profile at pH 4.5 of a controlled release pellet formulation (A or B, 90 mg doxycycline) of the disclosure compared to a control 75 mg DORYX tablet.

Figure 11:
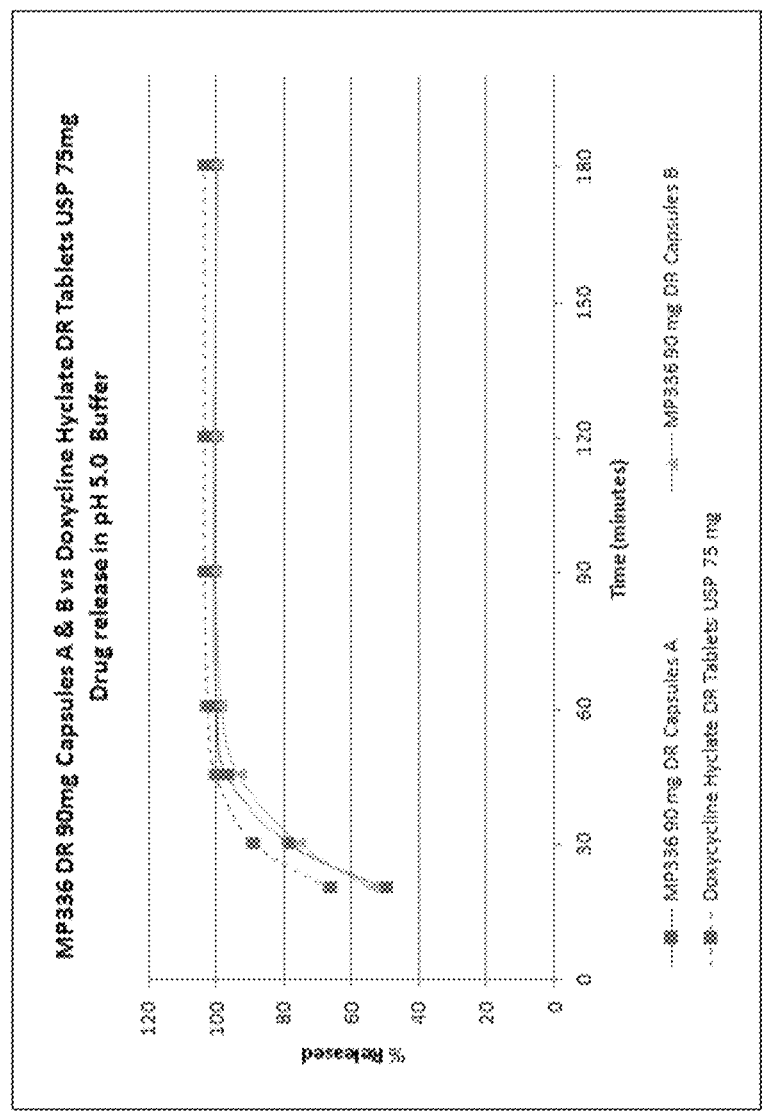

FIG. 11 is a graph illustrating the dissolution profile at pH 5.0 of a controlled release pellet formulation (A or B, 90 mg doxycycline) of the disclosure compared to a control 75 mg DORYX tablet.

Figure 12:
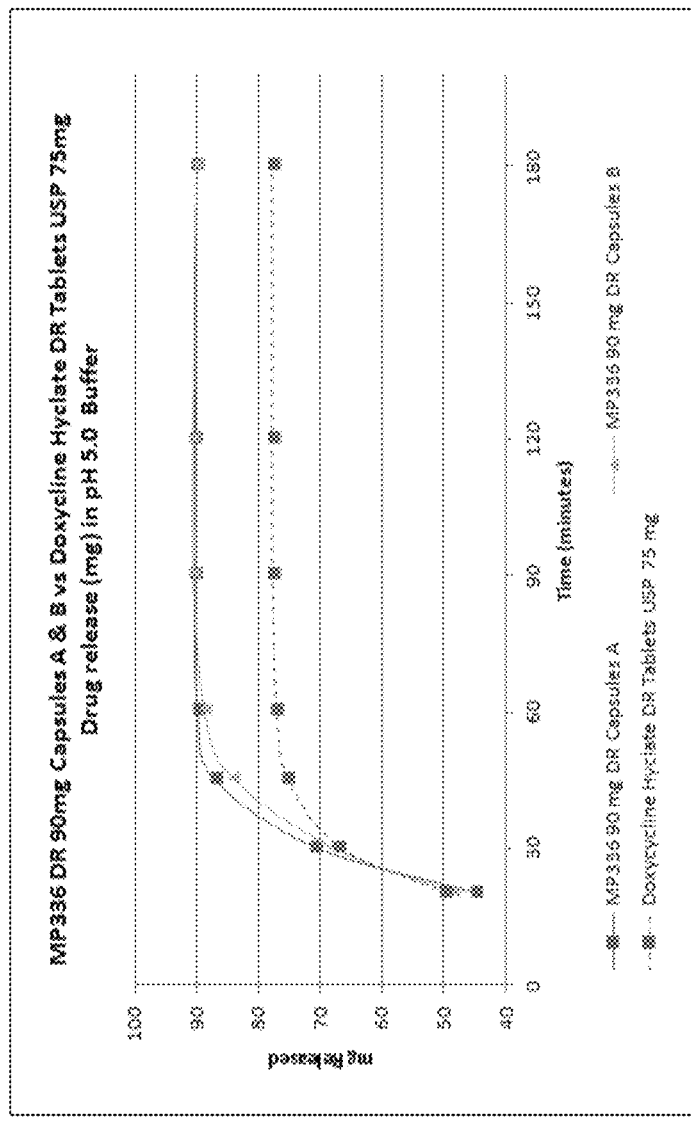

FIG. 12 is a graph illustrating the dissolution, in mg doxycycline released at pH 5.0 of a controlled release pellet formulation (A or B, 90 mg doxycycline) of the disclosure compared to a control 75 mg DORYX tablet.

Figure 13:
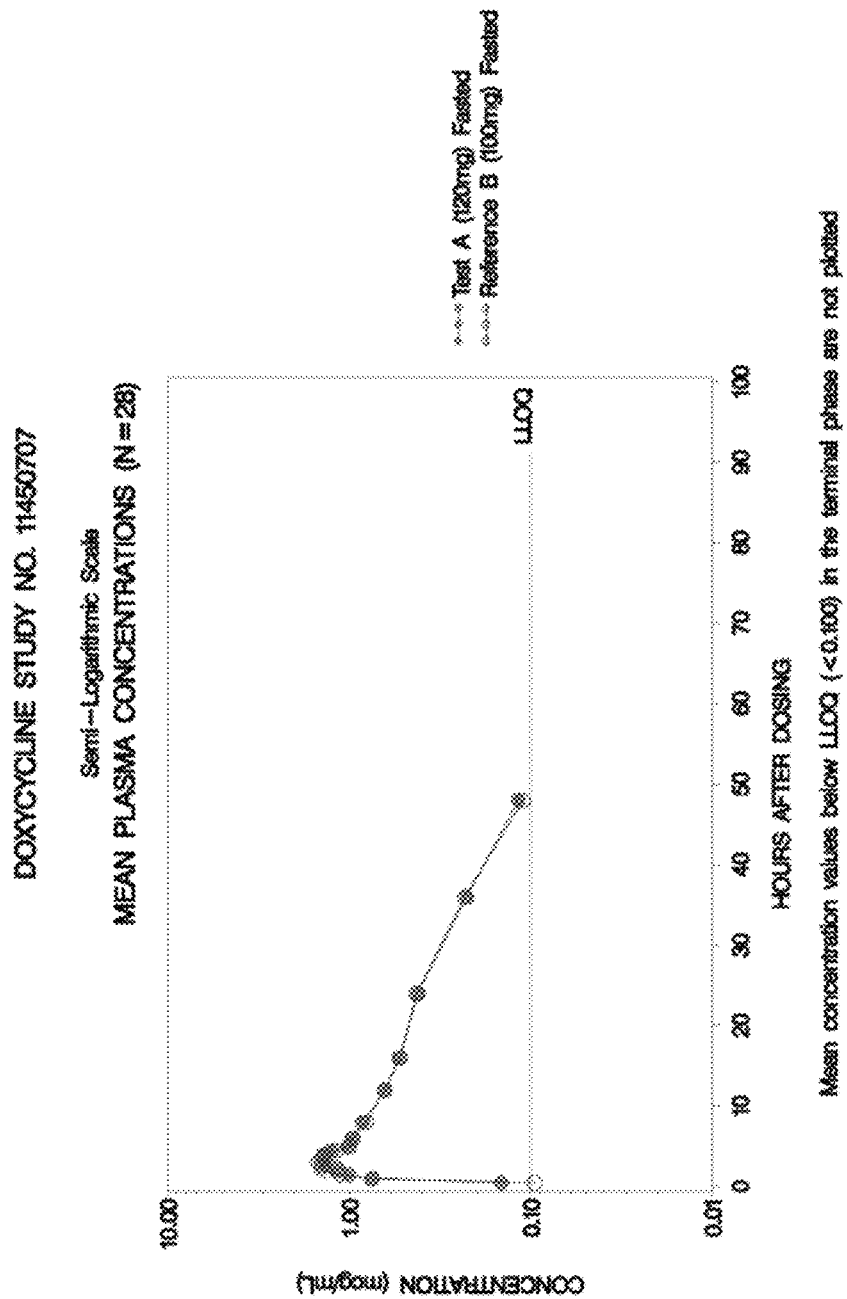

FIG. 13 is a graph of the mean plasma concentration versus time plot (semi-log) of doxycycline present in the plasma of subjects treated with a dosage form (i.e. a tablet) comprising controlled release doxycycline pellet formulation B (120 mg) compared to a reference DORYX doxycycline tablet (100 mg) under fasted conditions, as outlined in Example 7.

Figure 14:
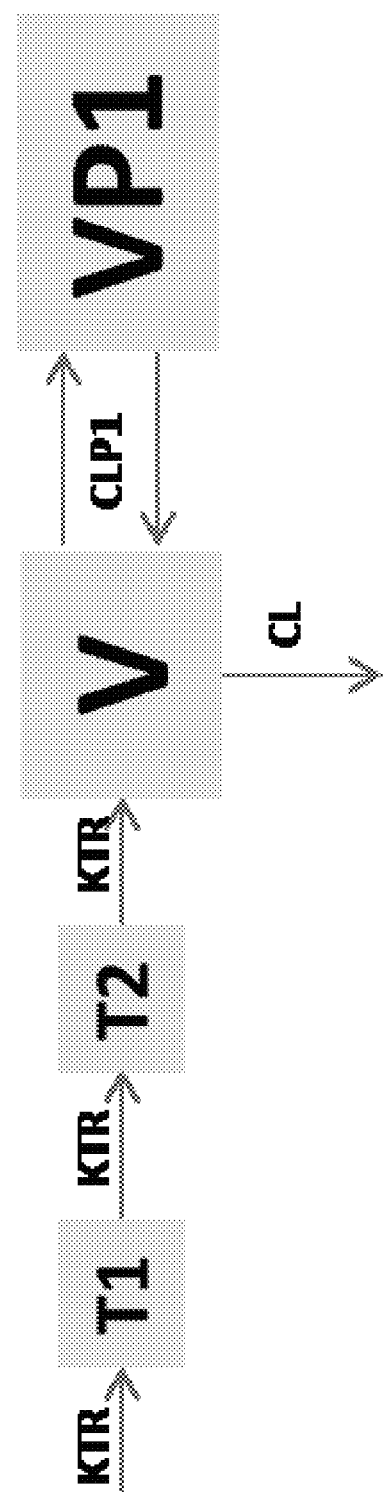

FIG. 14 illustrates the structural components of the base model. CL=apparent clearance; V=apparent central distribution volume; CLP1=apparent intercompartmental clearance; VP1=peripheral distribution volume; KTR=Transit absorption rate; T1 and T2=transit absorption compartments.

Figure 15:
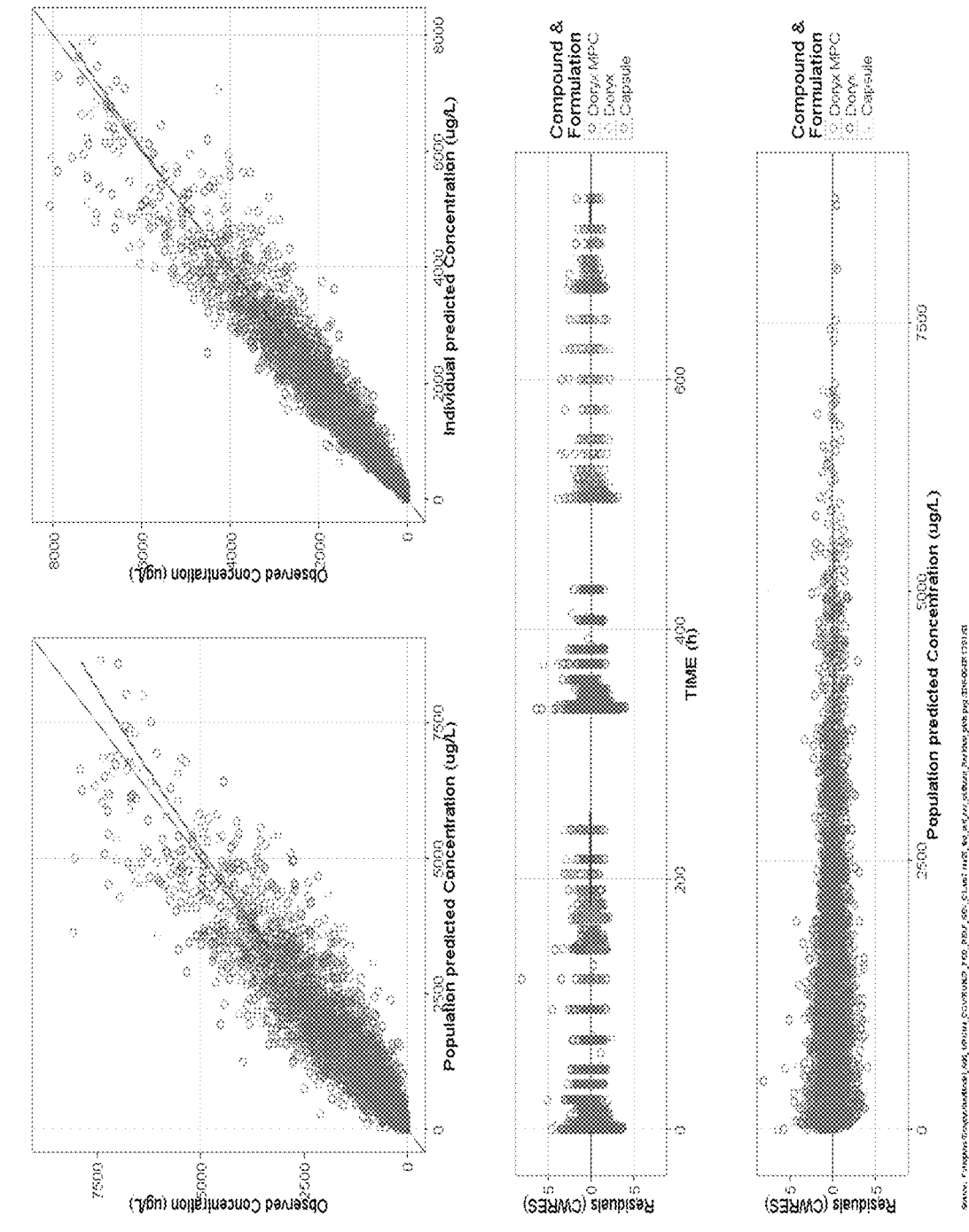

FIG. 15 illustrates the diagnostic plots for doxycycline concentrations following Doryx MPC (red), Doryx (blue) and Doryx Capsule (green) administration from the final model. Symbols are data points, the solid black line is a line of identity with slope 1 or 0, and the red lines are a loess-smooth of the data. CWRES=conditional weighted residuals.

Figure 16:
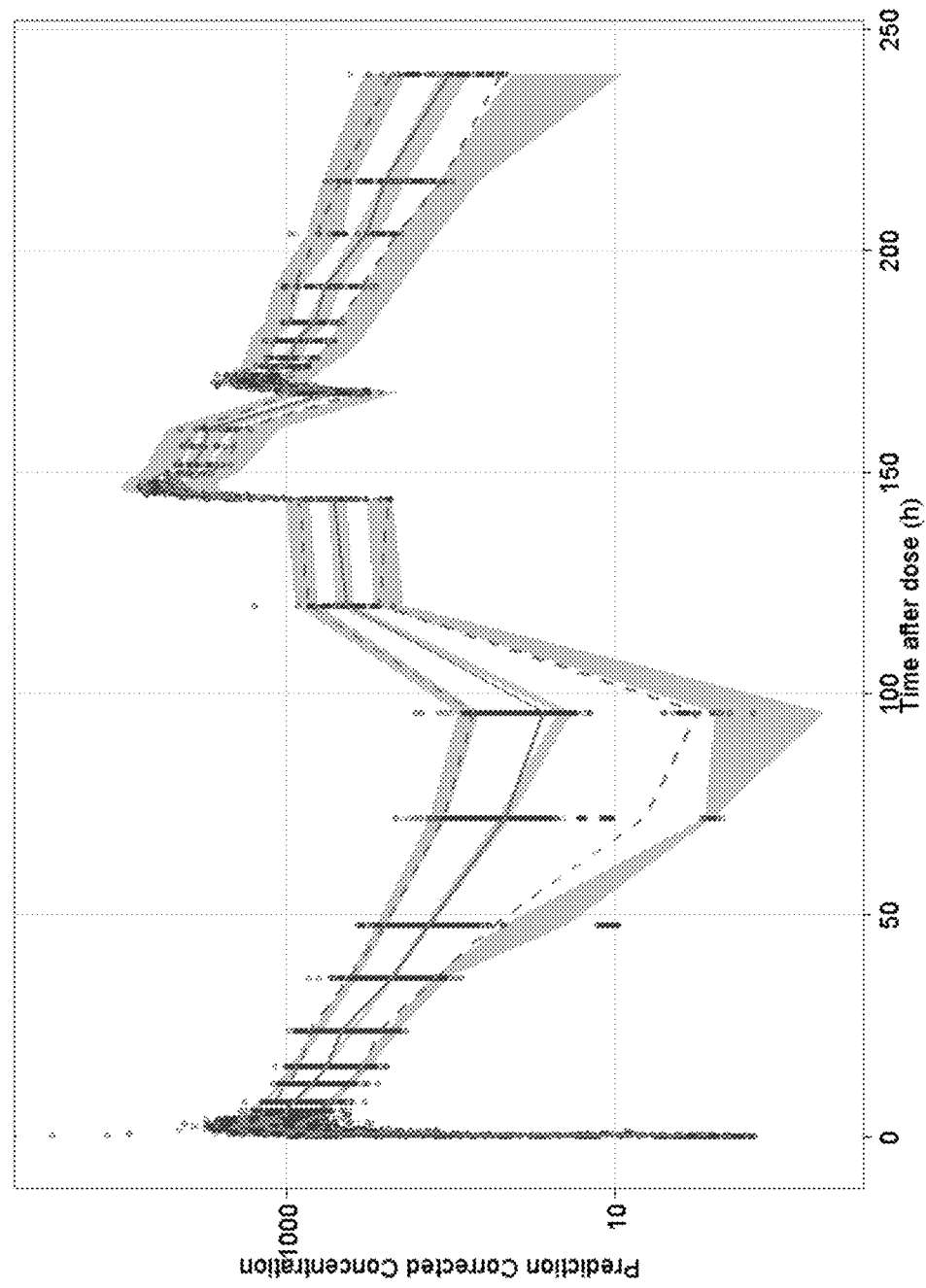

FIG. 16 illustrates the pcVPC of the final model for doxycycline concentrations. The prediction-corrected observed data are represented by blue circles, the red solid line (median), and the red dashed lines ($5^{th}$ and $95^{th}$ percentiles). The simulated prediction-corrected doxycycline concentrations are represented by the red shaded area (empirical 95% confidence interval of median) and the blue shaded areas (empirical 95% confidence intervals of 5th and 95th percentiles). The model predictions overlay the observed data with good agreement.

Figure 17:
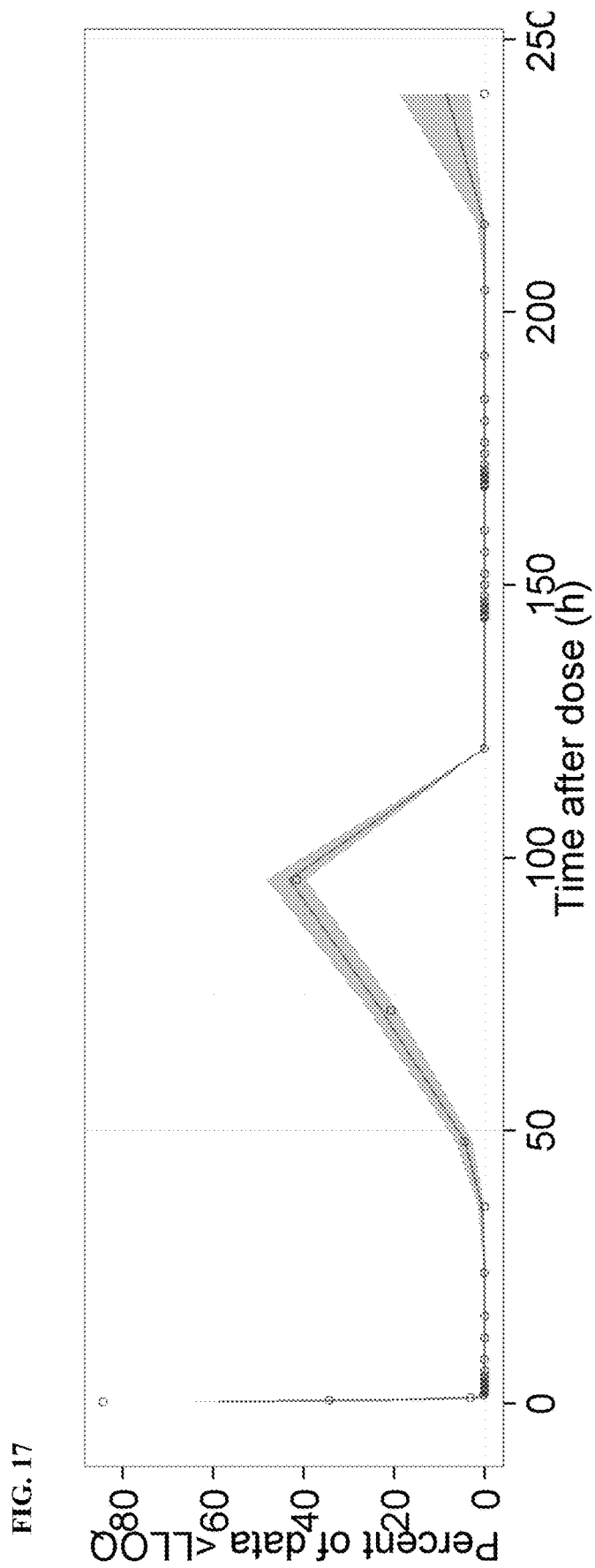

FIG. 17 illustrates the BLOQ VPC of the final model for doxycycline concentrations BLOQ (<LLOQ). The observed BLOQ data throughout time are represented by the blue circles. The simulated BLOQ data are represented by the 95% CI (red shaded area) and the median (solid red line). The prediction of the 95% CI of the BLOQ throughout time from the model overlies the observed data with good agreement.

DETAILED DESCRIPTION

Provided herein are pharmaceutical compositions comprising a tetracycline antibiotic. In most embodiments, the pharmaceutical composition comprises doxycycline.

Also provided herein are methods of treating a patient in need thereof with the pharmaceutical compositions of the present invention. In various aspects, the patients are treated for bacterial infections. In particular aspects, the patients are treated with pharmaceutical compositions according to the present invention to control skin conditions. A non-limiting list of skin conditions treatable with the pharmaceutical compositions of the present invention includes skin infections, rosacea, acne, papules, pustules, open comedo, closed comedo, etc., including combinations thereof.

While the following terms are believed to be well understood by one of ordinary skill in the art, the following definitions are set forth to facilitate explanation of the presently disclosed subject matter.

The verb "comprise" and its conjugations, are used in the open and non-limiting sense to mean that items following the word are included, but items not specifically mentioned are not excluded "About" in reference to a numerical value refers to the range of values somewhat less or greater than the stated value, as understood by one of skill in the art. For example, the term "about" could mean a value ranging from plus or minus a percentage (e.g., ±1%, 2%, or 5%) of the stated value. Furthermore, since all numbers, values, and expressions referring to quantities used herein are subject to the various uncertainties of measurement encountered in the art, then unless otherwise indicated, all presented values may be understood as modified by the term "about."

As used herein, the articles "a," "an," and "the" may include plural referents unless otherwise expressly limited to one-referent, or if it would be obvious to a skilled artisan from the context of the sentence that the article referred to a singular referent.

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include any and all subranges between the minimum value of 1 and the maximum value of 10. Exemplary subranges of the range "1 to 10" include, but are not limited to, e.g., 1 to 6.1, 3.5 to 7.8, and 5.5 to 10.

As used herein, the term "polymer" is meant to encompass both natural and synthetic macromolecules, including e.g., homopolymers (polymers having only one type of repeating unit), copolymers (a polymer having more than one type of repeating unit), graft copolymers, block copolymers, etc.

"Biodegradable polymer" means a polymer or polymers, which degrade in vivo, under normal physiological conditions. The erosion of a biodegradable polymer over time occurs concurrently with, or subsequently to, release of the therapeutic agent.

The terms "biodegradable" and "bioerodible" are used interchangeably herein. A biodegradable polymer may be a homopolymer or a copolymer.

As used herein, the term "matrix" denotes a solid mixture composed of a continuous phase (often of a dissolvable or biodegradable polymer), and one or more dispersed phase(s) (e.g., particles of the pharmaceutically active ingredient such as a tetracycline, specifically doxycycline). A "polymer matrix" may refer to a matrix in which the continuous phase is a single polymer or a mixture of polymers. The mixture of polymers may be of the same class, e.g. two different PLA polymers, or of different classes, e.g. PLA polymers combined with PLGA polymers.

By "immediate release" formulation is meant a dosage form that is intended to release substantially the entire dose of active ingredient on administration with no enhanced, delayed, controlled, sustained, or extended release effect, generally over a short period of time (e.g., 30 minutes).

As discussed herein, conventional "immediate release" tetracycline-containing pharmaceutical compositions which release the tetracycline in the stomach cause nausea and irritation which can reduce compliance by patients in need of such drugs. "Controlled-release" refers to a release profile which differs from "immediate release" in that the drug is released more slowly and/or after a delay or lag time such that the release of the tetracycline in the stomach is avoided. Controlled release can be provided by a variety of different types of formulations as described herein, such as matrix compositions, or beads coated with a controlled release coating layer.

In most embodiments, the controlled release composition of doxycycline is in solid form, for example a granulate (e.g., aggregated particles containing doxycycline, produced by wet or dry granulation processes), drug layered beads (e.g., doxycycline coated onto an inert core particle, such as a sugar bead or nonpareil, optionally including a binder to promote adhesion of the doxycycline to the core particle), or matrix composition (e.g., doxycycline incorporated into a biodegradable/bioerodible, controlled or soluble polymeric continuous phase (e.g., such as a controlled release polymer phase).

As used herein, the term "patient" refers to an animal who is to be administered a pharmaceutical composition as taught herein. The animal may be a mammal, such as a human.

"Therapeutically effective amount" means a level or amount of an agent needed to treat a condition. Thus, a therapeutically effective amount of a therapeutic agent, such as doxycycline, is an amount that is effective in reducing at least one symptom of a patient.

For example, a "therapeutically effective amount" of doxycycline is meant that amount of doxycycline, or its pharmaceutically acceptable salt, which either maintains or reduces the severity of a condition or symptom treatable with doxycycline. The therapeutically effective amount is determined by an ordinarily skilled artisan, taking into account various considerations, such as: the age of the subject, the weight of the subject, the condition of the subject, the type of subject (i.e., the type of animal), the regimen, the desired result, and the like.

The terms "therapeutic agent", "active agent", "drug", and "active pharmaceutical ingredient" are used interchangeably herein.

Tetracyclines are a group of broad-spectrum antibiotics named for their four ("tetra-") hydrocarbon rings ("-cycl-") derivation ("-ine"). To be specific, they are defined as a subclass of polyketides having an octahydrotetracene-2-carboxamide skeleton. They are collectively known as derivatives of polycyclic naphthacene carboxamide.

The structure of Tetracycline can be found below:

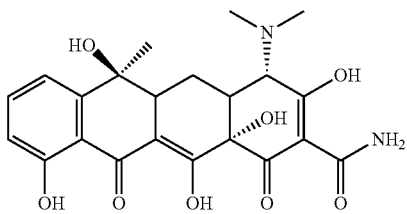

(4S,6S,12aS)-4-(dimethylamino)-3,6,10,12,12a-pentahydroxy-6-methyl-1,11-dioxo-1,4,4a,5,5a,6,11,12a-octahydrotetracene-2-carboxamide Doxycycline is an antibiotic useful for the treatment of a number of infections. It is in the tetracycline antibiotic class. Doxycycline formulations are sold commercially under a variety of names, including: DORYX®, VIBRAMYCIN®, MONODOX®, MICRODOX®, PERIOSTAT®, VIBRA-TABS®, ORACEA®, VIBROX®, ADOXA®, DOXY-HEXAL®, DOXYLIN®, DOXORAL®, DOXY-1®, and ATRIDOX®. The term "doxycycline" as used herein includes salts of doxycycline (below) including pharmaceutically acceptable salt, solvates, or solvated salts of doxycycline.

The structure of doxycycline can be found below:

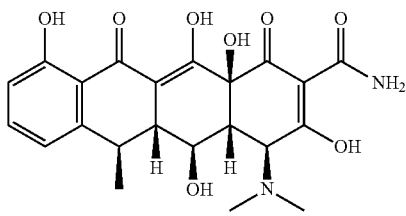

(4S,4aR,5S,5aR,6R,12aS)-4-(dimethylamino)-3,5,10,12,12a-pentahydroxy-6-methyl-1,11-dioxo-1,4,4a,5,5a,6,11,12a-octahydrotetracene-2-carboxamide The most common forms of doxycycline used in commercial pharmaceutical formulations include the monohydrate form and the hyclate form. The monohydrate is the base molecule hydrated with one molecule of water and is used in the formulation of capsules and, in some markets, powder oral suspensions (to be reconstituted with water). The hyclate is a hydrochloric acid salt solvated with water and ethanol and is typically used in the formulation of capsules or tablets.

The structure of doxycycline hyclate is found below:

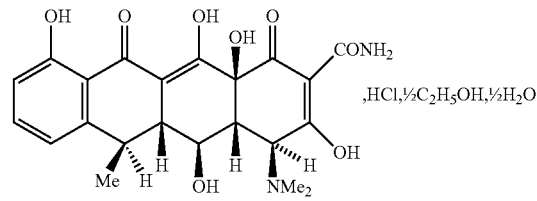 [SMILES: C[C@H]1c2cccc(O)c2C(=O)C2=C(O)[C@]3(O)C(=O)C(C(N)=O)=C(O)[C@@H](N(C)C)[C@@H]3[C@@H](O)[C@@H]21]

with a molecular formula of $C_{22}H_{24}N_2O_8$, HCl, ½ $C_2H_6O$, ½ $H_2O$ and a molecular weight of 512.9.

The chemical designation for doxycycline hyclate is [4S (4aR,5S,5aR,6R,12aS)]-4-(dimethylamino)-1,4,4a,5,5a,6, 11,12a-octahydro-3,5,10,12,12a-pentahydroxy-6-methyl-1, 11-deoxonapthtacene-2-carboxamide monohydrochloride, compound with ethyl alcohol (2:1), monohydrate. Doxycycline hyclate is a yellow crystalline powder soluble in water and in solutions of alkali hydroxides and carbonates. Doxycycline has a high degree of lipid solubility and a low affinity for calcium binding. It is highly stable in normal human serum. Doxycycline will not degrade into an epianhydro form.

U.S. Pat. Nos. 6,958,161 and 8,715,724, disclose various embodiments of doxycycline compositions and methods of making and using the same. The disclosures of each of these patents are herein incorporated by reference in their entireties for all purposes.

Further, U.S. Pat. Nos. 8,470,364; 8,394,406; 8,394,405; 8,206,740; 7,910,128; 7,749,532; 8,603,506; 7,232,572; 8,652,516; and U.S. Patent Application Publication US20120100214 (U.S. application Ser. No. 13/278,989); and PCT Publication No. WO2012059338, disclose various embodiments of doxycycline compositions and methods of making and using the same. The disclosures of each of these documents are herein incorporated by reference in their entireties for all purposes.

Doxycycline is virtually completely absorbed after oral administration. For instance, following single and multiple-dose administration of DORYX Tablets, 200 mg to adult volunteers, average peak plasma doxycycline concentration ($C_{max}$) was 4.6 mcg/mL and 6.3 mcg/mL, respectively with median $T_{max}$ of 3 hours; the corresponding mean plasma concentration values 24 hours after single and multiple doses were 1.5 mcg/mL and 2.3 mcg/mL, respectively.

Further, following a 200 mg dose, normal adult volunteers averaged peak serum levels of 2.6 mcg/mL of doxycycline at 2 hours decreasing to 1.45 mcg/mL at 24 hours. Excretion of doxycycline by the kidney is about 40%/72 hours in individuals with normal function (creatinine clearance about 75 mL/min). This percentage excretion may fall as low as 1-5%/72 hours in individuals with severe renal insufficiency (creatinine clearance below 10 mL/min).

The mean $C_{max}$ and $AUC_{0-\infty}$ of doxycycline are 24% and 13% lower, respectively, following single dose administration of DORYX Tablets, 100 mg with a high fat meal (including milk) compared to fasted conditions.

The mean $C_{max}$ of doxycycline is 19% lower and the $AUC_{0-\infty}$ is unchanged following single dose administration of DORYX Tablets, 150 mg with a high fat meal (including milk) compared to fasted conditions.

Doxycycline bioavailability from DORYX Tablets, 200 mg was not affected by food, but the incidence of nausea was higher in fasted subjects. The 200 mg tablets may be administered without regard to meals.

The compositions of the present invention provide $AUC_{0-\infty}$ values within 80-125% of 10000-24000 ng·hr/ml following administration of a 60 mg dose under fasting conditions.

The compositions of the present invention provide $AUC_{0-\infty}$ values within 80-125% of 15000-36500 ng·hr/ml following administration of a 90 mg dose under fasting conditions.

The compositions of the present invention provide $AUC_{0-\infty}$ values within 80-125% of 20000-48500 ng·hr/ml following administration of a 120 mg dose under fasting conditions.

The compositions of the present invention provide $C_{max}$ values within 80-125% of 625-1600 ng/ml following administration of a 60 mg dose under fasting conditions.

More particularly, the compositions of the present invention provide $C_{max}$ values within 80-125% of 725-1600 ng/ml following administration of a 60 mg dose under fasting conditions The compositions of the present invention provide $C_{max}$ values within 80-125% of 940-2400 ng/ml following administration of a 90 mg dose under fasting conditions.

More particularly, the compositions of the present invention provide $C_{max}$ values within 80-125% of 1100-2400 ng/ml for a 90 mg dose.

The compositions of the present invention provide $C_{max}$ values within 80-125% of 1250-3200 ng/ml following administration of a 120 mg dose under fasting conditions.

More particularly, the compositions of the present invention provide $C_{max}$ values within 80-125% of 1450-3200 ng/ml following administration of a 120 mg dose under fasting conditions.

In addition, the compositions of the present invention have pharmacokinetic characteristics which differ from that of conventional formulations which have essentially the same (e.g., bioequivalent) $AUC_{0-\infty}$ values, particularly shortly after administration. For example, 90 mg doxycycline compositions according to the present invention are bioequivalent to conventional 75 mg DORYX compositions. However, compositions according to the present invention can have $AUC_{0-0.5\ hr}$ values of about 0 ng·hr/ml, compared to about 20 ng·hr/ml for DORYX; $AUC_{0-0.75\ hr}$ values of about 5-60 ng·hr/ml, compared to about 100 ng·hr/ml for DORYX; $AUC_{0-1\ hr}$ values of about 40-200 ng·hr/ml, compared to about 270 ng·hr/ml for DORYX; $AUC_{0-1.5\ hr}$ values of about 200-650 ng·hr/ml, compared to about 800 ng·hr/ml for DORYX; $AUC_{0-2\ hr}$ values of about 600-1250 ng·hr/ml, compared to about 1500 ng·hr/ml for DORYX; $AUC_{0-2.5\ hr}$ values of about 1100-2000 ng·hr/ml, compared to about 2200 ng·hr/ml for DORYX; $AUC_{0-3\ hr}$ values of about 1800-2700 ng·hr/ml, compared to about 3000 ng·hr/ml for DORYX; $AUC_{0-3.5\ hr}$ values of about 2500-3500 ng·hr/ml, compared to about 3700 ng·hr/ml for DORYX; $AUC_{0-4\ hr}$ values of about 3100-4200 ng·hr/ml, compared to about 4400 ng·hr/ml for DORYX; $AUC_{0-4.5\ hr}$ values of about 3800-5000 ng·hr/ml, compared to about 5200 ng·hr/ml for DORYX; $AUC_{0-5\ hr}$ values of about 4500-5700 ng·hr/ml, compared to about 5900 ng·hr/ml for DORYX; $AUC_{0-5.5\ hr}$ values of about 5100-6500 ng·hr/ml, compared to about 6500 ng·hr/ml for DORYX; $AUC_{0-6\ hr}$ values of about 5700-7000 ng·hr/ml, compared to about 7100 ng·hr/ml for DORYX; $AUC_{0-8\ hr}$ values of about 7500-9000 ng·hr/ml, compared to about 9000 ng·hr/ml for DORYX; $AUC_{0-12\ hr}$ values of about 10000-12000 ng·hr/ml, compared to about 12000 ng·hr/ml for DORYX; $AUC_{0-16\ hr}$ values of about 12000-15000 ng·hr/ml, compared to about 14000 ng·hr/ml for DORYX; $AUC_{0-24\ hr}$ values of about 16000-19000 ng·hr/ml, compared to about 18000 ng·hr/ml for DORYX; $AUC_{0-36\ hr}$ values of about 20000-23000 ng·hr/ml, compared to about 22000 ng·hr/ml for DORYX; $AUC_{0-48\ hr}$ values of about 22000-26000 ng·hr/ml, compared to about 25000 ng·hr/ml for DORYX; $AUC_{0-72\ hr}$ values of about 24000-29000 ng·hr/ml, compared to about 27000 ng·hr/ml for DORYX; and $AUC_{0-96\ hr}$ values of about 25000-29000 ng·hr/ml, compared to about 28000 ng·hr/ml for DORYX.

Figure 1:
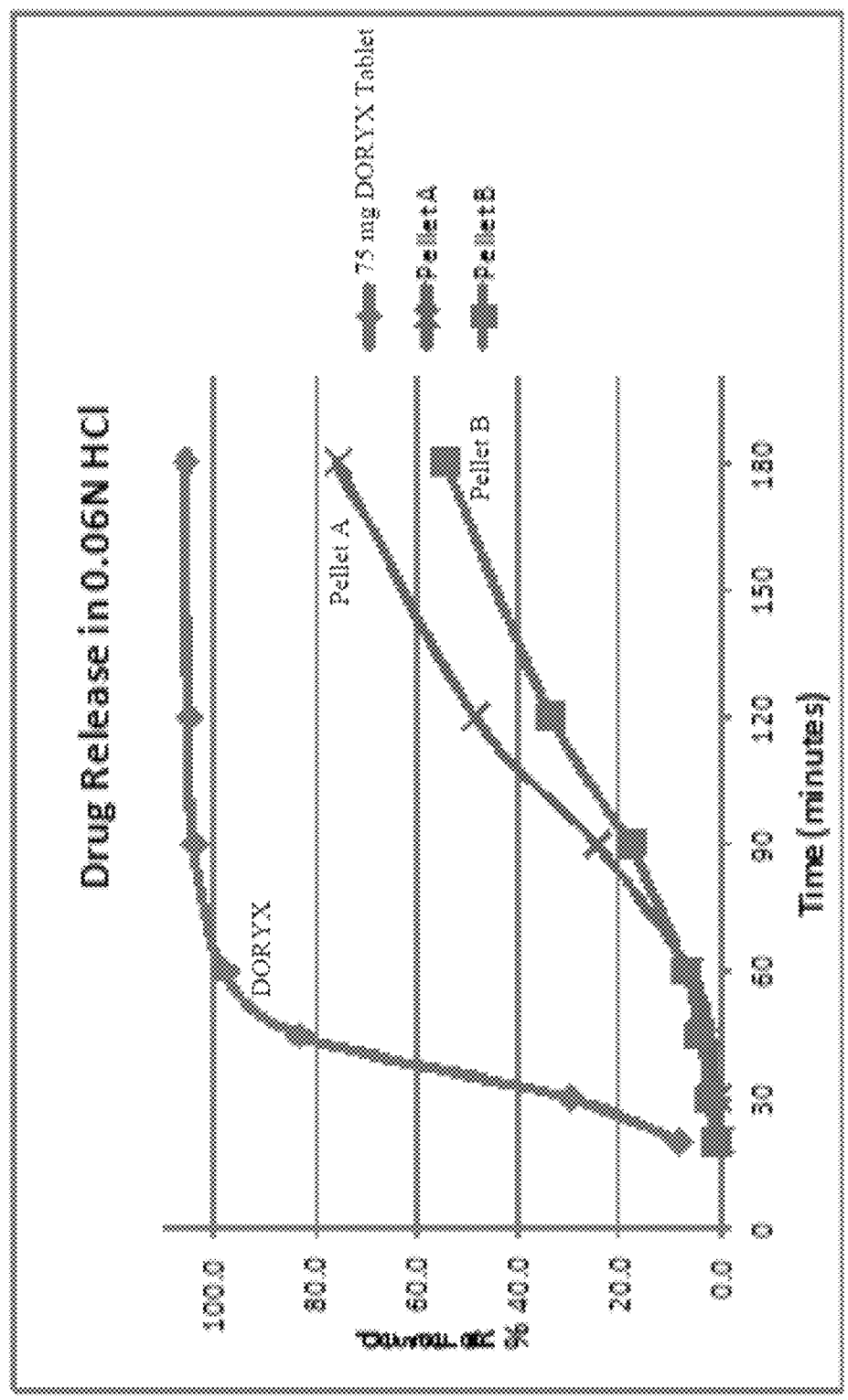
FIG. 1 is a graph illustrating the dissolution profile in acidic conditions of a controlled release pellet formulation (A or B) of the disclosure compared to a control DORYX tablet.

FIGS. 1, 2, 5, and 6 show typical dissolution curves for DORYX tablets measured under different pH conditions. FIG. 1 shows release data after 1 hour in 0.06N HCl, at approximately pH 1.2, typical stomach pH conditions. The initial release of the doxycycline in DORYX is modest, reflecting the enteric coated delayed release nature of the product. However, at 20 minutes the doxycycline release rates starts to rise rapidly and after 60 minutes the release has reached virtually 100%. Similarly, for the release rate of the product at pH 4.5, after 60 minutes approximately 70% of the product has been released. In pH 5 conditions, as might be expected, the release rate at pH 6 minutes is virtually 100%. An immediate release tablet formulation comprising doxycycline can be prepared by mixing doxycycline with a bulking agent such as microcrystalline cellulose, for example, AVICEL® (FMC Corp.) or EMCOCEL® (Mendell Inc.); dicalcium phosphate, for example, EMCOM PRESS® (Mendell Inc.); calcium sulfate, for example, COMPACTROL® (Mendell Inc.); and starches, for example, STARCH 1500. Additionally, one can add a disintegrating agent, such as microcrystalline cellulose, starches, crospovidone, for example, POLYPLASDONE XL® (International Specialty Products); sodium starch glycolate, for example, EXPLOTAB® (Mendell Inc.); and croscarmellose sodium, for example, AC-DI-SOL® (FMC Corp.). Antiadherants and glidants employed herein can include talc, cornstarch, silicon dioxide, sodium lauryl sulfate, colloidal silica dioxide, and metallic stearates.

Lubricants may be employed, such as magnesium stearate, calcium stearate, sodium stearate, stearic acid, sodium stearyl fumarate, sterotex, talc, waxes and the like.

Binding agents may be employed, such as polyvinyl pyrollidone, starch, methylcellulose, hydroxypropyl methylcellulose, carboxymethyl cellulose, and the like.

The immediate release formulations may be formed into a tablet using methods known in the art, including a wet granulation method and a direct compression method. The oral tablets are prepared using any suitable process known to the art. See, e.g., Remington's Pharmaceutical Sciences, 18th Edition, A. Gennaro, Ed., Mack Pub. Co. (Easton, Pa. 1990), Chapters 88-91, the entirety of which is hereby incorporated by reference. Typically, the active ingredient, which in embodiments is doxycycline (or salts and/or solvates thereof), is mixed with pharmaceutically acceptable excipients (e.g., the binders, lubricants, etc. listed above) and compressed into tablets.

In some embodiments, dosage forms of the present disclosure can be prepared by a wet granulation technique or a direct compression method to form uniform granulates. If a wet granulation technique is used, the moist granulated mass can be dried and sized using a suitable screening device to provide a powder, which can then be filled into capsules or compressed into matrix tablets or caplets, as desired. In particular embodiments, the moist granulated mass is extruded, cut and then spheronized and dried to form pellets. These pellets are then coated with an optional stabilizing coating, and a controlled-release coating, and then filled into capsules. Alternatively, the doxycycline pellets (formed by extrusion and spheronization or other methods known in the art) can be compressed into a tablet, optionally with other excipients.

In other embodiments, the compositions of the present disclosure can be prepared by coating the doxycycline onto an inert core, such as a sugar sphere or nonpareil, acid or alkaline buffer, or other inert core materials known in the art. The doxycycline can be coated onto the inert core using methods known in the art, such as Wurster coating, pan coating, etc. a solution or suspension of the doxycycline, optionally in the presence of a water-soluble, alcohol soluble, or acetone/water soluble binder, such as hydroxypropyl cellulose, hydroxypropyl methylcellulose, polyvinylpyrrolidone (PVP), polyethylene oxide, polysaccharides such as dextran, cornstarch, etc. If needed, the resulting drug layered core particles can be coated with a further, thin protective coating to reduce particle attrition during processing. Such protective coatings can include, for example, commercial product such as OPADRY Clear® (hydroxymethyl cellulose) or other primers such as hydroxypropyl cellulose. The resulting drug layered core particles, optionally overcoated with the thin protective coating described herein, can then be coated with a controlled-release polymer composition, as described herein, to provide the desired release and pharmacokinetic characteristics, and filled into a capsule or compressed into a tablet.

In other embodiments, the compositions of the present invention can be prepared by spray drying. For example, the doxycycline and suitable excipients can be suspended or dissolved in a suitable solvent, such as water, alcohols, or acetone, including mixtures thereof, and spray dried to form particles comprising the doxycycline and excipient(s). Such particles can be optionally mixed with other excipients and compressed into a tablet, or filled into a capsule. The optional other excipients can comprise a controlled release polymer composition, whereby the doxycycline is encapsulated into a controlled release polymer composition matrix, or the particles can be overcoated with a controlled release polymer coating before being compressed into tablets or filled into a capsule.

In an embodiment, matrix tablets are prepared using the direct compression method. The direct compression method offers a number of potential advantages over a wet granulation method, particularly with respect to the relative ease of manufacture. In the direct compression method, at least one pharmaceutically active agent and the excipients or other ingredients are sieved through a stainless steel screen, such as a 40 mesh steel screen. The sieved materials are then charged to a suitable blender and blended for 10 minutes with an intensifier bar for three minutes. The blend is then compressed into tablets on a rotary press using appropriate tooling.

As aforementioned, immediate release formulations of tetracycline antibiotics suffer from a number of drawbacks, such as gastrointestinal irritation and nausea. Thus, although the present specification provides methods for producing such immediate release formulations, the following exemplary embodiments of controlled release tetracycline (e.g. doxycycline) formulations are advantageous over such immediate release formulations.

The controlled release formulations described herein exhibit a beneficial release profile that reduces or prevents nausea in patients administered the formulation. Furthermore, the controlled release formulations described in the present disclosure have a superior release profile compared to that of other doxycycline formulations.

In a particular aspect, the present invention provides for tablets or capsules comprising controlled release compositions of doxycycline. In various embodiments, the tablets or capsules can be prepared from, or be filled with, beads, particles or pellets containing doxycycline, in which the beads, particles or pellets can comprise a controlled-release matrix containing doxycycline, or the beads, particles pellets are coated with one or more layers of controlled release coating(s).

In specific embodiments, the controlled release formulations of the present invention comprise doxycycline-containing particles coated with a controlled release coating comprising an enteric polymer. In other specific embodiments, the controlled-release formulations of the present invention comprise doxycycline-containing particles coated with a controlled-release coating comprising a mixture of an enteric polymer and a water-soluble polymer. In still other embodiments, the controlled-release coating (e.g., a mixture of an enteric polymer and a water-soluble polymer, or solely an enteric polymer), further comprises a plasticizer.

In other embodiments, the pellets are coated with one layer of controlled-release coating (as described herein above), or two or more layers of controlled-release coating. Each of the controlled-release coatings can be the same or different.

Methods for making such controlled release pellets are set forth below. The pellets can be filled into capsules, for instance gelatin capsules, by conventional techniques. The pellets can also be incorporated into tablets, e.g. by compression using conventional techniques.

Controlled Release Pellets

In various embodiments, the controlled release preparations of the present disclosure will be formulated from a plurality of pellets.

In some embodiments, each pellet comprises a drug-containing core, coated with a controlled-release coating. In various aspects, the core comprises a tetracycline antibiotic. In a particular aspect, the core comprises doxycycline and the controlled release coating comprises an enteric polymer.

In some embodiments, a stabilizing coat is disposed between the core and the controlled release coating.

In one embodiment, a plurality of such pellets as described above may be provided in a capsule.

In alternative embodiments, a plurality of such pellets may be compressed, along with suitable optional tablet excipients, and provided as a tablet.

It is also possible for the dosage form to be a single coated core, large enough itself to be referred to as a tablet.

While suitable tableting excipients will be known to a person skilled in the art, proper formulation of the tablet usually involves balancing the need for content uniformity (namely, making sure the same number of pellets is present in each tablet and therefore the same amount of active ingredient is present in each tablet) and the amount of excipients required to protect the friable coating of the controlled release pellets. In this respect, if the number of pellets is too low, there may be problems with content uniformity, while if the number of pellets is too high there will not be enough tableting excipients to cushion the pellets during compression into a tablet and the modified release coating could be compromised. Therefore, the percentage of pellets in each tablet may be in the range of 20% to 40%, or in the range of 25% to 35%, or approximately 30% by weight of the total dosage weight.

Dosage forms (e.g. tablets or pellets suitable for filling into capsules) according to the present invention may further comprise excipients such as fillers, binders, disintegrants, and lubricants along with the active ingredient. Optionally, the dosage form (particularly tablets) may also contain other ingredients such as flavors, coloring agents, etc. The range of materials that are suitable for use as fillers, disintegrants, binders, lubricants, diluents, plasticizers, anti-caking agents, solubilizing agents, stabilizers, anti-oxidants, anti-adherents, preservatives, glidants, flavorants, sweeteners, and pigments will be well known to the person skilled in the art.

Suitable fillers include inert, relatively tasteless or pleasant tasting materials. A nonlimiting list of suitable fillers includes cellulose (e.g. microcrystalline cellulose), starch (e.g. corn starch), pregelatinized starch, modified starch, dibasic calcium phosphate dihydrate, calcium sulfate trihydrate, calcium sulfate dihydrate, calcium carbonate, dextrose, sucrose, lactose, mannitol, and sorbitol. Lactose monohydrate is used as filler in certain embodiments. In certain embodiments, the filler is at least one member selected from the group consisting of: lactose monohydrate, cellulose microcrystalline, corn starch, and combinations thereof.

A nonlimiting list of suitable disintegrants includes cross-linked polymers such as crospovidone, croscarmellose sodium, etc., and modified starches such as sodium starch glycolate.

A nonlimiting list of suitable binders includes disaccharides such as sucrose and lactose, polysaccharides such as cellulose, starches, microcrystalline cellulose, modified celluloses such as hydroxypropyl cellulose, sugar alcohols such as xylitol, sorbitol, or maltitol, proteins such as gelatin, synthetic polymers such as polyvinyl pyrrolidone and polyethylene glycol, starches, such as potato starch, wheat starch, corn starch, and gums, such as gum tragacanth, acacia gum and gelatin.

A nonlimiting list of suitable lubricants includes magnesium stearate or stearic acid.

Plasticizers utilized in some embodiments include, but are not limited to, citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and dibutylsebacate, dibutylsuccinate, dibutyltartrate; diethylene glycol dipropionate; ethyleneglycol diacetate, dibutyrate, -dipropionate; tributyl phosphate, tributyrin; polyethylene glycol sorbitan monooleate (polysorbates such as Polysorbar 50); sorbitan monooleate. A combination of plasticizers may also be used. In aspects, the plasticizer for use with the cellulose polymer is polyethylene glycol, such as polyethylene glycol 600. In other aspects, the plasticizer for use with the enteric coating polymer is a combination of triethyl citrate and glycerol monostearate. In particular embodiments, the plasticizer comprises triethyl citrate (TEC).

It is also well known in the art that certain excipients may have multiple functions; e.g., function as fillers and binders.

In embodiments, lactose and/or starch are used as fillers in the dosage form. The total amount of lactose plus starch present in the dosage form can range between 50% to 95% w/w, based on the total weight of the tablet.

A suitable disintegrant for use in a dosage form of the present invention is crospovidone, and this may be present in a range of 0% to 15% w/w, based on the total weight of the tablet.

A suitable lubricant for use in a dosage form of the present invention is magnesium stearate and the lubricant may be present in a range of between 0.2% to 1.0% w/w, based on the total weight of the tablet.

Core of the Controlled Release Pellets

In other embodiments, the drug-containing core comprises active ingredient (e.g., doxycycline) mixed within and through the core. The core may be formed by any suitable method. For example, the core elements may be formed by layering the drug onto an inert core (e.g., a sugar bead or nonpareil, silica bead, etc., optionally in the presence of a binder to promote adhesion of the drug onto the inner core), extrusion, spheronization, or rotogranulation. For example, the drug-containing core can comprise a mixture of the drug (e.g. doxycycline) and the filler or other excipient (e.g. microcrystalline cellulose) which are granulated (typically, wet granulated, but also dry granulated) to form (after drying, if necessary) either a "granulate" which are aggregated particles made up of drug and excipient particles adhered together. Alternatively, the drug and excipients can be wet granulated to form an extrudable mass which is extruded and cut into particles, and optionally spheronized to form drug-containing cores The active ingredient, in particular embodiments, is a tetracycline antibiotic (including salts, esters, and/or solvates thereof). In specific embodiments, the active ingredient is doxycycline. In some embodiments, the active ingredient is the monohydrate form of doxycycline. In further embodiments, the active ingredient is the hyclate salt form of doxycycline.

In embodiments, before coating with an optional stabilizing coat and the controlled release coating, the drug-containing cores have a diameter in the range of 50 microns to 2000 microns. Alternatively, if the drug is formulated into matrix tablets, the size of such tablets ranges from 5 mm to 20 mm.

It will be appreciated that the drug-containing cores may contain any suitable or required additives, such as excipients, fillers, or other ingredients.

In one embodiment, the core is formed by extrusion using an extruding solution. The core composition contains, in addition to the active ingredient, a binder.

In various embodiments, the binder is microcrystalline cellulose; however, powdered cellulose or any of the co-processed microcrystalline celluloses that contain additives such as silica, may be used. In embodiments, the amount of binder used ranges between about 6% to 45% by weight, based on the total weight of the core.

In embodiments, a wicking agent or water transport modifier may also be present in the core formulation. A wicking agent allows water to be transported throughout the core and aids in the complete release of active ingredient in the core. In certain aspects, the wicking agent is selected from lactose, starch, or sorbitol. In a particular embodiment, the wicking agent is lactose. The wicking agent may be present in an amount of from about 0% to 45% by weight, based on the total weight of the core.

Optionally, the core formulation may also include a lubricant, and a number of suitable lubricants will be known to the person skilled in the art. In a particular aspect, the lubricant is selected from sodium lauryl sulphate or magnesium stearate. In some aspects, the lubricant is present in an amount ranging from about 0% to 10% by weight, based on the total weight of the core.

The active ingredient (e.g., doxycycline) may be present in the core element in any suitable amount, and for instance may be provided in an amount from about 5% to 95% by weight, or from about 20% to 80% by weight, based on the total weight of the core element. In some embodiments, the amount of doxycycline (and salts and/or solvates thereof) is about 60% to about 80%, or about 70% to about 80%, or about 72% of the weight of the core element.

A person skilled in the art of making cores for pellets will be familiar with other materials that may be used to provide the same physical effects as the binder, the wicking agent, or the lubricant.

The active ingredient may be any suitable and desirable pharmaceutical, medicament, or chemical. For example, the active ingredient may be acid addition salts of doxycycline, tetracycline, oxytetracycline, minocycline, chlortetracycline, or demeclocycline. Any active ingredient that causes nausea or gastrointestinal irritation, but also has a narrow absorption window in the upper intestinal tract will benefit from the application of this disclosure.

In embodiments, the core comprises a tetracycline.

In other embodiments, the core comprises doxycycline.

In particular embodiments, the core element comprises the hyclate salt of doxycycline. In some aspects, the core element comprises the hyclate salt of doxycycline in amounts ranging from about: 1% to about 99% by weight, or 5% to 95% by weight, or from about 20% to 80% by weight, or about 50% to about 80% by weight, or about 60% to about 80% by weight, or about 70% to about 80% by weight or about 72% by weight based on the total weight of the core element.

Stabilizing Coating

The stabilizing coating is a physical barrier between the active ingredient (e.g. doxycycline) and the controlled release coating. The stabilizing coating may also be referred to as a tie coat, seal coat, or an intermediary layer.

The purpose of the stabilizing coating is to keep the active ingredient and the controlled release coating separated. In this respect, it is believed that the stabilizing coating slows migration of moisture or solvent between the modified release coating and the active ingredient. Whilst the stabilizing coating will keep the active ingredient separated from the controlled release coating during storage, the stabilizing coating will ideally not interfere significantly with the rate of release of the active ingredient, and therefore should be at least semi-permeable in aqueous media and may even be soluble. Indeed, the stabilizing coating is intended to keep migration of core materials to a minimum such that interaction with coating materials is reduced or prevented, whilst still allowing for release of the drug in an aqueous environment.

The stabilizing coating may thus be any suitable material which makes an inert barrier between the core (i.e. the active ingredient containing layer) and the modified release coating, and may be water soluble, water swellable, or water permeable polymeric or monomeric materials. Examples of such materials include, but are not limited to, hydroxypropylmethyl cellulose, hydroxypropyl cellulose, polyvinyl pyrrolidone, polyethylene glycol, or methacrylate based polymers (e.g. Eudragit® RS or Eudragit® RL).

In embodiments, the stabilizing coating includes a water-soluble polymer that does not interfere with the release of the active ingredient, and talc or another agent that performs the same function as talc. In various aspects, the water soluble polymer and talc may be present in the range of between 9 parts polymer to 1 part talc, through to 1 part polymer to 9 parts talc.

Controlled Release Coating

The controlled release coating may also be any suitable coating material, or combination of coating materials, that will provide the desired controlled release profile.

For example, coatings such as enteric coatings, semi-enteric coatings, delayed release coatings, or pulsed release coatings may be desired. In particular, a coating will be suitable if it provides an appropriate lag in active release prior to the rapid release at a rate essentially equivalent to immediate release of the active ingredient.

In particular, acid functional polymers such as hydroxypropylmethyl cellulose phthalate of varying grades (and also as an aqueous dispersion), methacrylate based polymers (e.g. Eudragit® L100-55 and Eudragit® L30D) and hydroxypropylmethyl cellulose acetate succinate, and other similar, pharmaceutically acceptable materials such as hydroxypropylmethyl cellulose acetate succinate, cellulose acetate succinate; cellulose acetate phthalate, hydroxypropylmethyl cellulose acetate succinate, cellulose acetate trimellitate, hydroxypropyl methyl cellulose phthalate, hydroxypropyl methyl cellulose acetate succinate, starch acetate phthalate, polyvinyl acetate phthalate, carboxymethyl cellulose, methyl cellulose phthalate, methyl cellulose succinate, methyl cellulose phthalate succinate, methyl cellulose phthalic acid half ester, and ethyl cellulose succinate.

It is also possible to use a mixture of enteric polymers to produce the modified release coating. It is also possible to use a mixture of enteric polymer with a water permeable, water swellable, or water-soluble material.

Suitable water-soluble or water permeable polymers include, but are not limited to, hydroxypropylmethyl cellulose, hydroxypropyl cellulose, polyvinyl pyrrolidone, polyethylene glycol, sodium alginate, and other similar, pharmaceutically acceptable materials, or mixtures thereof.

The controlled release coating may contain between 40% to 90% w/w enteric polymer. In some embodiments, the controlled release coating can also contain between 10% to 60% w/w water-soluble or water permeable polymers, based on the total weight of the controlled release coating. The controlled release coating may also contain 0% to 30% w/w of a plasticizer, based on the total weight of the controlled release coating.

In other embodiments, the controlled release coating contains about 80% to about 90% w/w of enteric polymer, optionally in combination with about 10% to about 20% w/w of a plasticizer. In particular embodiments, the controlled release coating contains about 84% w/w of enteric polymer, and optionally about 16% w/w of a plasticizer. In still other embodiments, the controlled release coating contains about 80% to about 90% w/w of enteric polymer and about 10% to about 20% w/w of water-soluble or water permeable polymer. In particular embodiments, the controlled release coating contains about 84% w/w of enteric polymer and about 16% w/w of water-soluble or water permeable polymer.

The "coating weight" of the controlled release coating refers to the amount of the coating, usually expressed as a weight percentage of the dried coating relative to the total weight of the pellet. The coating weight of the controlled release coating will vary depending on the delay desired and the polymer used, but generally will be between 5% w/w and 20% w/w.

The stabilizing coating and the controlled release coating may be applied to a core element in any suitable manner, such as by fluidized bed coating, including Würster coating, and rotacoating. In a particular aspect, both coatings will be applied by Würster coating.

Drying the pellet using any one of a number of drying techniques known in the art, such as oven drying or drying in a fluidized bed apparatus, may further improve stability.

Enteric Coatings

Controlled release preparations in accordance with the present disclosure will typically be such as to provide a delayed release of the active ingredient, with reference to the active ingredient's dissolution profile.

In this respect, where the controlled release is such as to provide a delayed release (generally referred to as a 'delayed release preparation') the composition is designed to slow the release of the active agent (e.g. doxycycline) in the stomach to minimize the side effects of the active agent that may be caused by its release in the stomach. Such side effects for tetracyclines, including doxycycline, include nausea and gastrointestinal irritation.

Most delayed release preparations aim for the drug to be released in the upper regions of the small intestines, for a number of reasons, as follows:

a) the drug is able to start working as soon as possible after ingestion without side effects caused by drug being released in the stomach;
b) the conditions in the upper small intestine may be optimum for drug absorption; and
c) to avoid acid degradation of the drug in the stomach.

By way of explanation, the stomach contents of healthy individuals who have eaten average meals usually have a residence time of 30 minutes to an hour and are at a pH usually in the range of 1.0 to 3.0. The stomach contents then move to the intestines where the pH usually ranges from 4.0 to 7.0, where a rapid release of the active ingredient is desired to allow rapid and complete absorption of the active ingredient. There may be release of the drug in the stomach after a lag period, if the residence time is longer or the stomach conditions are different from usual, but the release will be at a much slower rate than an immediate release preparation, so the high localized concentrations that cause nausea and irritation do not occur.

Therefore, in various embodiments, a delayed or controlled release profile exhibits minimal release of the active ingredient at the low pH levels characteristic of the stomach, over a period of approximately 60 minutes, but when exposed to a higher pH, e.g. at least about 4.5, essentially 100% of the active ingredient is released within about 60 minutes.

The release profiles of the compositions of the present invention differ from those of prior art compositions such as DORYX. At a pH of about 1.2, the compositions of the present invention exhibit minimal release of the drug (e.g., doxycycline), for example less than about 15% release after 60 minutes, whereas conventional compositions (such as DORYX) release essentially 100% of the drug under the same conditions after 60 minutes. As a result, the compositions of the present invention release substantially lower amounts of drug in the stomach of a patient (after ingestion), and thus reduce the incidence of undesirable side effects such as nausea and gastrointestinal irritation.

The release profile of the compositions of the present invention also differ from that of prior art compositions (e.g., DORYX) at the higher pH levels typical of the upper intestinal tract. For example, at pH 4.5, compositions of the present invention (e.g., comprising doxycycline as the active agent or drug) release less than about 5% of the drug after 30 minutes, about 10 to about 30% of the drug after 60 minutes, about 20 to about 50% of the drug after 90 minutes, about 30 to about 60% of the drug after 120 minutes, and about 50 to about 70% of the drug after 180 minutes. In contrast, comparable conventional compositions (e.g. DORYX) release about 50%, about 70%, about 80%, about 85%, and about 90% of the drug at the same time intervals.

By comparing in vivo pharmacokinetic data (e.g., Tables 5-7, below) with in vitro dissolution data at various pH values (e.g., FIGS. 8-11), the present inventors surprisingly discovered that dissolution rates measured in vitro at pH 5.0, in particular, qualitatively predict the relative rate and extent of absorption of various compositions according to the present invention (e.g., Pellet Formulation A and Pellet Formulation B) and known doxycycline formulations (e.g., Doryx). Since the drug loadings of the exemplary Pellet A and Pellet B doxycycline compositions (i.e., 90 mg) are different from that of the comparative DORYX tablet composition (i.e., 75 mg) in FIGS. 8-11, FIG. 12 provides a comparison of drug release as a function of mg doxycycline released. The rank order of release in vitro, for example at 20 minutes at pH 5.0 correlate well with the release observed in vivo.

Thus, without being bound to any particular theory, it is believed that the lack of an in vivo/in vitro relationship (IVIVR) at acidic media (e.g., up to and including pH 4.5) is consistent with little or no release of doxycycline from the compositions of the present invention in the stomach or upper small intestine (pH<~4.5), and therefore doxycycline is not available for absorption in the upper small intestine, a region of high drug absorption. Likewise, the observed IVIVR at pH 5.0 is consistent with absorption of doxycycline farther along the small intestine where a pH of approximately 5.0 would be expected. These observations are consistent with the slight decrease in absorption of doxycycline observed for the compositions of the present invention relative to conventional DORYX compositions.

At pH 5, compositions of the present invention (e.g., comprising doxycycline as the active agent) release about 45% to about 50% of the drug after 10 minutes, about 30% to about 40% (e.g., about 35-36%) of the drug at 15 minutes, about 55% to about 65% of the drug at 20 minutes, about 65 to about 70% of the drug at 30 minutes, about 70% to about 75% of the drug at 45 minutes, and about 75 to about 80% of the drug at 60 minutes. In contrast, comparable conventional compositions (e.g. Doryx) release about 40% of the drug at 10 minutes, about 70% of the drug in 20 minutes, about 90% of the drug at 30 minutes, and about 100% after about 45 minutes.

At pH 5.0, compositions of the present invention (e.g., comprising doxycycline as the active agent or drug) release less than about 48% of the drug in 15 minutes, less than about 64% of the drug at 20 minutes, less than about 72% of the drug at 25 minutes, less than about 85% of the drug at 30 minutes, and approximately 100% of the drug at about 60 minutes.

In other embodiments, at pH 5.0, compositions of the present invention release about 30% to about 48% of the drug in 15 minutes, about 30% to about 64% of the drug at 20 minutes, and about 45% to about 72% of the drug at 25 minutes.

In other embodiments, at pH 5.0, compositions the present invention release about 35% to about 48% of the drug in 15 minutes, about 40% to about 64% of the drug in 20 minutes, and about 50% to about 72% of the drug at 25 minutes.

In particular embodiments, the amount of drug released at 20 minutes at pH 5.0 by compositions of the present invention is in the range of 80-125% of about 38%, the amount of drug released at 25 minutes is in the range of 80-125% of about 54%, and the amount of drug released at 30 minutes is in the range of 80-125% of about 70% of the drug.

In other embodiments, at 15 minutes, the amount of drug released at pH 5.0 by the compositions of the present invention is less than 48%, includes about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, or about 48%, inclusive of all ranges and subranges therebetween.

In particular embodiments, the compositions of the present invention release about 36% of the doxycycline at 15 minutes, about 51% at 20 minutes, at about 65% at 25 minutes, all measured at pH 5.

In other embodiments, at 20 minutes, the amount of drug released at pH 5.0 by compositions of the present invention is less than about 64%, including about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, or about 64%, inclusive of all ranges and subranges there between. At 25 minutes, the amount of drug released at pH 5.0 is less than about 72%, including about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, or about 72%, inclusive of all ranges and subranges therebetween. At 30 minutes, the amount of drug released at pH 5.0 includes about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, or about 88%, inclusive of all ranges and subranges therebetween.

Alternatively, at pH 5.0 compositions of the present invention (e.g., comprising doxycycline as the active agent or drug), the amount of drug released at 20 minutes is in the range of 80-125% of about 52%, the amount of drug released at 25 minutes is in the range of 80-125% of about 65%, and the amount of drug released at 30 minutes is in the range of 80-125% of about 79% of the drug. In still other embodiments, the amount of drug released at pH 5.0 at 20 minutes includes about 41%, about 42%, about 43%, about 44%, about 45%, about 46%, about 4'7%, about 48%, about 49%, about 50%, about 51%, about 52%, about 53%, about 54%, about 55%, about 56%, about 5'7%, about 58%, about 59%, about 60%, about 61%, about 62%, about 63%, about 64%, or about 65%, inclusive of all ranges and subranges therebetween. At 25 minutes, the amount of drug released at pH 5.0 includes about 52%, about 53%, about 54%, about 55%, about 56%, about 5'7%, about 58%, about 59%, about 60%, about 61%, about 62%, about 63%, about 64%, about 65%, about 66%, about 6'7%, about 68%, about 69%, about 70%, about 71%, about 72%, about 73%, about 74%, about 75%, about 76%, about 77%, about 78%, about 79%, about 80%, about 81%, or about 82%, inclusive of all ranges and subranges therebetween. At 30 minutes, the amount of drug released at pH 5.0 includes about 63%, about 64%, about 65%, about 66%, about 6'7%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 8'7%, about 88%, about 89%, about 90%, about 91%, about 92%, about 93%, about 94%, about 95%, about 96%, about 97%, about 98%, or about 99%, inclusive of all ranges and subranges therebetween.

In various embodiments, the compositions of the present invention are dosage forms comprising doxycycline combined with a controlled release polymer composition, wherein the dosage form comprises 60, 90, or 120 mg of doxycycline, and at pH 5.0 the normalized average release of doxycycline is at least one of: less than about 48% at 15 minutes, less than about 64% at 20 minutes, and less than about 72% at 25 minutes.

In various embodiments, the compositions of the present invention are dosage forms comprising doxycycline combined with a controlled release polymer composition, wherein the dosage form comprises 60, 90, or 120 mg of doxycycline, and at pH 5.0 the normalized average release of doxycycline is at least one of: about 30% to about 48% at 15 minutes, about 30% about 64% at 20 minutes, and about 45% about 72% at 25 minutes.

In various embodiments, the compositions of the present invention are dosage forms comprising doxycycline combined with a controlled release polymer composition, wherein the dosage form comprises 60, 90, or 120 mg of doxycycline, and at pH 5.0 the normalized average release of doxycycline is at least one of: about 35% to about 48% at 15 minutes, about 40% about 64% at 20 minutes, and about 50% about 72% at 25 minutes.

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 15 minutes ranges from about 30% to about 48%.

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 15 minutes ranges from about 35% to about 48%.

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 15 minutes is about 34-38%

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 20 minutes ranges from about 42% to about 64%.

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 20 minutes ranges from about 47% to about 64%.

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 20 minutes is about 48-53%.

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 25 minutes ranges from about 58% to about 72%.

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 25 minutes ranges from about 65% to about 72%.

In other embodiments, the compositions of the present invention are dosage forms comprising doxycycline combined with the controlled release polymer composition wherein the dosage form comprises 60, 90, or 120 mg of doxycycline, and at pH 5.0, the normalized average release of doxycycline at 25 minutes is about 63-67%.

In various embodiments, when the amount of doxycycline of the dosage forms described herein is 60 mg, after administration of a single dose under fasting conditions to a patient in need thereof, the average $C_{max}$ is about 80% to about 125% of about 625-1600 ng/ml; or wherein when the amount of doxycycline of said dosage form is 90 mg, after administration of a single dose under fasting conditions to a patient in need thereof, the average $C_{max}$ is about 80% to about 125% of about 1100-2400 ng/ml; or wherein when the amount of doxycycline of said dosage form is 120 mg, after administration of a single dose under fasting conditions to a patient in need thereof, the average $C_{max}$ is about 80% to about 125% of about 1250-3200 ng/ml. In other embodiments, the average $C_{max}$ can be about 80% to about 125% of about 10 to about 27 ng/ml per mg of doxycycline administered.

In various embodiments, when the amount of doxycycline of the dosage forms described herein is 60 mg, after administration of a single dose to a patient in need thereof, the average $AUC_{0-\infty}$ is about 80% to about 125% of about 10000-24000 ng·hr/ml; or wherein when the amount of doxycycline of said dosage form is 90 mg, after administration of a single dose to a patient need thereof, the average $AUC_{0-\infty}$ is about 80% to about 125% of about 15000-36500 ng·hr/ml; or wherein when the amount of doxycycline of said dosage form is 120 mg, after administration of a single dose to a patient need thereof, the average $AUC_{0-\infty}$ is about 80% to about 125% of about 20000-48500 ng·hr/ml. In other embodiments, the average $AUC_{0-\infty}$ is about 80% to about 125% of about 167-404 ng·hr/ml per mg of doxycycline administered.

In contrast, comparable conventional compositions (e.g. DORYX) release about 53% of the drug at 15 minutes, about 64% % of the drug at 20 minutes, about 75% of the drug in 25 minutes, and about 86% of the drug at 30 minutes under the same conditions at pH 5.0.

In some embodiments, the percent release can be expressed as a "normalized" average release value, in which the average release is "normalized" to correct for differences in drug content of individual samples caused by manufacturing variability. Methods for determining "normalized" average release values are understood by one of skill in the pharmaceutical arts. For example, the normalizing factor can be calculated assuming that all drug is released at 90 minutes and in theory should be equal to 100% release. The normalization factor is equal to 100 divided by the measured value at 90 minutes. A normalized average release can then be calculated by multiplying all average release values by this factor to produce the normalized average release rate.

The lower levels of drug release (e.g., doxycycline) of the compositions of the present invention at pH of about 4.5 or 5 is indicative of the pH environment experienced by the drug formulation as it transitions from the pH levels of the stomach into the pH levels of the intestine. The compositions of the present invention show appreciably less release at these pH levels compared to conventional compositions, and therefore reduce nausea and gastrointestinal irritation in the patient. In particular, the lower release rates at the 'transitional' pH of about 4.5, compared to prior art formulations, ensures that the drug (e.g., doxycycline) will not release as it transits out of stomach, but that the release will be delayed until it is in the intestines, particularly the small intestine, more particularly, the upper small intestine, which is believed to contribute to reduced side effects.

In practice, it is difficult to prepare formulations that release no active ingredient at stomach pH levels, but provide complete release of the active ingredient at pH levels found in the upper intestinal tract. Accordingly, suitable formulations release less than about 15% of the active ingredient at a pH of about 1.2 after 60 minutes, and at least 90% of the active ingredient is released after 4-5 hours at a pH of at least 4.5 in in vitro tests such as USP <711>. In some embodiments, suitable formulations release less than about 10% of the active ingredient at a pH of about 1.2 after 60 minutes.

The ability of the compositions of the disclosure to release less than 10% of the active ingredient during the initial 60 minutes of exposure to low pH (e.g. pH of 1.0 to 3.0), or lower levels of release at pH 5.0 as described herein, is an improvement over conventional compositions, particularly conventional tetracycline compositions because it provides for lower levels of nausea and gastric irritation, while still providing sufficient exposure to the drug to provide the desired clinical effect. Conventional approaches to delay drug release in the stomach (e.g. adding thick enteric coatings or conventional controlled release coatings) may be useful in reducing release of the drug in the stomach, but can delay or retard absorption of the drug, thereby limiting its therapeutic benefits. The compositions of the present invention, however, provide minimal release of the drug in the stomach while maintaining high levels of clinical efficacy.

In one aspect of the invention, no more than 10% of the active ingredient is released at a pH of about 1.2 by 60 minutes and at least 80% of the active ingredient is released at a pH of at least 4.5 by about 5 hours when tested using USP <711> conditions.

In another aspect of the invention, no more than 10% of the active ingredient is released at a pH of about 1.2 by 60 minutes and at least 80% of the active ingredient is released at a pH of 5.0 by about 60 minutes when tested using USP <711> conditions.

In other embodiments, the compositions of the present invention have a release profile at a pH of about 1.2 (e.g., 0.06N HCl) when tested using USP <711> conditions, substantially identical to the curves labeled "Pellet A" or "Pellet B" of FIG. 1. In still other embodiments, the compositions of the present invention have a release profile at a pH of about 4.5 (phosphate buffer) when tested using USP <711> conditions, substantially identical to the curves labeled "Pellet A" or "Pellet B" of FIG. 2.

In other embodiments, the compositions of the present invention have a release profile at a pH of about 1.2 (e.g., 0.06N HCl) when tested using USP <711> conditions, substantially identical to the curves labeled "Pellet A" or "Pellet B" of FIG. 1. In still other embodiments, the compositions of the present invention have a release profile at a pH of about 5.0 (phosphate buffer) when tested using USP <711> conditions, substantially identical to the curves labeled "Capsule A" or "Capsule B" of FIG. 6.

For the purposes of in vitro testing, a release or dissolution profile may be determined at pH 1.2 using a 0.06 N hydrochloric acid solution, at pH 4.5 using a phosphate buffer using USP <711> test conditions, and at pH 5.0 using a buffer using USP <711> test conditions. Such test conditions can be carried out according to USP <711> dissolution conditions using Apparatus 1 (baskets) in 900 mL of media with stirring at 50 RPM.

The release profiles described above for the compositions of the present invention are preferred for some pharmaceutical active ingredients such as tetracycline antibiotics (e.g. doxycycline), or for any drug that can cause nausea or gastrointestinal irritation, but that has a narrow absorption window in the upper intestinal tract. For such drugs, it is preferable to limit release in the stomach, but to provide sufficient release within the narrow absorption window in the upper intestinal tract so as to provide clinically effective levels of the drug. In this manner, substantially identical exposure (i.e., AUC) can be provided by the compositions of the present invention relative to conventional formulations, which provides the desired clinical efficacy, but reduced release of the drug at low pH (i.e. in the stomach) reduces side effects such as nausea and gastrointestinal irritation.

For example, bisphosphonates are known to cause gastrointestinal ulceration at higher doses, opioid analgesics are known to cause nausea, and very basic drugs can be neutralized by the acidic conditions of the stomach, precipitate and not be absorbed. Additionally, other reactions may take place causing the activity of the drug to be lost.

Pharmaceutical Compositions

In certain embodiments, the pharmaceutical composition comprises the core containing the active therapeutic agent, a stabilizing coating, and a controlled release coating comprising an enteric polymer.

In other embodiments, the pharmaceutical composition comprises the core containing the active therapeutic agent, a stabilizing coating, a controlled release coating comprising an enteric polymer, and a pharmaceutically acceptable carrier.

Capsules Containing the Controlled Release Pellets

In particular embodiments, the pharmaceutical compositions of the present invention comprise a capsule, wherein said capsule contains a plurality of pellets each comprising: a core containing the active therapeutic agent, an optional stabilizing coating, and a controlled release coating comprising an enteric polymer as described herein.

In other embodiments, the controlled release pellet comprises a core containing doxycycline hyclate. In other embodiments, the controlled release pellet comprises a core containing the monohydrate form of doxycycline.

In embodiments, the capsule comprises a total amount of doxycycline hyclate of about 25 mg per capsule, or about 50 mg per capsule, or about 60 mg per capsule, or about 75 mg per capsule, or about 90 mg per capsule, or about 100 mg per capsule, or about 120 mg per capsule, or about 150 mg per capsule, or about 200 mg per capsule, or more. Unless indicated otherwise, the doses disclosed herein are expressed as the equivalent amount (e.g., mg) of doxycycline free base.

In embodiments, the capsule comprises a total amount of doxycycline hyclate of about 50 mg per capsule±about 10 mg, about 60 mg per capsule±about 10 mg, about 75 mg per capsule±about 10 mg, about 90 mg per capsule±about 10 mg, about 100 mg per capsule±about 10 mg, about 120 mg per capsule±about 10 mg, about 150 mg per capsule±about 10 mg, or about 200 mg per capsule±about 10 mg.

In embodiments, the capsule comprises a total amount of doxycycline hyclate of about 50 mg per capsule±about 5 mg, about 60 mg per capsule±about 5 mg, about 75 mg per capsule±about 5 mg, about 90 mg per capsule±about 5 mg, about 100 mg per capsule±about 5 mg, about 120 mg per capsule±about 5 mg, about 150 mg per capsule±about 5 mg, or about 200 mg per capsule±about 5 mg.

In embodiments, the capsule comprises a total amount of doxycycline hyclate of about 50 mg per capsule, about 60 mg per capsule, about 75 mg per capsule, about 90 mg per capsule, about 100 mg per capsule, about 120 mg per capsule, about 150 mg per capsule, or about 200 mg per capsule.

Tablets Containing the Controlled Release Pellets

In some embodiments, the pharmaceutical composition comprises a tablet, wherein said tablet contains at least one pellet comprising: a core containing the active therapeutic agent, an optional stabilizing coating, and a modified release coating comprising an enteric coating.

In embodiments, the controlled release pellet comprises a core containing doxycycline hyclate.

In embodiments, the tablet comprises a total amount of doxycycline hyclate of about 25 mg per tablet, about 50 mg per tablet, about 60 mg per tablet, about 75 mg per tablet, about 90 mg per tablet, about 100 mg per tablet, about 120 mg per tablet, about 150 mg per tablet, about 200 mg per tablet, or more.

In embodiments, the tablet comprises a total amount of doxycycline hyclate of about 50 mg per tablet±about 10 mg, about 60 mg per tablet±about 10 mg, about 75 mg per tablet±about 10 mg, about 90 mg per tablet±about 10 mg, about 100 mg per tablet±about 10 mg, about 120 mg per tablet±about 10 mg, about 150 mg per tablet±about 10 mg, or about 200 mg per tablet±about 10 mg.

In embodiments, the tablet comprises a total amount of doxycycline hyclate of about 50 mg per tablet±about 5 mg, about 60 mg per tablet±about 5 mg, about 75 mg per tablet±about 5 mg, about 90 mg per tablet±about 5 mg, about 100 mg per tablet±about 5 mg, about 120 mg per tablet±about 5 mg, about 150 mg per tablet±about 5 mg, or about 200 mg per tablet±about 5 mg.

In embodiments, the tablet comprises a total amount of doxycycline hyclate of about 50 mg per tablet, about 60 mg per tablet, about 75 mg per tablet, about 90 mg per tablet, about 100 mg per tablet, about 120 mg per tablet, about 150 mg per tablet, or about 200 mg per tablet.

Course of Treatment

The controlled release formulations comprising doxycycline can be utilized to treat acne in certain embodiments.

The controlled release pharmaceutical compositions comprising doxycycline may be administered once per day, twice per day, three times per day, or more, to a patient in need thereof. In some embodiments, the patient suffers from mild acne. In some embodiments, the patient suffers from severe acne.

In a particular embodiment, a patient suffering from acne is administered one capsule or tablet comprising controlled release doxycycline. In more particular embodiments, each controlled release pellet of the capsule comprises: a doxycycline-containing core, an optional stabilizing coating, and a controlled release coating. The tablet or capsule may comprise about 60 mg doxycycline, about 75 mg doxycycline, about 90 mg doxycycline, about 100 mg doxycycline, about 120 mg doxycycline, about 150 mg doxycycline, or about 200 mg doxycycline, and may be administered once or twice per day.

In particular embodiments, a patient is administered one tablet or capsule comprising about 60 or 120 mg doxycycline every 12 hours for the first 24 hours (i.e. total of 120 or 240 mg doxycycline in first 24 hours), which is followed by a maintenance dose of one tablet or capsule comprising about 120 mg doxycycline once daily. However, variations in this mode of treatment may be contemplated by physicians.

In embodiments, the adult dosage of oral doxycycline compositions, as taught herein, are to be administered in the amount of 240 mg on the first day of treatment (administered 120 mg every 12 hours), followed by a maintenance dose of 120 mg daily. The maintenance dose may be administered as a single dose or as 60 mg every 12 hours. In the management of more severe infections (particularly chronic infections of the urinary tract), 120 mg every 12 hours can be utilized.

In embodiments, the pediatric (above 8 years of age) dosage of oral doxycycline compositions, as taught herein, are to be administered according to a dosage schedule for children weighing 45 kg or less at 4.4 mg/kg of body weight divided into two doses on the first day of treatment, followed by 2.2 mg/kg of body weight given as a single daily dose or divided into two doses on subsequent days. For more severe infections up to 4.4 mg/kg of body weight may be used. For children over 45 kg, the usual adult dose may be used.

The compositions of the disclosure are active against at least the following organisms: (1) Gram-Negative Bacteria including: *Neisseria gonorrhoeae; Calymmatobacterium granulomatis; Haemophilus ducreyi; Haemophilus influenza; Yersinia pestis* (formerly *Pasteurella pestis*); *Francisella tularensis* (formerly *Pasteurella tularensis*); *Vibrio cholerae* (formerly *Vibrio comma*); *Bartonella bacilliformis; Brucella* species; Because many strains of the following groups of gram-negative microorganisms have been shown to be resistant to tetracyclines, culture and susceptibility testing are recommended: *Escherichia coli; Klebsiella* species; *Enterobacter aerogenes; Shigella* species; *Acinetobacter* species (formerly *Mima* species and *Herellea* species); (2) Gram-Positive Bacteria including: *Streptococcus pyogenes; Streptococcus pneumonia; Enterococcus* group (*Streptococcus faecalis* and *Streptococcus faecium*); and Alpha-hemolytic streptococci (*viridans* group) (because many strains of the aforementioned groups of gram-positive microorganisms have been shown to be resistant to tetracycline, culture and susceptibility testing are recommended, as up to 44 percent of strains of *Streptococcus pyogenes* and 74 percent of *Streptococcus faecalis* have been found to be resistant to tetracycline drugs, therefore, tetracycline should not be used for streptococcal disease unless the organism has been demonstrated to be susceptible); (3) Other Microorganisms including: Rickettsiae; *Chlamydia psittaci; Chlamydia trachomatis; Mycoplasma pneumonia; Ureaplasma urealyticum; Borrelia recurrentis; Treponema pallidum; Treponema pertenue; Clostridium* species; *Fusobacterium fusiforme; Actinomyces* species; *Bacillus anthracia; Propionibacterium acnes; Entamoeba* species; *Balantidium coli; Plasmodium falciparum*; Doxycycline has been found to be active against the asexual erythrocytic forms of; *Plasmodium falciparum* but not against the gametocytes of *P. falciparum*. The precise mechanism of action of the drug is not known.

Doxycycline is indicated for the treatment of the following infections: Rocky Mountain spotted fever, typhus fever and the typhus group, Q fever, rickettsialpox, and tick fevers caused by Rickettsiae; Respiratory tract infections caused by *Mycoplasma* pneumonia; Lymphogranuloma venereum caused by *Chlamydia trachomatis*; Psittacosis (ornithosis) caused by *Chlamydia psittaci*; Trachoma caused by *Chlamydia trachomatis*, although the infectious agent is not always eliminated as judged by immunofluorescence; Inclusion conjunctivitis caused by *Chlamydia trachomatis*; Uncomplicated urethral, endocervical or rectal infections in adults caused by *Chlamydia trachomatis*; Nongonococcal urethritis caused by *Ureaplasma urealyticum*; Relapsing fever due to *Borrelia recurrentis*. Chancroid caused by *Haemophilus ducreyi*; Plague due to *Yersinia pestis* (formerly *Pasteurella pestis*); Tularemia due to *Francisella* tularensis (formerly *Pasteurella tularensis*); Cholera caused by *Vibrio cholerae* (formerly *Vibrio comma*); *Campylobacter fetus* infections caused by *Campylobacter fetus* (formerly *Vibrio fetus*); Brucellosis due to *Brucella* species (in conjunction with streptomycin); Bartonellosis due to *Bartonella bacilliformis*; Granuloma inguinale caused by *Calymmatobacterium granulomatis*; Doxycycline is indicated for treatment of infections caused by the following gram negative microorganisms, when bacteriological testing indicates appropriate susceptibility to the drug: *Escherichia coli*; *Enterobacter aerogenes* (formerly *Aerobacter aerogenes*); *Shigella* species; *Acinetobacter* species (formerly *Mima* species and *Herellea* species); Respiratory tract infections caused by *Haemophilus* influenza; Respiratory tract and urinary tract infections caused by *Klebsiella* species; Doxycycline is indicated for treatment of infections caused by the following gram positive microorganisms when bacteriological testing indicates appropriate susceptibility to the drug: Upper respiratory infections caused by *Streptococcus pneumoniae* (formerly *Diplococcus Pneumoniae*); Anthrax due to *Bacillus anthracis*, including inhalational anthrax (post-exposure): to reduce the incidence or progression of disease following exposure to aerosolized *Bacillus anthracis*; When penicillin is contraindicated, doxycycline is an alternative drug in the treatment of the following infections: Uncomplicated gonorrhea caused by *Neisseria gonorrhoeae*; Syphilis caused by *Treponema pallidum*; Yaws caused by *Treponema pertenue*; Listeriosis due to *Listeria monocytogenes*; Vincent's infection caused by *Fusobacterium fusiforme*; Actinomycosis caused by *Actinomyces israelii*; Infections caused by *Clostridium* species; In acute intestinal amebiasis, doxycycline may be a useful adjunct to amebicides; In severe acne, doxycycline may be useful adjunctive therapy; Prophylaxis: Doxycycline is indicated for the prophylaxis of malaria due to *Plasmodium falciparum* in short-term travelers (<4 months) to areas with chloroquine and/or pyrimethaminesulfadoxine resistant strains.

The following non-limiting Examples illustrate certain aspects of the present disclosure.

EXAMPLES

Example 1: Preparation of Controlled Release Doxycycline Hyclate Pellets

Core Preparation

The core is formed in a wet granulation process using a saturated solution of sodium chloride and in a high shear mixer.

The mixture is then extruded using a screen size of between 0.4 and 1.5 mm. The extrudate is then spheronized to produce rounded core elements. The core elements are dried in a fluidized bed or an oven.

Stabilizing Coat Application

A stabilizing coat is applied to the core using a fluidized bed coating process.

The stabilizing coat contains hydroxypropylmethyl cellulose and talc in a 2:1 mixture.

The desired polymer coat weight (i.e. the weight of the polymer only, not including the talc) is between 3% and 5% of the total weight of the core element and the stabilizing coat.

The polymer coat weight will vary due to a number of factors, such as the efficiency of the coating process, the batch of raw materials, etc.

Modified Release Coat Application

The modified release coating is applied to the stabilizing coated core using a fluidized bed coating process to form pellets.

The desired polymer coat weight is 15% of the total weight of the pellet.

Table 1, below, provides examples of two controlled release doxycycline hyclate formulations derived according to the above procedure. Table 1 also provides the formulation components for a commercially available doxycycline hyclate formulation (DORYX) for comparison.

TABLE 1

Formulation of a Modified Release Coating Layer of a Controlled Release Doxycycline Pellet

| Wt. % in modified release coating | DORYX 75 mg Pellet | Pellet Formulation A | Pellet Formulation B |
|---|---|---|---|
| HP 50 (hydroxyl propyl methyl cellulose phthalate) | 67 | 84 | 84 |
| HPMC (hydroxyl propyl methyl cellulose | 16 | 16 | 0 |
| TEC (tri ethyl citrate) | 17 | 0 | 16 |
| Theoretical Polymer coat weight as % of total weight of the pellet | 15 | 28 | 11 |

The in vitro release of the pellets was tested using USP XXIV 2000—Apparatus 1 (baskets). See, e.g., Riaz Uddin, Nadia Saffoon, and Kumar Bishwajit Sutradhar, "Dissolution and Dissolution Apparatus: A Review," Int. J. Cur. Biomed. Phar. Res., 2011, Vol. 1(4), pgs. 201-207.

The dissolution profiles of the formulations are contained below.

The aforementioned pellet formulations of doxycycline hyclate can be packed into capsules and also formulated as tablets. In the following dissolution experiments, the pellets were loaded into capsules.

Example 2: Dissolution Profiles of Control (DORYX), Pellet a Formulation, & Pellet B Formulation Acidic Dissolution Profile The acid environment dissolution profile of pellet A and B's formulation can be seen in FIG. 1.

As can be seen in FIG. 1, the formulations of pellet A and B release less than 10% of the doxycycline hyclate in an acid environment (pH of approximately 1.2) after 60 minutes of exposure under standard USP conditions.

The slow rate of release of doxycycline, in a pH of approximately 1.2, exhibited by the pellet formulations according to the disclosure is in stark contrast to the dissolution profile of the commercially available DORYX.

As can be seen in FIG. 1, the DORYX tablet released approximately 98%-100% of the doxycycline hyclate at 60 minutes.

Thus, the controlled release doxycycline formulations of the disclosure exhibit a beneficial and superior dissolution profile in acidic conditions, as compared to a commercially available doxycycline formulation.

Elevated pH Dissolution Profile

Figure 2:
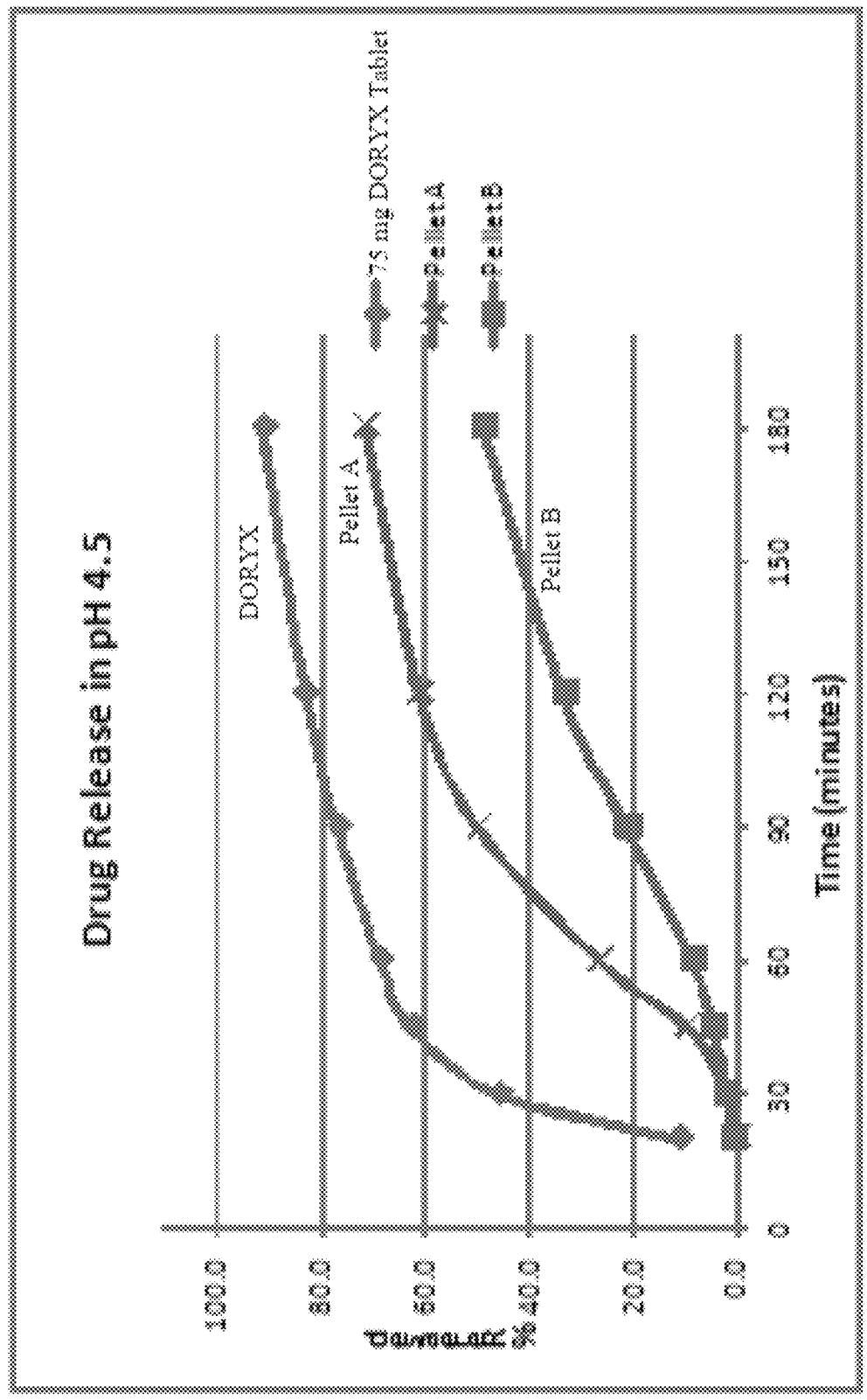
FIG. 2 is a graph illustrating the dissolution profile in pH 4.5 buffered media of a controlled release pellet formulation (A or B) of the disclosure compared to a control DORYX tablet.

The dissolution profile of pellet A and B formulations at elevated pH can be seen in FIG. 2.

As can be seen in FIG. 2, the formulation of pellet A releases greater than about 25% of the doxycycline hyclate in a basic environment (pH of approximately 4.5) after 60 minutes of exposure under standard USP conditions.

Also, as can be seen in FIG. 2, the formulation of pellet B releases less than about 10% of the doxycycline hyclate in a basic environment (pH of approximately 4.5) after 60 minutes of exposure under standard USP conditions. Thus, the formulation of pellet B releases less than 10% of active ingredient in both an acidic and basic environment at 60 minutes.

The slow rate of release of doxycycline, in a pH of approximately 4.5, exhibited by the pellet formulations according to the disclosure is in stark contrast to the dissolution profile of the commercially available DORYX.

As can be seen in FIG. 2, the DORYX tablet released approximately 70% of the doxycycline hyclate at 60 minutes in a pH of 4.5.

Thus, the controlled release doxycycline formulations of the disclosure exhibit a beneficial and superior dissolution profile in basic conditions, as compared to a commercially available doxycycline formulation.

Example 3: Clinical Data

The aforementioned controlled release pellet formulations (A and B) were loaded into capsules and administered to 10 test subjects to obtain in vivo data.

It is also contemplated that pellet formulations A and B may be formulated into tablets.

After all 10 completed subjects were analyzed; the following Geometric Mean Ratio (GMR) and Intra-Subject Coefficient of Variation (CV) were obtained for the two Test Formulations.

TABLE 2

In Vitro Pharmacokinetics Data

| Formulation | Parameter | GMR (%) | CV (%) |
|---|---|---|---|
| Pellet A | $AUC_{0-\infty}$ | 89.64 | 17.24 |
|  | $AUC_{0-t}$ | 89.58 | 17.71 |
|  | $C_{max}$ | 88.08 | 19.87 |
| Pellet B | $AUC_{0-\infty}$ | 106.90 | 17.24 |
|  | $AUC_{0-t}$ | 106.37 | 17.71 |
|  | $C_{max}$ | 103.73 | 19.87 |

Figure 3:
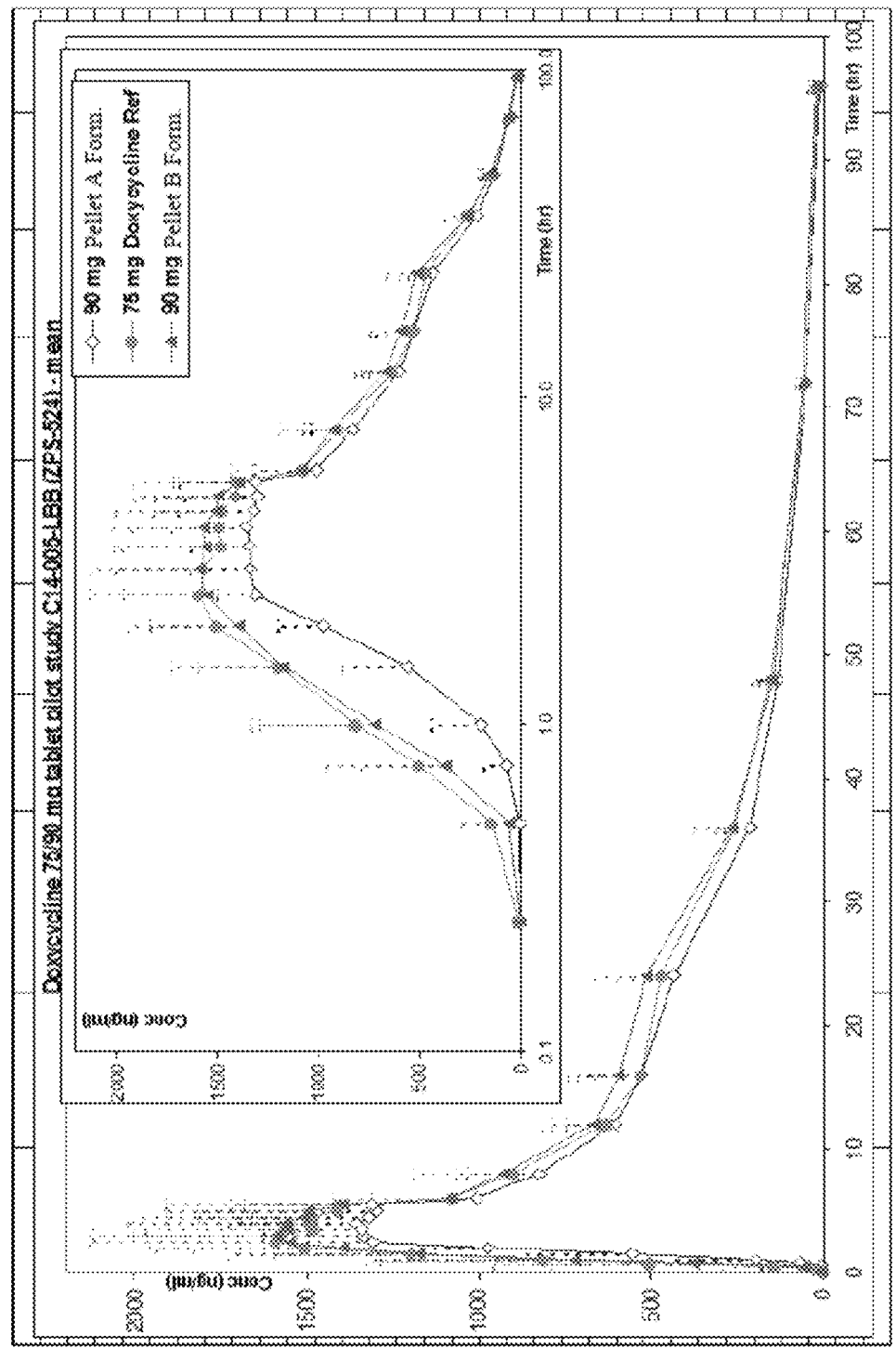
FIG. 3 is a graph of the mean concentration of doxycycline present in the plasma of subjects treated with a capsule comprising controlled release doxycycline pellet formulations (A or B) compared to a control doxycycline formulation.
Figure 4:
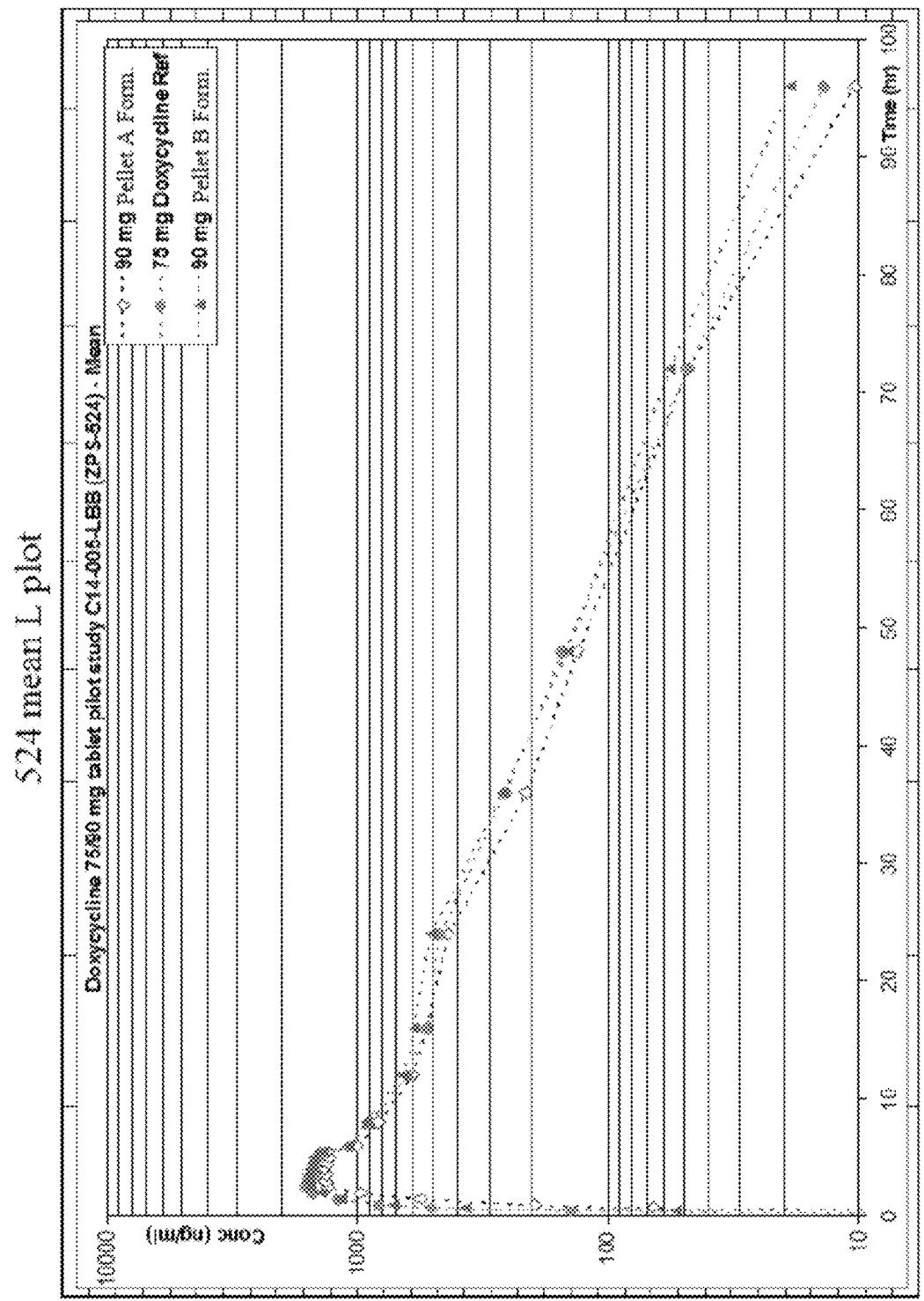
FIG. 4 is a graph of the mean logarithmic concentration of doxycycline present in the plasma of subjects treated with a capsule comprising controlled release doxycycline pellet formulations (A or B) compared to a control doxycycline formulation.

Further, FIG. 3 and FIG. 4 illustrate the concentration of active substance in ng/mL of the two tested pellet A and pellet B formulations as compared to a doxycycline (DORYX) control.

As shown in FIG. 3, 90 mg controlled release pellet formulations (A and B) of the present invention have average $AUC_{0-t}$ values (ng·hr/ml) which differ from that of conventional 75 mg doxycycline formulations (e.g., DORYX) during the initial two to three hours after administration. However, $AUC_{0-\infty}$ values for these compositions are essentially identical (i.e., bioequivalent) to that of the conventional DORYX composition. $AUC_{0-t}$ values at various time points for pellets A and B, compared to DORYX are shown below in Table 3.

TABLE 3

$AUC_{0-t}$ vs. TIME

| Time post administration (hours) | $AUC_{0-t}$ Doryx | $AUC_{0-t}$ Pellet A | $AUC_{0-t}$ Pellet B |
|---|---|---|---|
| 0.25 | 1 | 0 | 0 |
| 0.5 | 19 | 1 | 6 |
| 0.75 | 100 | 9 | 55 |
| 1 | 271 | 42 | 179 |
| 1.5 | 781 | 235 | 616 |
| 2 | 1,448 | 614 | 1,220 |
| 2.5 | 2,202 | 1,181 | 1,912 |
| 3 | 2,965 | 1,843 | 2,665 |
| 3.5 | 3,719 | 2,513 | 3,437 |
| 4 | 4,436 | 3,188 | 4,184 |
| 4.5 | 5,153 | 3,858 | 4,946 |
| 5 | 5,856 | 4,513 | 5,696 |
| 5.5 | 6,539 | 5,166 | 6,416 |
| 6 | 7,142 | 5,746 | 7,015 |
| 8 | 9,063 | 7,581 | 9,008 |
| 12 | 12,039 | 10,440 | 12,168 |
| 16 | 14,304 | 12,700 | 14,683 |
| 24 | 18,202 | 16,578 | 19,086 |
| 36 | 21,963 | 20,128 | 23,147 |
| 48 | 24,775 | 22,468 | 26,110 |
| 72 | 27,160 | 24,678 | 28,650 |
| 96 | 27,748 | 25,137 | 29,369 |

A larger follow-up study is being conducted. The following sample sizes, in Table 3, are required based on the above GMR and CV.

TABLE 4

Sample Size of Follow-up Pharmacokinetic Study

| Formulation | Parameter | Sample Size |
|---|---|---|
| Pellet A | $AUC_{0-\infty}$ | 30 |
|  | $AUC_{0-t}$ | 32 |
|  | Cmax | 56 |
| Pellet B | $AUC_{0-\infty}$ | 18 |
|  | $AUC_{0-t}$ | 18 |
|  | Cmax | 16 |

Example 4: Preparation of Controlled Release Doxycycline Monohydrate Pellets

Doxycycline is can be prepared as the hyclate salt, as described above. However, the monohydrate form of doxycycline is also available.

Currently, the monohydrate form of doxycycline is only commercially available as an immediate release form.

The monohydrate form of doxycycline may be safer to use than the hyclate salt, and hence a delayed release formulation of this product would provide meaningful benefits for patients.

However, doxycycline monohydrate does not behave in the same way as the hyclate product and presents challenges in formulation.

The present disclosure provides a controlled release formulation of doxycycline monohydrate, by providing a standard core that comprises the doxycycline monohydrate that is coated with the modified released coating as described herein.

Further modified release coating formulations are contemplated by the disclosure to achieve various dissolution profiles for the controlled release doxycycline monohydrate product.

Figure 5:
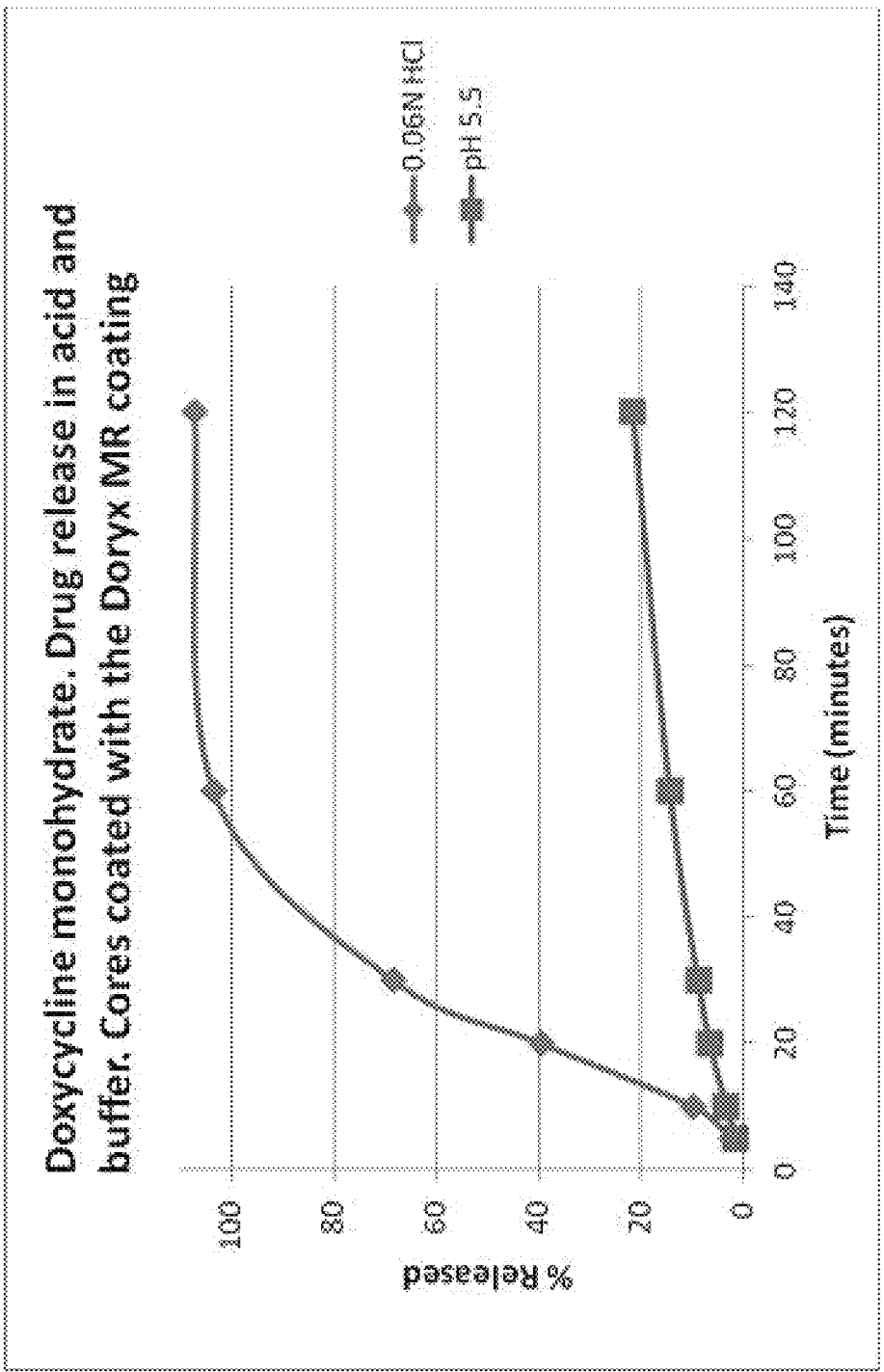
FIG. 5 is graph of an embodiment of the invention comprising doxycycline monohydrate salt, demonstrating that said embodiment is very soluble at lower pH values and releases readily under acidic conditions, but is not very soluble at pH values above 3, leading to low release rates overall.
Figure 6:
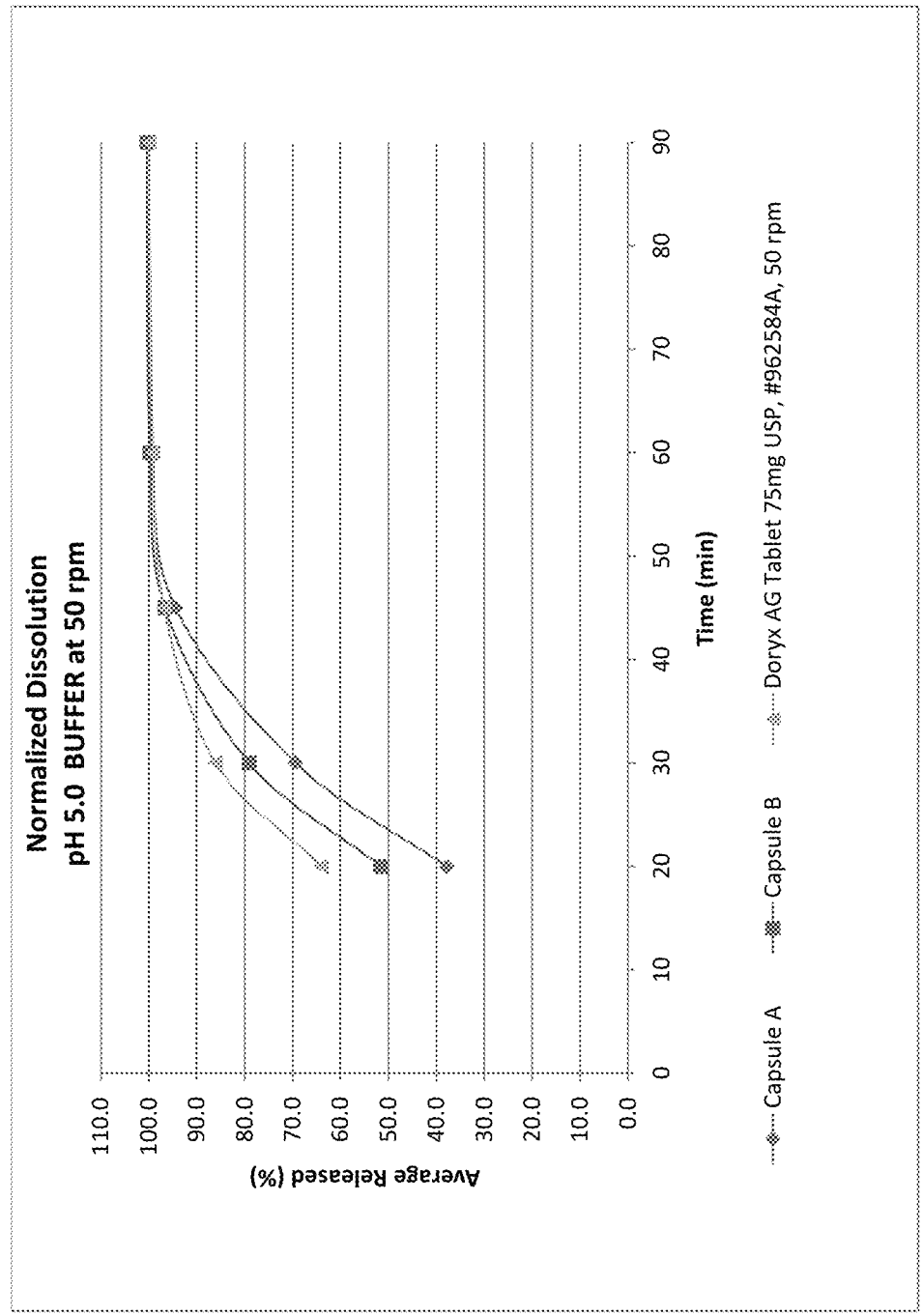
FIG. 6 is a graph illustrating the dissolution profile at pH 5.0 of a controlled release pellet formulation (A or B, 90 mg doxycycline) of the disclosure compared to a control 75 mg DORYX tablet.

A shown in FIG. 5, the monohydrate salt is very soluble at lower pH's and releases readily in acid, but is not very soluble at pH above 3, leading to low release rates overall.

Example 5: Pharmacokinetic Study

An in-vivo pharmacokinetic study (n=12 healthy subjects, study protocol no. ZPS-524)) was conducted to evaluate the MP336 90 mg DR Capsule A and MP336 90 mg DR Capsule B formulations against a reference product, Doxycycline Hyclate Delayed Release Tablets USP, 75 mg ex Mayne Pharma. The tablets are an authorized generic of Doryx™ Delayed Release Tablets 75 mg. Results of the study are summarized below in Table 5, Table 6, Table 7 and FIG. 3 (inset).

TABLE 5

Pharmacokinetic Results from a n = 12 Study of 90 mg DR Capsules A DR Capsules B (lot 990904) and Doxycycline Hyclate DR Tablet USP, 75 mg

| Pharmacokinetic Parameters | 1 × 90 mg DR Capsules A (n = 11) Mean ± S.D. (range) | 1 × 90 mg DR Capsules B (n = 11) Mean ± S.D. (range) | 1 × 75 mg Doxycycline hyclate DR Tablet (n = 11) Mean ± S.D. (range) |
|---|---|---|---|
| $AUC_{0-\infty}$ (ng · hr/ml) | 25857.8 ± 5866.6 (17819.3-36377.0) | 30545.6 ± 5789.5 (21066.3-37567.2) | 29027.8 ± 7015.4 (15172.7-36423.4) |
| $AUC_{0-t}$ (ng · hr/ml) | 25137.4 ± 5837.7 (17177.9-35715.2) | 29548.4 ± 5638.9 (20073.5-35985.0) | 28285.3 ± 6994.3 (14138.5-34870.2) |
| c (ng/ml) | 1548.7 ± 320.8 (942.7-2070.4) | 1818.0 ± 344.5 (1158.8-2416.7) | 1775.0 ± 433.8 (995.0-2341.2) |
| $T_{max}$ (hr) | 3.60 ± 1.07 (2.50-5.50) | 3.05 ± 1.17 (1.50-5.00) | 2.60 ± 0.91 (1.00-4.50) |
| $t_{1/2}$ (hr) | 16.13 ± 2.85 (13.80-23.33) | 17.60 ± 4.94 (11.60-27.78) | 16.09 ± 3.71 (12.38-23.30) |

TABLE 6

Statistical Comparison of 90 mg DR Capsules A, and Doxycycline Hyclate DR Tablet USP, 75 mg
Test 1: 1 × 90 mg DR Capsule A vs
Reference: 1 × 75 mg Doxycycline Hyclate DR Tablet

|  | Anova[a] | Geometric mean ratio[a] | 90% confidence interval[a] |
|---|---|---|---|
| $AUC_{0-\infty}$ | 0.102 | 89.96 | (79.49, 103.76)* |
| $AUC_{0-t}$ | 0.124 | 89.88 | (79.18, 104.04) |
| $C_{max}$ | 0.181 | 88.08 | (75.98, 103.31)* |

[a]Results obtained from log-transformed data
*Criteria used to assess Bioequivalence i.e. 90% CI between 80.00% and 125.00% for $AUC_{0-\infty}$ and $C_{max}$

TABLE 7

Statistical Comparison of 90 mg DR Capsules B, and Doxycycline Hyclate DR Tablet USP, 75 mg
Test 1: 1 × 90 mg DR Capsule A vs
Reference: 1 × 75 mg Doxycycline Hyclate DR Tablet

|  | Anova[a] | Geometric mean ratio[a] | 90% confidence interval[a] |
|---|---|---|---|
| $AUC_{0-\infty}$ | 0.102 | 106.86 | (94.81, 123.75)* |
| $AUC_{0-t}$ | 0.124 | 106.30 | (93.98, 123.49) |
| $C_{max}$ | 0.181 | 103.73 | (89.80, 122.10)* |

[a]Results obtained from log-transformed data
*Criteria used to assess Bioequivalence i.e. 90% CI between 80.00% and 125.00% for $AUC_{0-\infty}$ and $C_{max}$ Example 6: A Randomized, Laboratory-Blinded, Single Dose, Two-Period, Crossover Food Effect Bioavailability Study of Doxycycline 120 mg Delayed-Release Tablets in Healthy Male and Female Volunteers A study was carried out to evaluate and compare the bioavailability under fasting and fed conditions of a 120-mg delayed-release formulation of doxycycline according to the present disclosure after a single oral dose administration. The secondary objective of this study was to determine the safety and tolerability of the doxycycline composition according to the present disclosure in healthy volunteers under fasting and fed conditions.

The study was designed as a single center, randomized, single dose, laboratory-blinded, 2-treatment (fed vs. fasting), 2-period, 2-sequence, crossover study. 28 subjects were included in the study, of which one subject was included only in the analysis of $C_{max}$ and $T_{max}$. Subjects of the study were male or postmenopausal or surgically sterile female, at least 18 years of age, who are light-, non- or ex-smokers and have a body mass index (BMI)≥18.0 kg/m² and <32.0 kg/m² and no clinically significant abnormality found in a 12-lead ECG performed at study entry.

The treatment regimen was a single dose of 120 mg (each tablet contains 120 mg of doxycycline for oral administration). A single 120 mg oral dose of doxycycline was administered under fed (Treatment-1) and fasting (Treatment-2) conditions in each study period. The drug administrations were separated by a wash-out of 14 calendar days.

In each study period, 19 blood samples were collected. The first blood sample was collected prior to drug administration while the others were collected up to 96 hours after drug administration.

Mathematical Model and Statistical Methods of Pharmacokinetic Parameters

The main absorption and disposition parameters were calculated using a non-compartmental approach with a log-linear terminal phase assumption. The trapezoidal rule was used to estimate area under the curve. The terminal phase estimation was based on maximizing the coefficient of determination. The pharmacokinetic parameters of this trial were $C_{max}$, $T_{max}$, $AUC_{0-T}$, $AUC_{0-\infty}$, $AUC_{0-T/\infty}$, $\lambda_Z$ and $T_{half}$.

The statistical analysis was based on a parametric ANOVA model of the pharmacokinetic parameters; the two-sided 90% confidence interval of the ratio of geometric means for the $C_{max}$, $AUC_{0-T}$ and $AUC_{0-\infty}$ was based on ln-transformed data; $T_{max}$ was based on a non-parametric approach.

An absence of food-effect on bioavailability of doxycycline was determined if the ratio of geometric LSmeans with corresponding 90% confidence interval calculated from the exponential of the difference between Treatment-1 (Fed) and Treatment-2 (Fast) for the ln-transformed parameters $C_{max}$, $AUC_{0-T}$ and $AUC_{0-\infty}$ are within the 80.00 to 125.00% range.

The results of this study indicate that food reduced significantly the rate of absorption of doxycycline ($C_{max}$) linked to a delayed $T_{max}$ as shown in the PK analysis. However, although the extent of absorption (AUC) was reduced by about 10% under fed conditions, food intake was judged not to have a clinical influence on this parameter. In fact, the pharmacokinetic results demonstrate that the $C_{max}$ geometric LSmeans value under fed conditions was approximately 71% of the value obtained under fasting conditions (corresponding 90% confidence intervals was 64.62% to 77.73%). Also, the median time to peak plasma concentration of doxycycline was delayed from 3.25 hours to 4.00 hours. The geometric LSmean ratios of $AUC_{0-T}$ and $AUC_{0-\infty}$ of doxycycline were 89.88% and 90.20%, respectively, with the corresponding 90% confidence intervals included within the range of 80.00% to 125.00%. The mean terminal elimination half-life ($T_{half}$) was also comparable in both conditions.

The results from measured data based on 28 subjects are presented in the summary Tables 8 and 9.

TABLE 8

Pharmacokinetic Parameters of Doxycycline

| PARAMETER | Treatment-1 (Fed) (n = 28) | | Treatment-2 (Fast) (n = 28) | |
|---|---|---|---|---|
| | MEAN | C.V. (%) | MEAN | C.V. (%) |
| $C_{max}$ (ng/mL) | 1042.3 | (31.2) | 1484.8 | (34.1) |
| ln ($C_{max}$) | 6.9029 | (4.5) | 7.2472 | (4.7) |
| $T_{max}$ (hours) $^a$ | 4.00 | (1.00-6.00) | 3.25 | (1.50-4.00) |
| $AUC_{0-T}$ (ng · h/mL)** | 23420.5 | (28.5) | 25959.2 | (28.7) |
| ln ($AUC_{0-T}$)** | 10.0196 | (3.0) | 10.1259 | (2.8) |
| $AUC_{0-\infty}$ (ng · h/mL)** | 24073.6 | (28.5) | 26637.5 | (29.5) |
| ln ($AUC_{0-\infty}$)** | 10.0474 | (3.0) | 10.1501 | (2.8) |
| $AUC_{0-T/\infty}$ (%)** | 97.27 | (1.4) | 97.62 | (1.3) |
| $\lambda_Z$ (hours$^{-1}$)** | 0.0410 | (15.1) | 0.0397 | (15.7) |
| $T_{half}$ (hours)** | 17.31 | (16.8) | 17.88 | (15.9) |

$^a$ median and range are presented
**n = 27

The AEs in this study were reported with a low incidence. Dizziness, rhinorrhea, and fatigue were each experienced by 1 subject (4%) after administration of only Treatment-1 while headache, nasal congestion, abdominal discomfort, and peripheral vascular disorder were each experienced by 1 subject (4%) after administration of only Treatment-2.

Subjects dosed with Treatment-2 (under fasting conditions) reported AEs with a higher incidence compared to Treatment-1 (7% Treatment-1 and 14% Treatment-2). However, the incidence of AEs was low for both treatments. Drug-related AEs were only reported for subjects dosed with Treatment-2 (4%). The AEs experienced during the study were deemed mild (5/7, 71%), moderate (1/7, 14%) and severe (1/7, 14%) in intensity. Following the administration of Treatment-2 in period 2, subject 003 experienced a severe SAE peripheral vascular disorder that was judged serious, unexpected and not possibly related (no reasonable possibility as per protocol) by the investigator. This severe SAE was resolved with sequelae.

Generally, the subjects showed laboratory values within normal range in both treatment groups, all vital signs were judged normal or not clinically significant, and all physical examinations were judged normal.

The objective of this study was to determine the influence of food on the pharmacokinetic profile of a new tablet formulation of doxycycline. The mean $C_{max}$, $AUC_{0-T}$ and $AUC_{0-\infty}$ of doxycycline was reduced by approximately 30%, 10% and 10%, respectively, following a single dose administration of 120 mg delayed-release tablets with a high-fat, high-calorie meal compared to fasting conditions. The median time to peak plasma concentration of doxycycline was delayed by approximately 45 minutes under fed conditions compared to fasting conditions.

The geometric LSmeans ratio and corresponding 90% confidence intervals for $C_{max}$ were below 80.00%, but were within the range of 80.00% to 125.00% for $AUC_{0-T}$ and $AUC_{0-\infty}$.

Based on this study, food seems to decrease the rate of absorption of doxycycline from the Test product (120 mg delayed-release tablets) without showing a clinical influence on its extent of absorption.

Overall, the drug tested was generally safe and well tolerated by the subjects included in this study. One SAE (peripheral vascular disorder of severe intensity) was reported during this study; however, this event was judged unexpected and not possibly related to the administration of MP336 under fasting conditions.

TABLE 9

Pharmacokinetic Parameters of Doxycycline

| PARAMETER | INTRA-SUBJECT C.V. (%) | GEOMETRIC LSMEANS* | | RATIO (%) | 90% CONFIDENCE LIMITS (%) | |
|---|---|---|---|---|---|---|
| | | Treatment-1 (Fed) (n = 28) | Treatment-2 (Fast) (n = 28) | | LOWER | UPPER |
| $C_{max}$ | 20.5 | 995.2 | 1404.1 | 70.87 | 64.62 | 77.73 |
| $AUC_{0-T}$** | 13.5 | 22472.9 | 25004.2 | 89.88 | 84.42 | 95.68 |
| $AUC_{0-\infty}$** | 13.3 | 23103.9 | 25613.4 | 90.20 | 84.81 | 95.94 |

*units are ng/mL for $C_{max}$ and ng · h/mL for $AUC_{0-T}$ and $AUC_{0-\infty}$
**n = 27

Example 7: A Study to Evaluate the Relative Bioavailability of a Test Formulation of Doxycycline Hyclate Delayed-Release Tablets, 120 mg Compared to Doxycycline Hyclate Delayed-Release Tablets USP, 100 mg in Healthy Adult Subjects Under Fasted Conditions The objective of this study was to evaluate the relative bioavailability of a test formulation of doxycycline hyclate 120 mg DR Tablet compared to the marketed reference product, doxycycline hyclate delayed-release tablets, USP 100 mg, in healthy adult male and female subjects under fasted conditions.

7.1 Study Design and Plan Description

This was an open-label, randomized, single-dose, two-period, two-treatment, two-sequence, crossover study under fasted conditions comparing the test and reference products. In each period of the study, a single doxycycline hyclate delayed-release tablet (100 mg or 120 mg) was administered to subjects following an overnight fast of at least 10 hours. Subjects received the test product in one of the study periods and the reference product in the other study period according to a two-sequence randomization schedule. Blood samples were collected pre-dose and at intervals over 96 hours after dosing in each study period. Subjects were confined at the clinical facility from at least 10 hours before dosing until after the 24-hour blood sample collection in each study period and returned to the clinical facility for blood sample collections at 36, 48, 72, and 96 hours after dosing. The interval between doses was 14 days.

The plasma concentrations of doxycycline were measured by a fully validated analytical procedure. Statistical analysis using average equivalence methodology was performed to evaluate the relative bioavailability of the test formulation to that of the reference product.

The study enrolled 28 healthy adult subjects. No additional subjects were enrolled after study commencement. Samples from all subjects who completed both periods of the study were analyzed.

7.2 Selection of Study Design

This study was designed based on the known pharmacokinetics of doxycycline hyclate delayed-release tablets, USP and generally accepted standards for the conduct of bioequivalence/bioavailability studies under fasted conditions. To minimize any possibility of a carry-over effect, a washout period of 14 days was selected for this study based on a reported T½ of approximately 18 hours for doxycycline.

7.3 Treatments Administered

The subjects received the test (1×120 mg doxycycline hyclate delayed-release tablet) and reference (1×100 mg doxycycline hyclate delayed-release tablet) treatments according to a two-treatment, two-sequence randomization schedule under direct observation following an overnight fast of at least 10 hours. Each dose was administered with 240 mL of room temperature water. The test product was MP336 120 mg DR Tablet (manufactured by Mayne Pharma International Pty. Ltd.) and the reference product was doxycycline hyclate delayed-release tablets, USP 100 mg (manufactured by: Mayne Pharma International Pty. Ltd.; distributed by: Midlothian Laboratories). The subjects received the test formulation in one of the study periods and the reference formulation in the other period. There was a 14 day interval between treatments.

7.4 Drug Concentration Measurements

The comparison of the pharmacokinetic parameters of the test and reference products is the generally accepted methodology for determining relative bioavailability. Physical examination, adverse event solicitation, vital sign assessment, and clinical laboratory testing are typical safety measures in this type of study.

In each period, the subjects reported for check-in (Day −1) at least 10 hours before dosing. A meal was provided on check-in Day −1 and consumed at least 10 hours before dosing. No food or beverages (except water) were permitted after the fasting period began on Day −1. All subjects fasted (except for water) for at least 10 hours before dosing.

During confinement following dosing (Day 1 to Day 2), standardized, caffeine-, xanthine-, alcohol-, and grapefruit-free meals and snacks were served at standard meal times after dosing. The same meal schedule and menu were used for each confinement period. When meals and blood sample collections coincided, samples were collected before meals were served. The subjects were released from the clinical facility about 24 hours after dosing in each study period and returned to the clinical facility for blood sample collections at 36, 48, 72, and 96 hours after dosing. A 14 day interval separated the dosings.

Subjects were instructed to abstain from alcohol, caffeine, xanthine or grapefruit-containing food or beverages or energy drinks within 48 hours before dosing in each period and throughout the times of sample collection in each period. No subjects reported consuming a restricted substance within the time frames indicated.

During the confinement periods of the study, fluid was restricted from one hour before dosing until one hour after dosing with the exception of the water (240 mL) administered with the dose. Water was encouraged ad lib at all other times. No fluids other than water and those served with meals were permitted during confinement.

Subjects were required to remain sitting upright for the first 4 hours post-dose except as required for study procedures. Subjects who experienced dizziness or lightheadedness may have been allowed to lie down at the discretion of the Investigator. No strenuous activity was permitted during confinement.

Subjects were instructed to take care to minimize exposure to natural or artificial sunlight (e.g., tanning beds) during the study and for at least 4 days after the last study visit. The use of tobacco was prohibited from at least 1 hour before dosing until at least 4 hours after dosing and for 30 minutes before scheduled vital sign measurements.

In each period, 6 mL venous blood was collected in chilled sodium heparin vacutainers up to 60 minutes before dosing and at the following nominal times after dosing: 0.5, 1.0, 1.5, 2.0, 2.33, 2.67, 3.0, 3.33, 3.67, 4.0, 4.5, 5.0, 6.0, 8.0, 12.0, 16.0, 24.0, 36.0*, 48.0*, 72.0*, and 96.0* hours (*return sample). At the time of collection, samples were labeled with a unique code number. After collection, the whole blood samples were gently inverted several times to ensure proper mixing with the anticoagulant (sodium heparin). After mixing, the samples were centrifuged at high speed (approximately 3000 rpm) for 10 minutes at 4° C. The resulting plasma was separated into two approximately equal aliquots in appropriately labeled amber polypropylene tubes and placed in the freezer until shipment for analysis. The time from blood collection until the blood samples were placed in the centrifuge did not exceed 30 minutes and the time from blood collection until the plasma samples were placed in the freezer did not exceed 60 minutes. All samples were stored frozen to −19° C. or colder.

As doxycycline is sensitive to ultraviolet/sunlight, sample collection and sample processing were conducted under yellow light conditions. During collection/processing and until placement in the freezer, blood/plasma samples were kept cooled in an ice/water bath.

7.5 Pharmacokinetic Results

Pharmacokinetic parameters are illustrated below in Table 10. Arithmetic means of the pharmacokinetic parameters (untransformed); geometric means, ratio of means, and their associated geometric 90% confidence intervals based on ANOVA (1n-transformed); and statistical comparisons are provided below in Table 11. A non-parametric analysis of $T_{max}$ is provided below in Table 12.

Twenty-eight (28) subjects were enrolled in the study, and all subjects were healthy adults. Twenty-eight (28) subjects were dosed in Period I, 28 subjects were dosed in Period II, and 28 subjects completed both periods of the study. The plasma samples from 28 subjects were assayed for doxycycline.

There are 56 sets of data (28 Test A and 28 Reference B) from 28 subjects eligible for the bioequivalence analysis of doxycycline in this study. The pharmacokinetic parameters were determined from the plasma concentration data using a non-compartmental model. The terminal elimination rate constants were estimated from the plasma doxycycline data for all subjects using the plasma concentrations of the terminal elimination phase as best as could be determined from the plasma concentration vs. time plots (log scale) for the individual subjects. Confidence intervals (90%) were constructed using Koch and Hauschke's method for non-parametric analysis of equivalence at the $\alpha=0.05$ level of significance for the $T_{max}$ parameter. No statistically significant period or carryover effect was identified. As the 90% CI for treatment effect contained 0, the test and reference products were demonstrated to be equivalent for $T_{max}$. The scheduled times were used in the pharmacokinetic calculations. In cases where there were blood draw time deviations, the actual times of collection were used.

TABLE 10

Summary of Pharmacokinetic Parameters of Untransformed Data

| | Arithmetic mean ± SD (%CV) | |
| --- | --- | --- |
| Pharmacokinetic Parameter | Test A (N = 28 datasets) | Reference B (N = 28 datasets) |
| $AUC_{0-t}$ (mcg · hr/mL) | 23.1586 ± 7.0849 (30.5930) | 23.0624 ± 7.3907 (32.0465) |
| $AUC_{0-inf}$ (mcg · hr/mL) | 26.6901 ± 7.9403 (29.7499) | 26.6142 ± 8.0398 (30.2087) |
| $AUC_{0-t}/AUC_{0-inf}$ ratio | 0.8645 ± 0.0502 (5.8064) | 0.8624 ± 0.0488 (5.6542) |
| $C_{max}$ (mcg/mL) | 1.6188 ± 0.6187 (38.2193) | 1.6522 ± 0.6927 (41.9267) |
| $T_{max}$ (hr) | 2.7800 ± 1.0034 (36.0935) | 2.6721 ± 0.7208 (26.9759) |
| Median $T_{max}$ (hr) (min-max) | 2.84 (1.00-4.50) | 2.50 (1.50-4.00) |
| $K_{el}$ (1/hr) | 0.0449 ± 0.0122 (27.2468) | 0.0456 ± 0.0109 (23.8205) |
| $T_{1/2}$ (hr) | 16.5427 ± 4.5441 (27.4689) | 16.0336 ± 3.9370 (24.5544) |

TABLE 11

Summary of Study Results Based on Plasma Doxycycline Concentrations
Study No.: 11450707
Plasma PK and BE Parameters of Doxycycline

| Parameter | Trt | # Datasets | LS Geometric Mean | Contrast (# subjects) | LSGM Ratio (%) | 90% Confidence Interval (%) | ISCV(%) | P-value Period | P-value Sequence | BE Outcome |
| --- | --- | --- | --- | --- | --- | --- | --- | --- | --- | --- |
| $AUC_{0-t}$ (mcg · hr/mL) | A | 28 | 22.09 | A vs B (n = 28) | 100.67 | 91.66-110.56 | 20.8 | 0.6584 | 0.7953 | Pass |
| | B | 28 | 21.94 | | | | | | | |
| $AUC_{0-\infty}$ (mcg · hr/mL) | A | 28 | 25.60 | A vs B (n = 28) | 100.43 | 92.18-109.42 | 19.0 | 0.4716 | 0.9227 | Pass |
| | B | 28 | 25.49 | | | | | | | |
| $C_{max}$ (mcg/mL) | A | 28 | 1.512 | A vs B (n = 28) | 98.68 | 89.38-108.95 | 22.0 | 0.6367 | 0.9624 | Pass |
| | B | 28 | 1.532 | | | | | | | |

TABLE 12

Nonparametric Statistical Analysis for Difference in Median $T_{max}$
Using the Method of Koch and Hauschke (Informational)

| Effect | Estimate (Median) | 90% LCI | 90% UCI |
| --- | --- | --- | --- |
| Treatment | 0.250 | −0.165 | 0.505 |
| Carryover | 0.165 | −0.830 | 1.650 |
| Period | 0.250 | 0.000 | 0.580 |

7.6 Pharmacokinetic Conclusions

For the natural log-transformed data for doxycycline, the 90% confidence intervals on the geometric mean test-to-reference ratios for $AUC_{0-t}$, $AUC_{0-inf}$, and $C_{max}$ fall within the standard bioequivalence range of 80.00-125.00%. Therefore, the test formulation of doxycycline hyclate 120 mg DR Tablet (manufactured by Mayne Pharma International Pty.

Ltd.) was demonstrated to be bioequivalent to the reference formulation, doxycycline hyclate delayed-release tablets, USP 100 mg (manufactured by: Mayne Pharma International Pty. Ltd.; distributed by: Midlothian Laboratories), under fasted conditions in healthy adult subjects. As aforementioned, the taught formulations are bioequivalent, but exhibit a different pH profile compared to current doxycycline formulations, which is particularly different at low pH, in that lower levels of release coupled with higher overall doxycycline dose, provides a bioequivalent composition with less stomach irritation and potentially less nausea, see e.g. FIG. 11.

A comparison of the time to (the observed) peak concentration ($T_{max}$) was assessed between the test and reference products. A nonparametric analysis revealed that no statistically significant period or carryover effect was identified. As the 90% CI for treatment effect contained 0, the test and reference products were demonstrated to be equivalent for $T_{max}$. There were no serious adverse events reported during the study.

Figure 7:
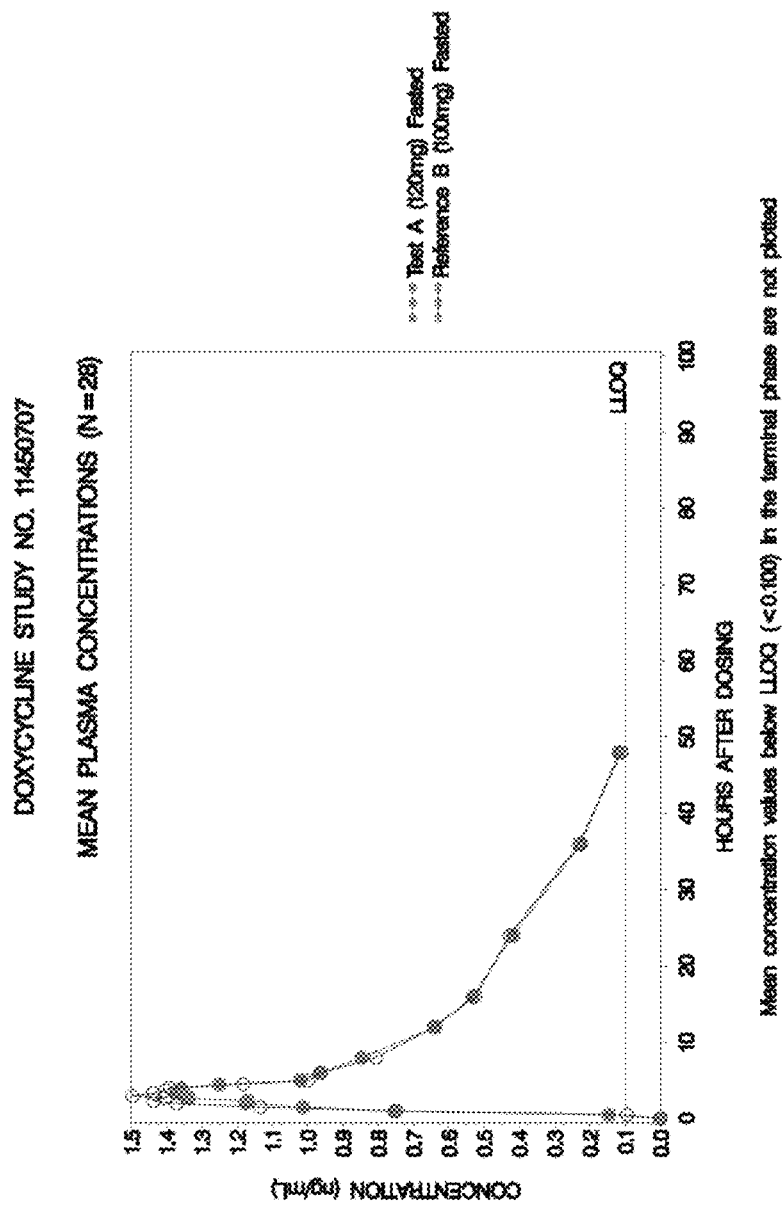
FIG. 7 is a graph of the mean plasma concentration versus time plot (linear) of doxycycline present in the plasma of subjects treated with a dosage form (i.e. a tablet) comprising controlled release doxycycline pellet formulation B (120 mg) compared to a reference DORYX doxycycline tablet (100 mg) under fasted conditions, as outlined in Example 7.

Further results from this study can be found in FIG. 7 and FIG. 13.

Example 8: Population Pharmacokinetic Model of Doxycycline Plasma Concentrations—Pooled Study Data The objective of this study was to evaluate the relative bioavailability of a test formulation of doxycycline hyclate 120 mg DR Tablet compared to the marketed reference product, doxycycline hyclate delayed-release tablets, USP 100 mg, in healthy adult male and female subjects under fasted conditions.

8.1 Summary

The literature is presently void of a population pharmacokinetic analysis of doxycycline. This study aimed to develop a population pharmacokinetic model of doxycycline plasma concentrations that could be used to assess the power of bioequivalence between Doryx® Delayed-Release tablets and Doryx MPC®. The Doryx MPC is a tablet comprising "Pellet B" formulation. Doxycycline pharmacokinetic data was available from eight phase 1 clinical trials following single/multiple doses of conventional release doxycycline capsules, Doryx® Delayed-Release tablets and Doryx MPC® under fed and fasted conditions. A population pharmacokinetic model was developed in a step-wise manner using NONMEM® 7.3. The final covariate model was developed according to a forward-inclusion (p<0.01) and then backward deletion (p<0.001) procedure. The final model was a two compartment model with two-transit absorption compartments. Structural covariates in the base model included formulation effects on relative bioavailability (F), absorption lag (ALAG) and the transit absorption rate (KTR) under the fed status. An absorption delay (lag) for the fed status (FTLAG2=0.203 h) was also included in the model as a structural covariate. The fed status was observed to decrease F by 10.5%, and the female sex resulted in a 14.4% increase in clearance. This study presents the first population pharmacokinetic model of doxycycline plasma concentrations following oral doxycycline administration. The model was used to assess the power of bioequivalence between Doryx® Delayed-Release tablets and Doryx MPC®, and it could potentially be used to critically examine and optimize doxycycline dose regimens.

8.2 Introduction

Doxycycline is an oral tetracycline antimicrobial which possesses anti-inflammatory mechanisms that contribute to its use in conditions such as acne vulgaris [1]. As a second generation tetracycline, doxycycline has increased lipophilicity over its predecessors, with increased absorption and tissue penetration [2,3]. Doxycycline absorption occurs in the duodenum, with oral bioavailability within the range of 73 to 95% [2,3]. Doxycycline also has improved absorption in the fed state and in the presence of dairy products compared to first generation tetracycline's, to the point that delayed release doxycycline tablets are marketed to be taken with or without food, although some guidelines indicate to take with food or milk to reduce stomach upset [2-4].

Mayne Pharma International currently has two marketed oral formulations available in the United States, a delayed-release doxycycline hyclate tablet (Doryx® Delayed-Release tablets), and the recently launched Doryx MPC® Delayed-Release tablets [5]. The Doryx® Delayed-Release tablet has increased acid resistance compared to the defunct conventional release capsules, which is expected to result in less release of doxycycline prior to the small intestine. The Doryx® Delayed-Release tablet was developed due to an association between drug release in acid and the potential occurrence of oesophageal and gastric irritation [5].

Despite the delayed release properties of Doryx® Delayed-Release tablets, some doxycycline release does occur in acid environments, potentially resulting in drug release in the stomach prior to gastric emptying. Accordingly, the Doryx MPC® Delayed-Release tablet was developed with increased in-vitro acid resistance and a further delay to release. Based upon prior evidence, Doryx MPC® Delayed-Release tablets have the potential to offer increased protection from oesophageal and gastric irritation. Given the change in the acid release profile of Doryx MPC® Delayed-Release tablets, it was anticipated that the formulation would demonstrate a reduction in the bioavailability compared to the Doryx® Delayed-Release tablet on a mg per mg basis. To address this reduction in relative bioavailability, Doryx MPC® Delayed-Release tablets were formulated to have a 20% higher doxycycline (hyclate) content (120 mg) relative to Doryx® Delayed-Release tablets (100 mg).

Doxycycline is predominately cleared unchanged in the urine and feces, through renal, biliary and intestinal wall elimination, resulting in a half-life between 15 and 25 hours [3]. Previously, Beringer et al [6] performed a compartmental pharmacokinetic analysis in 20 cystic fibrosis adults dosed with multiple 40 mg, 100 mg or 200 mg doses of oral doxycycline (formulation unspecified), and found a two-compartment model with a delay (lag) on first-order absorption to best describe the plasma concentration-time data. To our knowledge, there are no population pharmacokinetic analyses in the literature exploring doxycycline concentrations following oral administration. Such an analyses is essential to the development of a population pharmacokinetic-pharmacodynamic model that could be used to critically examine and optimize doxycycline dose regimens, which has been under-studied to date [2]. In this study, phase I pharmacokinetic data collected by Mayne Pharma International following the administration of either the conventional release doxycycline capsules, Doryx® Delayed-Release tablets or Doryx MPC® Delayed-Release tablets were used to develop a population pharmacokinetic model. The primary aim of the study was to assess the equivalence of doxycycline plasma exposure following a 100 mg Doryx® Delayed-Release tablet or a 120 mg Doryx MPC® Delayed-Release tablet. The influence of the fasted/fed status was also assessed on the pharmacokinetics of the new formulation.

Materials and Methods (8.3-8.8)

8.3 Pharmacokinetic Data

Pharmacokinetic data were available from eight phase 1 clinical trials conducted by Mayne Pharma International. These studies assessed doxycycline plasma concentrations following oral administration of either a 100 mg conventional release doxycycline hyclate capsule, a 75/100/150 or 200 mg Doryx® Delayed-Release tablet or a 120 mg Doryx MPC® Delayed-Release tablet in healthy subjects. For the remainder of the Specification's Example 8, conventional release doxycycline hyclate capsules will be referred to as Doryx capsules, the Doryx® Delayed-Release tablets will be referred to as Doryx tablets, and Doryx MPC® Delayed-Release tablets (formulation code MP336) will be referred to as Doryx MPC.

The available phase 1 clinical trials included six single dose two treatment period studies assessing the influence of formulation or the fed/fasted state on doxycycline concentrations. Two trials were multi-dose studies; with one a single treatment period study and the other a two treatment period study assessing doxycycline plasma concentrations following Doryx capsule or Doryx tablet administration. All studies were conducted in the United States. All studies that included two-treatment periods were randomized crossover studies that had a 14 day washout after the completion of the first plasma sampling period. The design and dosing schedules are summarized in Table 13. The available studies were assigned a local identifier during model development (10, 20, 30, 40, 50, 60, 70, and 80), as indicated in Table 13, and will be referred to by these numbers for the remainder of the Specification.

TABLE 13

Phase 1 Clinical Trial Data Utilized

| Study ID | Protocol No. | No. of subjects recruited to study | No. of subjects with concentration data presented | Single/ multiple dose | Fed/ Fasted Study | No. of treatment periods per subject | Dosing schedules | LLOQ (µg/ml) |
|---|---|---|---|---|---|---|---|---|
| 10 | 11450707 | 28 | 28 | Single | No | 2 | Doryx MPC (120 mg) vs Doryx (100 mg) tablet | 0.1 |
| 20 | PR-08302.0 | 18 | 18 | Single | Yes | 2 | Doryx (100 mg) tablet Fed/Fasted | 0.025 |
| 30 | PR-02308.0 | 18 | 17 | Single | Yes | 2 | Doryx (200 mg) tablet Fed/fasted | 0.05 |
| 40 | PR-06410 | 20 | 19 | Multiple | No | 1 | Doryx 200 mg tablet | 0.05 |
| 50 | PR-02707 | 26 | 25 | Single | No | 2 | Doryx (150 mg) tablet vs 2*Doryx (75 mg) tablets | 0.05 |
| 60 | PR-02108.1 | 26 | 23 | Single | No | 2 | Doryx (200 mg) tablet vs 2*Doryx (100 mg) tablets | 0.05 |
| 70 | PR-01402.0 | 24 | 20 | Multiple | No | 2 | Doryx (100 mg) tablet vs Doryx (100 mg) capsule | 0.025 |
| 80 | MYP-P2-991 | 28 | 28 | Single | Yes | 2 | Doryx MPC (120 mg) Fed/Fasted | 0.01 |

Studies 10, 20, 30, 50, 60 and 80 were single-dose studies and plasma samples were acquired at nominal times approximate to 0, 0.25, 0.5, 1, 1.5, 2, 2.5, 3, 3.5, 4, 6, 8, 10, 12, 16, 24, 36, 48, 72 and 96 hours after the dose on day 1 of that period. Study 40 was a single treatment period multi-dose study, where participants were dosed 7 times at 24 hour intervals and plasma samples were collected at nominal times of 0, 0.25, 0.5, 1, 1.5, 2, 2.5, 3, 4, 6, 8, 10, 12, 16, 24, 144, 144.25, 144.5, 145, 145.5, 146, 146.5, 147, 148, 150, 152, 156, 160, 168, 180, 192, 216 and 240 hours after the dose on day 1. Study 70 was a two treatment period multi-dose study, where doses were given at 0, 72, 96, 120, 144 and 168 hours after the start of treatment, and plasma samples were collected at nominal times of 0, 0.25, 0.5, 1, 1.5, 2, 2.5, 3, 4, 6, 8, 10, 12, 16, 24, 36, 48, 72, 96, 120, 144, 168, 168.25, 168.5, 169, 169.5, 170, 170.5, 171, 172, 174, 176, 180, 184, 192, 204, 216 and 240 hours after the dose on day 1. Deviations between nominal sampling times and actual sample times were recorded, and the actual times were used during model development. Covariates describing fed status, formulation, sex, age, race, weight, body mass index (BMI), smoking status and study number were available for each individual.

Doxycycline plasma concentrations were measured using validated high performance liquid chromatographic methods, with the lower limits of quantification (LLOQ) of the assays indicated in Table 13. All subjects with evaluable pharmacokinetic data were included in the analysis. All studies were conducted according to the International Conference of Harmonisation (ICH) guidelines for good clinical practice [7], the Declaration of Helsinki on the ethical conduct of medical research [8], and applicable regulatory requirements. Each subject signed and dated a written informed consent before study participation.

8.4 Modelling Software

Modelling was performed using a Dell PowerEdge R910 server with 4×10 core Xeon 2.26-Ghz processors running the Windows Server 2008 R2 Enterprise 64-bit operating system. Model development employed nonlinear mixed-effects modelling using NONMEM version 7.3 [9], with the Wings for NONMEM interface (http://wfn.sourceforge.net) and Intel Visual Studio Fortran compiler. Data manipulation and post-run processing of NONMEM output was conducted using the R data analysis language (Version 3.1.1 or greater) and the packages ggplot2, GGally, foreign, tidyr, Hmisc, gdata, doBy, plyr, grid, stringr and npde [10-22].

8.5 General Modelling Strategy

The base model was developed in a step-wise manner. Pharmacokinetic models were coded using the ADVAN5 subroutines of NONMEM. Linear kinetic models with 1, 2 and 3 compartments were evaluated, with absorption models including simple first-order absorption and "transit compartment" models with up to 5 absorption transit compartments assessed. The parameter KTR (transit absorption rate) was used to describe the first-order movement through these absorption compartments. The First Order Conditional Estimation (FOCE) method was used to fit models. The base model was selected on the basis of mechanistic plausibility, visual inspection of goodness-of-fit diagnostic plots, the precision of parameter estimates (se %<30% for fixed, <50% for random and <51.2% for covariate effects parameters), and the lowest value of the Akaike's information criterion (AIC; Equation 1) in accordance with the number of parameters and the final objective function value (OBJ). The base model was also required to pass the covariance step.

$$AIC = OBJ + 2*\text{number of parameters} \quad \text{Equation 1}$$

Unless stated otherwise, population parameter variability (PPV) was represented using an exponential error model:

$$P_j = TVP * e^{\eta j} \quad \text{Equation 2}$$

Where $P_j$ is the individual value for the parameter in the $j^{th}$ individual, TVP is the typical population value of P and $\eta j$ is an independent random variable with a mean of zero and variance $\omega^2$.

Models with and without covariance for P were investigated using the OMEGA BLOCK functionality of NONMEM. Population parameters were tested for between-occasion variability (BOV) where pharmacokinetic data were available from two treatment periods. Total PPV was defined as:

$$PPV = \eta + OCC1 * \kappa_j + OCC2 * \kappa_j \quad \text{Equation 3}$$

Where the variance of represents between subject variability (BSV) and the variance of κ represents BOV. OCC1 was a flag that has a value of 1 when period equals 1, and zero otherwise. OCC2 was a flag that has value 1 when period equals 2, and zero otherwise etc. κ is a random variable with mean zero and variance $\omega^2$ that is equal for all occasions (via the OMEGA SAME structure in NONMEM, thus assuming BOV was the same for all occasions).

A combined proportional ($\theta_{prop}$) and additive residual ($\theta_{add}$) error model of the doxycycline concentrations (C) was used, where estimation of a THETA was employed and epsilon was fixed to zero:

$$C_{ij} = \hat{C}_{ij} + \sqrt{\theta_{prop}^2 * \hat{C}_{ij}^2 + \theta_{add}^2} \quad \text{Equation 4}$$

$C_{ij}$ is the $i^{th}$ concentration measured in the $j^{th}$ individual, $\hat{C}_{ij}$ is the model predicted $C_{ij}$, and $\theta_{prop}$ and $\theta_{add}$ are parameters representing the proportional and additive residual error, respectively. The influence of the additive component of the error was also examined by a comparison with a proportional only error model. The YLO and M3 methods for censored concentrations below the limit of quantification (BLOQ) were also investigated [23].

All models were investigated with allometric scaling, initially through total body weight (TBW) referenced to 70 kg and an exponent fixed of 0.75 for clearance parameters and 1 for volumes [24]. Allometric scaling to fat free mass (FFM [25]) and normal fat mass (NFM [26]) were also considered. Structural covariates controlling the bioavailability differences between formulations and fed status, as well as KTR differences between formulations and fed status were investigated early, and where appropriate, were incorporated within the base model. Given the extensive washout between dosing periods, and that all period 2 pre-dose samples were BLOQ, the EVID=4 functionality of NONMEM was utilised to reset all compartment amounts to 0 at the start of a new dosing period.

During the final stage of base model development, between study differences on the population parameter values were investigated. This was important due to the sampling time differences between the studies and a tendency for subtle changes in pharmacokinetic parameters to occur from one study to another[27], and thus affecting the visual predictive checks subset by study. As guided by Laporte-Simitsidis et al. [27] for a pooled analysis containing less than 20 studies, a fixed study-effect method was used where the effect of each study was represented within a binary relationship.

Prediction Corrected Visual Predictive Checks (pcVPC) were used to discriminate between candidate base and covariate models [28]. For the pcVPC's, the median, $5^{th}$ and $95^{th}$ percentiles of the prediction-corrected observations were compared against the empirical 95% confidence intervals (CI) of the median, $5^{th}$ and $95^{th}$ percentiles of prediction-corrected doxycycline concentrations from 200 simulations of the index (original) dataset. The predictive performance of the model was considered acceptable if the median, $5^{th}$ and $95^{th}$ percentile of the prediction-corrected observed data lay inside the CI's of the prediction-corrected simulated data for the majority of the time. In addition to the pcVPC, the percentage of the observed data BLOQ throughout time was compared against the 95% CI of the percentage of BLOQ data from the 200 simulations of the original dataset (BLOQ VPC). The predictive performance of the model was considered acceptable if the BLOQ data percentage of the original data lied within the predicated CI for the simulation data for the majority of time.

8.6 Covariate Model Building

The base model was screened for the influence of covariates based upon physiological plausibility and prior knowledge of the factors considered to influence doxycycline plasma concentrations (Table 14). The effects of continuous covariates on a parameter were represented as a power function referenced to the median value of the covariate in the data, while the effects of categorical covariates on a parameter were represented by a binary relationship. The effects of doxycycline dose and tablet strength were also investigated through linear functions referenced to the median value in the data.

TABLE 14

Biologically Guided Covariates Screening Plan

| Parameter | Covariates screened |
|---|---|
| Relative Bioavailability (RELF) | Fed status*, dose, tablet strength, sex, age, race |
| Transit absorption rate (KTR) | Formulation, dose, tablet strength, sex, age, race |
| Central compartment volume (V) | Sex, age, race |
| Clearance (CL) | Dose, sex, age, race, smoker status |
| Peripheral compartment volume (VP1) | Sex, age, race |

*Fed status effect on RELF was also assessed for a difference between formulation.

The potential inclusion of covariates on the base model were selected based upon a significant decrease in OBJ at the p<0.01 level (6.63 units for one parameter). The final model was developed via a forward inclusion/backward deletion process. Whereby each covariate (significant on screening) was sequentially added, starting with the covariate that caused the largest drop in the OBJ. Covariate(s) were only retained if there was a significant decrease in OBJ at the p<0.01 level. The final model was further subjected to a backward elimination procedure at the p<0.001 level (10.8 units for one parameter) starting with the least significant covariate from the forwards inclusion step.

8.7 Simulations and Power Analysis

The final model determined from the doxycycline data was used to perform simulations and power analyses of bioequivalence, according to the randomised cross-over designs of:

120 mg Doryx MPC compared to 100 mg Doryx tablet (fasted);

120 mg Doryx MPC compared to 100 mg Doryx tablet (fed);

120 mg Doryx MPC compared to 120 mg Doryx MPC (fed/fasted); and 100 mg Doryx tablet compared to 100 mg Doryx tablet (fed/fasted).

For the simulations and power analyses, the between study effect parameters identified in the final model were set to the mean value of the eight studies. Studies including 12, 24, 28, and 36 subjects were simulated 1,000 times and non-compartmental analysis (NCA) pharmacokinetic exposure parameters ($AUC_{0t}$, $AUC_{inf}$, $C_{max}$ and $T_{max}$) were calculated. These NCA metrics were calculated for the simulated test and reference product concentrations using an R script. NCA metrics below the $2.5^{th}$ and above the $97.5^{th}$ percentile were not used for summary statistics, as they present as outliers and their inclusion was considered to produce summary statistics that are not representative of model predictions. For each simulated cross-over study, NCA metric equivalence and bioequivalence was assessed through the use of an analysis of variance (ANOVA) method [29,30]. For the 1000 simulated studies of 28 subjects, the median and 90% CI of the predicted doxycycline concentrations were plotted, but not illustrated here.

Test and reference ln-transformed $AUC_{0t}$, $AUC_{inf}$, $C_{max}$ or $T_{max}$ values were subjected to a validated ANOVA using the aov function in R [31]. For the bioequivalence analysis, each simulated study's variance was partitioned into components of subject, period, sequence and formulation. Using the results of the ANOVA, the conf.int function in R was used to calculate the 90% CI of the difference between the test and reference ln-transformed $AUC_{0t}$, $AUC_{inf}$, $C_{max}$ and $T_{max}$ data. Subsequently, the ln-transformed interval was converted into the linear domain, and equivalence was demonstrated for a given metric if the 90% CI fell within the range of 0.8 to 1.25.

Although $T_{max}$ was assessed for equivalence power for completeness, $T_{max}$ was not used in the assessment of bioequivalence power. Rather, overall bioequivalence ($BE_{0t}$ and $BE_{inf}$, respectively) was assumed where $AUC_{0t}$ and $C_{max}$ or $AUC_{inf}$ and $C_{max}$ both had 90% CI within 0.80 to 1.25 for a given study. The percentage of bioequivalent studies were interpreted as the power of the study design for establishing bioequivalence between the two formulations given the trial design and dose selection used in that simulation. Additionally, the studies that were deemed bioequivalent were assessed for whether the 90% CI of ln-transformed test to reference ratio for $AUC_{0t}$, $AUC_{inf}$ and $C_{max}$ included 1.

Results (8.9-8.13)

8.8 Study Population and Pharmacokinetic Data

There were 188 subjects in total enrolled across the eight phase 1 clinical trials. A summary of the study populations' demographics is represented in Table 15.

TABLE 15

Study Population Characteristics

| Characteristic* | |
|---|---|
| Age (years) | 28 (18-73) |
| Smoker | 156 non-smokers, 22 smokers |
| BMI | 25.25 (18.1-34.5) |
| Weight (kg) | 75.9 (47.2-114.4) |
| FFM (kg) | 56.3 (32.3-80.1) |
| Sex | 120 males, 58 females |
| Race | 99 Caucasian/whites, 79 other[#] |

*All values calculated as mean (median, range), unless stated otherwise.
[#]The category of other was used due to variability in the ethnicity categorisation between the available studies. For example Studies 30, 40, 50, 60 and 80 categorised participants as white, black, American Indian or Hispanic/Latino. Studies 20 and 70 categorised participants as Caucasian, black, Hispanic and American Indian. Finally Study 10 categorised participants as white, black, Asian and other.

All subjects with evaluable pharmacokinetic data (including partial data) were included in the analysis. In total, pharmacokinetic data were available from 178 participants, who received a total of 651 oral doxycycline doses in both single and multi-dose studies, with either one or two treatment periods. Participants contributed 7093 doxycycline plasma concentrations across these studies. Overall, 12.7% of the doxycycline plasma concentration data were missing, predominately at the beginning or end of the observation periods, where plasma concentrations were BLOQ. Models accounting for BLOQ-censored data were investigated using the YLO and M3 methods [23]; however, these were characterized by unreliable minimization and covariance step status. Samples below the limit of quantitation (BLQ) were thus excluded a priori from the data set (M1 method). For the base and final model, BLOQ VPCs were used to ensure there was sufficient data to describe the elimination phase of doxycycline. There was no missing covariate data from the study.

8.10 Base Model

The base model of the available doxycycline plasma concentrations which best fit the model building criteria was a two compartment model with two-transit absorption compartments (FIG. 14). The model was allometrically scaled for fat free mass (FFM), had a covariance matrix with between subject variability for the parameters—transit compartment absorption rate (KTR), apparent clearance (CL), apparent central volume (V) and apparent peripheral volume (VP1). Between occasion variability was included on KTR and CL. The model had a proportional and an additive residual error term. Structural covariates included in the base model were a formulation effect (FMPC, FCAP) on relative bioavailability (F), an absorption lag on the Doryx MPC and Doryx capsule formulations (ALAG), an absorption lag for the fed status (FTLAG2); and a food effect on KTR for the Doryx tablet and capsules (COVFED), as well as Doryx MPC (COVFED2). Between study differences were also included on the F, KTR, CL and V parameters. For the between study differences on F, there were three groups apparent, where Studies 10, 30 and 50 were grouped (reference group); Studies 20, 70 and 80 were grouped (COVSTDF1); and Studies 40 and 60 were grouped (COVSTDF2). For the between study differences on the KTR parameter two groups were apparent where Studies 10, 20, 70 and 80 were grouped (reference group); and Studies 30, 40, 50 and 60 were grouped (COVSTDKTR). For the between study differences on the CL and V parameters, two groups were apparent where Study 10 was a group (reference group); and Studies 20, 30, 40, 50, 60, 70 and 80 were grouped (COVSTDCL; COVSTDV). The parameter estimates for the base model were calculated (not presented). Given the diagnostic plots of the base model were consistent with an unbiased model and the pcVPC showed a good description of the data (data not presented), it was considered that the structural and population components of the model appropriately represented the data, allowing for confidence in the subsequent analysis of covariates and power analyses.

8.11 Final Model

The base model was screened for the potential inclusion of covariates with Table 16 presenting the drop in OBJ, the number of parameters and the significance (p-value) upon each covariate screening. Of the screened covariates, only fasted/fed effect on relative bioavailability (COVFEDF on RELF: OBJ drop of 41.837 for 1 parameter), sex effects on clearance (COVSEX on CL: OBJ drop of 25.661 for 1 parameter) and sex effects on volume (COVSEX on V: OBJ drop of 15.086 for 1 parameter), significantly decreased the OBJ at the p<0.01 level with acceptable parameter precision. A fasted/fed effect dependent on formulation was also explored on relative bioavailability (COVFEDF=Doryx tablet and capsule; COVFEDFMPC=Doryx MPC; OBJ drop of 43.739 for 2 parameter). Despite a significant drop in OBJ, the estimation of the COVFEDFMPC parameter was imprecise (se %=63.3) and it was not included in the model.

TABLE 16

Significance of Screened Covariates on the Base Model

| Covariate Screened | PAR Added | OBJ drop | P-value |
|---|---|---|---|
| Fed status* on RELF | 2 | 43.739 | <0.01 |
| Fed status on RELF | 1 | 41.837 | <0.01 |
| Sex on CL | 1 | 25.661 | <0.01 |
| Sex on V | 1 | 15.086 | <0.01 |
| Tablet strength on RELF | 4 | 11.849 | >0.01 |
| Age on RELF | 1 | 5.291 | >0.01 |
| Smoker status on CL | 1 | 2.554 | >0.01 |
| Dose on CL | 1 | 2.484 | >0.01 |
| Age on KTR | 1 | 2.274 | >0.01 |
| Sex on RELF | 1 | 1.853 | >0.01 |
| Dose on RELF | 1 | 1.157 | >0.01 |
| Tablet strength on KTR | 4 | 1.129 | >0.01 |
| Formulation on KTR | 2 | 1.09 | >0.01 |
| Age on V | 1 | 0.982 | >0.01 |
| Sex on VP1 | 1 | 0.756 | >0.01 |
| Race on VP1 | 1 | 0.436 | >0.01 |
| Sex on KTR | 1 | 0.151 | >0.01 |
| Race on CL | 1 | 0.104 | >0.01 |
| Race on KTR | 1 | 0.075 | >0.01 |
| Race on RELF | 1 | 0.061 | >0.01 |
| Age on VP1 | 1 | 0.053 | >0.01 |
| Dose on KTR | 1 | 0.05 | >0.01 |
| Race on V | 1 | 0.019 | >0.01 |
| Age on CL | 1 | 0.011 | >0.01 |

*Fed status effect on RELF dependent upon formulation (covariates se % was 63.3 and it was not explored further).
OBJ drop is the drop in the objective function value from the base model when fitting with the screened covariate, PAR Added is the number parameters added to the base model, P-value indicates whether upon screening the covariate tested resulted in a significant drop in the OBJ at the p < 0.01 level (6.63 units for one parameter).

On forward inclusion, sex effects on clearance (COVSEX on CL) were retained in the full covariate model after decreasing the OBJ by a further 25.492 compared to the model containing just a fasted/fed effect on relative bioavailability (COVFEDF on RELF). The inclusion of sex effects on volume (COVSEX on V) did not further improve the covariate model (OBJ drop 1.05 units). The backwards deletion of sex effects on clearance (COVSEX on CL) and fasted/fed effect on relative bioavailability (COVFEDF on RELF), respectively increased the OBJ function by 25.492 and 41.668 units and thus both were retained in the final covariate model at the p<0.001 level. This model was therefore declared the final model as it passed the model building criteria. The parameter estimates for the final model are shown in Table 17.

TABLE 17

Parameter Values for the Final Model

| Code | | Description | Units | Parameter estimate | se % | Shrinkage (%) | ETA p-value |
|---|---|---|---|---|---|---|---|
| Population parameters | | | | | | | |
| V | $\Theta_3$ | Central distribution volume | L/70 kg FFM | 55.2 | 7.8 | | |
| CL | $\Theta_4$ | Clearance | L/h/70 kg FFM | 4.63 | 5.0 | | |

TABLE 17-continued

Parameter Values for the Final Model

| Code | | Description | Units | Parameter estimate | se % | Shrinkage (%) | ETA p-value |
|---|---|---|---|---|---|---|---|
| VP1 | $\Theta_5$ | Peripheral distribution volume | L/70 kg FFM | 49.8 | 3.5 | | |
| CLP1 | $\Theta_6$ | Intercompartmental clearance | L/h/70 kg FFM | 11.3 | 4.1 | | |
| KTR | $\Theta_7$ | Transit compartment rate constant | $h^{-1}$ | 2 | 4.3 | | |
| F1MPC | $\Theta_8$ | Relative bioavailability of Doryx MPC compared to Doryx table | | 0.863 | 4.9 | | |
| F1CAP | $\Theta_9$ | Relative bioavailability of Doryx capsule compared to Doryx tablet | | 0.978 | 3.8 | | |
| COVFED | $\Theta_{10}$ | Effect of food on KTR for the Doryx tablet and capsules | | −0.209 | 26.3 | | |
| COVFED2 | $\Theta_{11}$ | A food effect on KTR for Doryx MPC | | −0.549 | 7.7 | | |
| ALAG1 | $\Theta_{12}$ | A lag on KTR for the Doryx MPC and Doryx Capsule formulations | h | 0.115 | 24.4 | | |
| FTLAG2 | $\Theta_{13}$ | A lag on KTR for the fed status | h | 0.203 | 14.2 | | |
| Between study effects | | | | | | | |
| COVSTDF1 | $\Theta_{14}$ | Effect of Studies 20, 70 and 80 on relative bioavailability | | 0.516 | 11.9 | | |
| COVSTDF2 | $\Theta_{15}$ | Effect of Studies 40 and 60 on relative bioavailability | | −0.146 | 19.9 | | |
| COVSTDKTR | $\Theta_{16}$ | Effect of Studies 30, 40, 50 and 60 on KTR | | −0.213 | 17.3 | | |
| COVSTDCL | $\Theta_{17}$ | Effect of Studies 20, 30, 40, 50, 60, 70 and 80 on CL | | −0.241 | 18.0 | | |
| COVSTDV | $\Theta_{18}$ | Fractional effect of Studies 20, 30, 40, 50, 60, 70 and 80 on V | | −0.245 | 26.7 | | |
| Covariate effects | | | | | | | |
| COVFEDF | $\Theta_{19}$ | Effect of food on relative bioavailability | | 0.105 | 33.2 | | |
| COVSEX | $\Theta_{20}$ | Effect of female sex on CL | | 0.144 | 20.4 | | |
| Between subject variability | | | | | | | |
| BSV_CL ($\eta_1$) | $\omega_1$ | Between subject variability on CL | % CV | 19.3 | 6.4 | 9.1 | 0.959 |
| BSV_KTR ($\eta_2$) | $\omega_2$ | Between subject variability on KTR | % CV | 28.2 | 8.3 | 14.6 | 0.891 |
| Population variability | | | | | | | |
| PPV_VP1 ($\eta_3$) | $\omega_3$ | Population variability on VP1 | % CV | 15.1 | 11.2 | 30.7 | 0.870 |
| PPV_V ($\eta_4$) | $\omega_4$ | Population variability on V | % CV | 37.6 | 5.8 | 7.8 | 0.913 |
| Between occasion variability | | | | | | | |
| BOVCL1 ($\eta_5$) | $\omega_5$ | Between occasion variability on CL (period 1) | % CV | 13.5 | 7.8 | 23.0 | 0.978 |
| BOVCL2 ($\eta_6$) | $\omega_6$ | Between occasion variability on CL (period 2) | % CV | 13.5 | — | 25.3 | 0.853 |
| BOVKTR ($\eta_7$) | $\omega_7$ | Between occasion variability on KTR (period 1) | % CV | 27.2 | 10.5 | 15.6 | 0.815 |
| BOVKTR ($\eta_8$) | $\omega_8$ | Between occasion variability on KTR (period 2) | % CV | 27.2 | — | 9.2 | 0.888 |
| Covariance | | | | | | | |
| $\Theta_4, \Theta_7$ | $\omega_1, \omega_2$ | Covariance between CL and KTR | | 0.420 | | | |
| $\Theta_4, \Theta_5$ | $\omega_1, \omega_3$ | Covariance between CL and VP1 | | 0.363 | | | |
| $\Theta_4, \Theta_3$ | $\omega_1, \omega_4$ | Covariance between CL and V | | 0.720 | | | |
| $\Theta_7, \Theta_5$ | $\omega_2, \omega_3$ | Covariance between KTR and VP1 | | −0.234 | | | |
| $\Theta_7, \Theta_3$ | $\omega_2, \omega_4$ | Covariance between KTR and V | | 0.884 | | | |
| $\Theta_5, \Theta_3$ | $\omega_3, \omega_4$ | Covariance between VP1 and V | | −0.089 | | | |
| Residual error | | | | | | | |
| RUV_PROP | $\Theta_1$ | Proportional error | % CV | 19.6 | 2.5 | | |
| RUV_ADD | $\Theta_2$ | Additive error | µg/L | 19.8 | 18.5 | | |

FIG. 15 presents the key diagnostic plots for the final model following the administration of Doryx MPC, Doryx tablet and Doryx capsules. The diagnostic plots appear consistent with an unbiased model.

The pcVPC of the final model provided a good description of the lower, median and higher doxycycline concentrations, as represented by a good overlay of the $5^{th}$, median and $95^{th}$ percentiles of the observed prediction-corrected concentrations over the empirical 95% CI's of the prediction-corrected doxycycline concentrations from 200 simulations of the index dataset (FIG. 16). The BLOQ VPC also indicates the final model provides a good description of doxycycline plasma concentrations BLOQ throughout time within the database, with the percentage of the observed data BLOQ throughout time overlaying well with the 95% CI of the percentage of BLOQ data from the 200 simulations of the original dataset (FIG. 17), indicating that the M1 method for handling BLOQ data was acceptable. Both the BLOQ VPC and pcVPC plots indicated that the structural, population and covariate components of the model provided a good description of the data following single- or multi-dose Doryx MPC, Doryx tablet or Doryx capsule under fed or fasted conditions, allowing for confidence in the subsequent simulations and power analyses.

8.12 Power Analysis

The final model indicated that Doryx MPC had a relative bioavailability of 0.863 and an absorption lag of 0.115 hours compared to a Doryx tablet for the studied population. In addition, the fed status reduced KTR by 54.9% for Doryx MPC and 20.9% for a Doryx tablet (plus the formulation non-specific 0.203 hour lag on absorption). Therefore, simulation and power analyses were used to interpret the chance of establishing bioequivalence between 120 mg of Doryx MPC compared to a reference 100 mg Doryx tablet in the fed and fasted states.

Plots of the median and 90% CI of doxycycline concentrations from 1000 simulated studies of 28 subjects were created (not presented), following the administration of the cross-over study designs indicated previously. Table 18 presents the percentage of the 1000 simulated studies displaying equivalent $AUC_{0t}$, $AUC_{inf}$, $C_{max}$ and $T_{max}$ for the cross-over studies including 12, 24, 28 and 36 subjects. Table 18 also presents the percentage of simulated studies deemed bioequivalent, which occurs when $AUC_{0t}$ and $C_{max}$ ($BE_{0t}$) or $AUC_{inf}$ and $C_{max}$ ($BE_{inf}$) were equivalent for a given study. For the studies which were deemed bioequivalent, Table 19 indicates the percentage of those that included 1 within the 90% CI of the ln-transformed test to reference ratio for $AUC_{0t}$ and $C_{max}$ or $AUC_{inf}$ and $C_{max}$.

The mean of the geometric mean, $10^{th}$ percentile and $90^{th}$ percentile for the ln-transformed test to reference ratios for $AUC_{0t}$, $AUC_{inf}$, $C_{max}$ and $T_{max}$, as calculated using an ANOVA analysis, was conducted following the simulation of 1000 replicate studies including 12, 24, 28 and 36 subjects. As expected, increasing the number of subjects within the studies was associated with a higher power for displaying bioequivalence. Table 18 indicates that for a study containing 36 subjects, the power of bioequivalence between 120 mg Doryx MPC and 100 mg Doryx tablet under fasted conditions was 100% when $BE_{0t}$ or $BE_{inf}$ were assessed respectively. For a study containing 28 subjects, the power of bioequivalence between 120 mg Doryx MPC and 100 mg Doryx tablet under fasted conditions was 99.6% and 99.5% when $BE_{0t}$ or $BE_{inf}$ were assessed respectively.

TABLE 18

Model Predicted Bioequivalence Results Calculated Using the ANOVA Method

| | Percent $AUC_{0t}$ | Percent $AUC_{inf}$ | Percent $C_{max}$ | Percent $T_{max}$ | Percent $BE_{0t}$ | Percent $BE_{inf}$ |
|---|---|---|---|---|---|---|
| 12 Participants Per Study (1000 simulated studies) | | | | | | |
| 120 mg Doryx MPC vs 100 mg Doryx (Fasted) | 89.8 | 87.9 | 88.1 | 15.7 | 79.2 | 77.8 |
| 120 mg Doryx MPC vs 100 mg Doryx (Fed) | 90.5 | 86.7 | 7.5 | 0 | 6 | 5.6 |
| 120 mg Doryx MPC vs 120 mg Doryx MPC (Fed/Fasted) | 62.4 | 60.5 | 0 | 0 | 0 | 0 |
| 100 mg Doryx vs 100 mg Doryx (Fed/Fasted) | 65.2 | 61.1 | 12.2 | 5 | 8.6 | 8.1 |
| 24 Participants Per Study (1000 simulated studies) | | | | | | |
| 120 mg Doryx MPC vs 100 mg Doryx (Fasted) | 99.7 | 99.6 | 99.8 | 58.6 | 99.5 | 99.4 |
| 120 mg Doryx MPC vs 100 mg Doryx (Fed) | 99.6 | 99.5 | 7.6 | 0 | 7.4 | 7.3 |
| 120 mg Doryx MPC vs 120 mg Doryx MPC (Fed/Fasted) | 88 | 85.9 | 0 | 0 | 0 | 0 |
| 100 mg Doryx vs 100 mg Doryx (Fed/Fasted) | 88.4 | 86 | 18.4 | 6.3 | 16.8 | 16.3 |
| 28 Participants Per Study (1000 simulated studies) | | | | | | |
| 120 mg Doryx MPC vs 100 mg Doryx (Fasted) | 99.8 | 99.7 | 99.8 | 67.4 | 99.6 | 99.5 |
| 120 mg Doryx MPC vs 100 mg Doryx (Fed) | 99.8 | 99.6 | 8.9 | 0 | 8.8 | 8.7 |
| 120 mg Doryx MPC vs 120 mg Doryx MPC (Fed/Fasted) | 92 | 90.6 | 0 | 0 | 0 | 0 |
| 100 mg Doryx vs 100 mg Doryx (Fed/Fasted) | 93.6 | 91.2 | 19 | 4.7 | 17.8 | 17.7 |

TABLE 18-continued

Model Predicted Bioequivalence Results
Calculated Using the ANOVA Method

| | Percent $AUC_{0t}$ | Percent $AUC_{inf}$ | Percent $C_{max}$ | Percent $T_{max}$ | Percent $BE_{0t}$ | Percent $BE_{inf}$ |
|---|---|---|---|---|---|---|
| 36 Participants Per Study (1000 simulated studies) | | | | | | |
| 120 mg Doryx MPC vs 100 mg Doryx (Fasted) | 100 | 100 | 100 | 82 | 100 | 100 |
| 120 mg Doryx MPC vs 100 mg Doryx (Fed) | 100 | 100 | 9.1 | 0 | 9.1 | 9.1 |
| 120 mg Doryx MPC vs 120 mg Doryx MPC (Fed/Fasted) | 95.8 | 95.1 | 0 | 0 | 0 | 0 |
| 100 mg Doryx vs 100 mg Doryx (Fed/Fasted) | 96.4 | 95.3 | 21.2 | 5.8 | 20.8 | 20.7 |

Percent $AUC_{inf}$, $AUC_{0t}$, $C_{max}$ and $T_{max}$, respectively, indicates the power percentage for a study to display equivalence of $AUC_{inf}$, $AUC_{0t}$, $C_{max}$, and $T_{max}$, for the cross-over designs indicated. Percent $BE_{0t}$ and $BE_{inf}$, respectively, indicates the power percentage for a study to display bioequivalence via either $AUC_{0t}$ and $C_{max}$ or $AUC_{inf}$ and $C_{max}$, for the cross-over designs indicated.

TABLE 19

$BE_{0t}$ and $BE_{inf}$ Studies That Included 1 with the 90% CI of ln-transformed Test to Reference Ratio for $AUC_{0t}$, $AUC_{inf}$ and $C_{max}$

| | Number of $BE_{0t}$ studies from the 1000 simulated replicates | % of $BE_{0t}$ studies that included 1 within the 90% CI of the test to reference ratio for $AUC_{0t}$ and $C_{max}$ | Number of $BE_{inf}$ studies from the 1000 simulated replicates | % of $BE_{inf}$ studies that included 1 within the 90% CI of the test to reference ratio for $AUC_{inf}$ and $C_{max}$ |
|---|---|---|---|---|
| 12 Participants Per Study (1000 simulated studies) | | | | |
| 120 mg Doryx MPC vs 100 mg Doryx (Fasted) | 792 | 84.85 | 778 | 85.35 |
| 120 mg Doryx MPC vs 100 mg Doryx (Fed) | 60 | 56.67 | 56 | 51.79 |
| 120 mg Doryx MPC vs 120 mg Doryx MPC (Fed/Fasted) | 0 | . | 0 | . |
| 100 mg Doryx vs 100 mg Doryx (Fed/Fasted) | 86 | 44.19 | 81 | 43.21 |
| 24 Participants Per Study (1000 simulated studies) | | | | |
| 120 mg Doryx MPC vs 100 mg Doryx (Fasted) | 995 | 64.02 | 994 | 65.59 |
| 120 mg Doryx MPC vs 100 mg Doryx (Fed) | 74 | 4.05 | 73 | 4.11 |
| 120 mg Doryx MPC vs 120 mg Doryx MPC (Fed/Fasted) | 0 | . | 0 | . |
| 100 mg Doryx vs 100 mg Doryx (Fed/Fasted) | 168 | 4.17 | 163 | 4.91 |
| 28 Participants Per Study (1000 simulated studies) | | | | |
| 120 mg Doryx MPC vs 100 mg Doryx (Fasted) | 996 | 60.84 | 995 | 61.91 |
| 120 mg Doryx MPC vs 100 mg Doryx (Fed) | 88 | 3.41 | 87 | 4.60 |
| 120 mg Doryx MPC vs 120 mg Doryx MPC (Fed/Fasted) | 0 | . | 0 | . |
| 100 mg Doryx vs 100 mg Doryx (Fed/Fasted) | 178 | 1.12 | 177 | 1.13 |

TABLE 19-continued $BE_{0t}$ and $BE_{inf}$ Studies That Included 1 with the 90% CI of ln-transformed
Test to Reference Ratio for $AUC_{0t}$, $AUC_{inf}$ and $C_{max}$

| | Number of $BE_{0t}$ studies from the 1000 simulated replicates | % of $BE_{0t}$ studies that included 1 within the 90% CI of the test to reference ratio for $AUC_{0t}$ and $C_{max}$ | Number of $BE_{inf}$ studies from the 1000 simulated replicates | % of $BE_{inf}$ studies that included 1 within the 90% CI of the test to reference ratio for $AUC_{inf}$ and $C_{max}$ |
|---|---|---|---|---|
| 36 Participants Per Study (1000 simulated studies) | | | | |
| 120 mg Doryx MPC vs 100 mg Doryx (Fasted) | 1000 | 55.10 | 1000 | 57.50 |
| 120 mg Doryx MPC vs 100 mg Doryx (Fed) | 91 | 1.10 | 91 | 1.10 |
| 120 mg Doryx MPC vs 120 mg Doryx MPC (Fed/Fasted) | 0 | . | 0 | . |
| 100 mg Doryx vs 100 mg Doryx (Fed/Fasted) | 208 | 0 | 207 | 0 |

$BE_{0t}$ indicates studies that were equivalent for both $AUC_{0t}$ and $C_{max}$. $BE_{inf}$ indicates studies that were equivalent for both $AUC_{inf}$ and $C_{max}$.

The power analysis was also used to assess the effect of food on equivalence power. Indicating for a study containing 28 subjects, the power of bioequivalence between 120 mg Doryx MPC and 100 mg Doryx tablet under fed conditions was 8.8% and 8.7% when $BE_{0t}$ or $BE_{inf}$ were assessed, respectively; which is in stark contrast to the results in the fasted state. Despite this, for a study containing 28 individuals the equivalence power for $AUC_{0t}$ and $AUC_{inf}$ when 120 mg Doryx MPC compared to a 100 mg Doryx tablet under fed conditions was 99.8% and 99.6%, respectively; this is comparable to the results in the fasted state where the equivalence power was 99.8% and 99.7%, respectively. Furthermore in a study containing 28 subjects for the cross-over design of 120 mg Doryx MPC under fasted/fed conditions, the power of equivalence for $AUC_{0t}$, $AUC_{inf}$ and $C_{max}$ was 92%, 90.6% and 0% respectively. This was similar to a study containing 28 subjects for the cross-over design of 100 mg Doryx tablet under fasted/fed conditions, where the power of equivalence for $AUC_{0t}$, $AUC_{inf}$ and $C_{max}$ was 93.6%, 91.2% and 19% respectively.

8.13 Discussion

A population pharmacokinetic model was developed to describe doxycycline plasma concentrations following a single dose of Doryx MPC or single/multiple doses of Doryx tablets or capsules, using data from eight healthy human pharmacokinetic trials. Of particular interest was capturing any bioavailability and absorption profile differences between the Doryx MPC and Doryx tablet formulations, as well as quantitating the effect of food on the two formulations.

To our knowledge, this is the first population pharmacokinetic analysis of doxycycline plasma concentrations following oral doxycycline dosing. Previously Beringer et al[6] performed a compartmental pharmacokinetic analysis in 20 cystic fibrosis adults dosed with multiple 40 mg, 100 mg or 200 mg doses of oral doxycycline (formulation unspecified), and found a two-compartment model with a lag on first-order absorption to best describe the plasma concentration-time data. Similar results were found here, albeit the present study is a population analyses based on extensive single- and multi-dose oral data, and a two-transit absorption compartment model performed considerably better than a delay (lag) on simple first-order absorption.

In the literature, there is little data on dose-linearity or the effect of multiple doses on doxycycline pharmacokinetics [2]. In the Beringer et al [6] study non-compartmental pharmacokinetic analysis indicated a less than dose-proportional relationship may be present in a small cystic fibrosis population dosed with multiple 40 mg, 100 mg or 200 mg doses of oral doxycycline. The mean exponents values of the power model used to determine dose non-proportionality were 0.75 and 0.74 for $C_{max}$ and $AUC_{inf}$, respectively. However, the 95% CI of the exponents did not support dose non-proportionality as they included 1, suggesting that dose proportionality could not be excluded. Dose-proportionality of pharmacokinetics was supported in this population analyses as demonstrated by the non-significance of dose effects on RELF, KTR and CL that were assessed in the covariate screening stage of this large population analysis. Given the diagnostic plots of the base and final models were consistent with an unbiased model and the pcVPC's showed a good description of the lower, median and higher doxycycline concentrations following single- or multi-dose Doryx MPC, Doryx tablet or Doryx capsule under fed or fasted conditions, it was considered that the structural and population components of the model appropriately represented the data, support dose-linearity and allowed for confidence in the subsequent power analyses.

In this study, an ANOVA analysis was implemented to calculate the 90% CI of the ln-transformed data [29,30]. ANOVA analyses can account for varying standard deviations within the ln-transformed $AUC_{inf}$, $AUC_{0t}$, $C_{max}$ or $T_{max}$ values of the test and reference formulations, and can account for period and sequence effects which are encouraged by regulatory authorities [35]. Increasing the number of subjects within a given bioequivalence study evidently increased the power of the study and tightened the CI of the ln-transformed test to reference ratios of each exposure metric. The results of the power analysis also support the bioequivalence of a 120 mg dose of Doryx MPC and a 100 mg Doryx tablet in the fasted state. This is reflected by the bioequivalence power being 99.6% and 99.5%, when $BE_{0t}$ or $BE_1$ are assessed respectively for a study of 28 participants. Of these studies deemed bioequivalent, the percentage that included 1 (the value of no difference) within the 90% CI of the ln-transformed test to reference ratio for both $AUC_{0t}$ and $C_{max}$ or $AUC_{inf}$ and $C_{max}$ was 60.8% and 61.9%, respectively. This is of interest as it may highlight a potential flaw with current bioequivalence guidelines, and may support the value of updating guidelines to include a value of no difference within the 90% CI, as has been discussed previously [36]. In the fed state for a study containing 28 subjects, the bioequivalence power between 120 mg Doryx MPC and a 100 mg Doryx tablet was 8.8% and 8.7% when $BE_{0t}$ or $BE_{inf}$ were assessed, respectively; this is in stark contrast to the results in the fasted state. Nonetheless, for a study containing 28 individuals the equivalence power for $AUC_{0t}$ and $AUC_{inf}$ when 120 mg Doryx MPC is compared to a 100 mg Doryx tablet under fed conditions was 99.8% and 99.6%, respectively; this is comparable to the results in the fasted state where the equivalence power was 99.8% and 99.7%, respectively. Therefore changes to the power of bioequivalence between the two formulations in the fed state, are the result of differences in the equivalence of $C_{max}$. Clinically this is unlikely to be of importance as previous studies have indicated that the AUC/MIC ratio is the key to doxycycline efficacy. See "Antimicrobial Pharmacodynamics in Theory and Clinical Practice," Second Edition. Edited by Charles H. Nightingale, Paul G. Ambrose, George L. Drusano and Takeo Murakawa. CRC Press 2007. Pages 267-277.

The final model included a lag on the start of absorption for the Doryx MPC formulation (and the Doryx capsule) comparative to the Doryx tablet formulation (ALAG=0.115), consistent with the Doryx MPC formulation being developed to reduce the release of doxycycline within the oesophagus and stomach, thus delaying the start of dissolution. Furthermore, the final model indicated the relative bioavailability of Doryx MPC was 86.3% of a Doryx tablet. This is consistent with Mayne Pharma International's hypothesis that the altered acid release profile of the Doryx MPC formulation would result in a reduction of the relative bioavailability of the formulation. The relative bioavailability of a Doryx capsule was indicated to be 97.8% of a Doryx tablet, which is consistent with the two formulations having very little difference in bioavailability. Furthermore, the final model included a lag on absorption for the fed status (FTLAG2=0.203 h). The fed status also resulted in formulation dependent differences in the absorption KTR parameter, where KTR decreased by 20.9% in the fed status for the Doryx tablet and Doryx capsule formulations, and decreased by 54.9% for the Doryx MPC formulation. Lowering the KTR parameter also has the effect of adding a further delay to doxycycline reaching systemic circulation, due to the increased time taken for the drug to move through the absorption transit compartments. The larger decrease in KTR for the Doryx MPC formulation over the Doryx tablet in the fed status is not surprising given the fed status will likely increase the transit time of the formulation within the stomach, effectively increasing the time until Doryx MPC dissolution will begin and thus reach systemic circulation. Irrespective of formulation the fed status was observed to decrease relative bioavailability by 10.5%, during the covariate assessment stage.

During the covariate assessment stage, the female sex was observed to increase doxycycline clearance by 14.4%. Although the clinical significance of this result is unknown, this sex effect has not been identified previously [2,3]. Previously, the impact of age on the pharmacokinetics of doxycycline was investigated in 25 elderly patients (over the age of 65), with findings indicating that concentrations were higher than those of a younger age [37]. In this study, age was not observed to influence doxycycline pharmacokinetics; however, the involvement of older individuals in this study was limited. The literature also indicated a minimal impact of renal function on doxycycline pharmacokinetics [2], albeit this was not assessed in this study as all participants were required to have normal renal function.

The analysis presented here is the first to explore a population pharmacokinetic model of doxycycline concentrations following oral administration, which is an important step towards a population pharmacokinetic-pharmacodynamic model that could be used to critically examine and optimize doxycycline dose regimens. Although in vitro studies indicate that low concentrations of doxycycline kill in a time-dependent kinetic manner, while higher concentrations kill in a concentration-dependent kinetic manner [38], at present this area has been insufficiently explored [2]. Albeit this study is a step towards this, it is of note that this study presents a population pharmacokinetic model of doxycycline concentrations following the oral administration of doxycycline concentrations in healthy individuals, and the effect of disease status or sickness on doxycycline pharmacokinetics was not investigated here as all participants were healthy volunteers.

In conclusion, a population pharmacokinetic model was developed to describe doxycycline plasma concentrations following a single dose of Doryx MPC or single/multiple doses of Doryx tablets or capsules in the fasted/fed states. Using the developed model, the power of establishing bioequivalence between a 100 mg Doryx tablet and the newly developed 120 mg Doryx MPC formulation was assessed, in the fed or fasted state. The power analysis indicated the fed/fasted state had minimal effect on the high likelihood of $AUC_{inf}$ and $AUC_{0t}$ equivalence between 120 mg of Doryx MPC and a 100 mg Doryx tablet. However, given the delayed release of the Doryx MPC formulation within the oesophagus and stomach, it was not surprising that the power of $C_{max}$ equivalence was low between 120 mg of Doryx MPC and a 100 mg Doryx tablet in the fed condition, which was not comparable to the results under fasted condition.

REFERENCES CITED

1. Holmes N E, Charles P G P (2009) Safety and Efficacy Review of Doxycycline. Clinical Medicine Therapeutics 1:471
2. Agwuh K N, MacGowan A (2006) Pharmacokinetics and pharmacodynamics of the tetracyclines including glycylcyclines. J Antimicrob Chemother 58 (2):256-265. doi: 10.1093/j ac/dkl224
3. Saivin S, Houin G (1988) Clinical Pharmacokinetics of Doxycycline and Minocycline. Clin Pharmacokinet 15 (6):355-366. doi:10.2165/00003088-198815060-00001
4. Australian Medicines Handbook Pty Ltd., Health Communication Network. (2014) Australian medicines handbook. Adelaide, S. Aust.; [Crows Nest, N.S.W.]
5. Mayne Pharma (2015) Drug Label Information: Doryx-doxycycline hyclate tablet, delayed release https://dailymed.nlm.nih.gov/dailymed/drugInfo.cfm?setid=99cf2de6-e0a3-42f2-9929-d33e107af948. Accessed Dec. 5, 2016 2016
6. Beringer P M, Owens H, Nguyen A, Benitez D, Rao A, D'Argenio D Z (2012) Pharmacokinetics of Doxycycline in Adults with Cystic Fibrosis. Antimicrob Agents Chemother 56 (1):70-74. doi:10.1128/aac.05710-11
7. European Medicines Agency (EMEA) (1996) Note for guidance on good clinical practice (CPMP/ICH/135/95); European Medicines Agency, London, United Kingdom.
8. World medical association declaration of helsinki: Recommendations guiding physicians in biomedical research involving human subjects (1997). JAMA 277 (11):925-926. doi:10.1001/jama.1997.03540350075038
9. Beal S, Sheiner L, Boeckmann A, Bauer R NONMEM 7.3. 0 Users Guides. (1989-2013). ICON Development Solutions, Hanover, Md.
10. Wickham H (2009) ggplot2: elegant graphics for data analysis. CRANR-projectorg; Springer New York
11. Højsgaard S, Halekoh U, Robison-Cox J, Wright K, Leidi A A (2014) doBy: doBy—Groupwise summary statistics, LSmeans, general linear contrasts, various utilities. CRAN.R-project.org,
12. Wickham H (2011) plyr—The Split-Apply-Combine Strategy for Data Analysis. Journal of Statistical Software 40 (1):1-29
13. Wickham H (2007) Reshaping Data with the {reshape} Package. Journal of Statistical Software 21 (12):1-20
14. Wickham H (2014) scales: Scale functions for graphics. CRAN.R-project.org,
15. Comets E, Brendel K, Nguyen T H T, Mentre F (2012) npde version 2.0. CRAN.R-project.org,
16. Wickham H (2012) stringr: Make it easier to work with strings. CRAN.R-project.org,
17. Auguie B (2012) gridExtra: functions in Grid graphics. CRAN.R-project.org,
18. Warnes G R, Bolker B, Gorjanc G, Grothendieck G, Korosec A, Lumley T, MacQueen D, Magnusson A, Rogers J (2015) gdata version 2.17.0. CRAN.R-project.org,
19. Harrell-Jr F E (2014) Hmisc: Harrell Miscellaneous. CRAN.R-project.org,
20. Wickham H (2016) tidyr version 0.4.1: Easily Tidy Data with spread 0 and gather ( ) Functions. CRANR-profectorg
21. R Core Team (2015) foreign version 0.8-66. CRANR-projectorg
22. Schloerke B, Crowley J, Cook D, Hofmann H, Wickham H (2014) GGally version 0.5.0; http://cran.r-project.org/web/packages/GGally/index.html.
23. Beal S L Ways to Fit a P K Model with Some Data Below the Quantification Limit. J Pharmacokinet Pharmacodyn 28 (5):481-504. doi:10.1023/a:1012299115260
24. Anderson B, Holford N (2008) Mechanism-based concepts of size and maturity in pharmacokinetics. Annu Rev Pharmacol Toxicol 48:303-332
25. Janmahasatian S, Duffull S B, Ash S, Ward L C, Byrne N M, Green B (2005) Quantification of lean bodyweight. Clin Pharmacokinet 44 (10): 1051-1065
26. Anderson B J, Holford N H (2009) Mechanistic basis of using body size and maturation to predict clearance in humans. Drug Metab Pharmacokinet 24 (1):25-36
27. Laporte-Simitsidis S, Girard P, Mismetti P, Chabaud S, Decousus H, Boissel J-P (2000) Inter-study variability in population pharmacokinetic meta-analysis: When and how to estimate it? J Pharm Sci 89 (2):155-167. doi: 10.1002/(sici)1520-6017(200002)89:2<155::aid-jps3>3.0.co; 2-2
28. Bergstrand M, Hooker A C, Wallin J E, Karlsson M O (2011) Prediction-Corrected Visual Predictive Checks for Diagnosing Nonlinear Mixed-Effects Models. The AAPS journal 13 (2):143-151. doi:10.1208/s12248-011-9255-z
29. Rani S, Pargal A (2004) Bioequivalence: An overview of statistical concepts. Indian Journal of Pharmacology 36 (4):209-216
30. John Gordon, Kemmler H (2006) WHO, Training workshop on pharmaceutical quality, good manufacturing practive and bioequivalence; Statistical considerations for bioequivalence studies.
31. R Core Team (2015) R: A language and environment for statistical computing. http://www.R-project.org/.
32. Wojciechowski J, Hopkins A M, Upton R N (2015) Interactive Pharmacometric Applications Using R and the Shiny Package. CPT: Pharmacometrics & Systems Pharmacology 4 (3):146-159. doi:10.1002/psp4.21
33. RStudio Inc (2015) shiny: Web Application Framework for R. R package version 0.10.1. http://CRAN.R-project.org/package=shiny.
34. Abuhelwa A Y, Foster D J, Upton R N (2015) ADVAN-style analytical solutions for common pharmacokinetic models. J Pharmacol Toxicol Methods 73:42-48
35. FDA (2001) Statistical approaches to establishing bioequivalence. Center for Drug Evaluation and Research; United States Department of Health and Human Services; Food and Drug Administration
36. Danish Medicines Agency (2012) Bioequivalence and labelling of medicines with regard to generic substitution. http://laegemiddelstyrelsen.dk/en/licensing/licensing-of-medicines/marketing-authorisation/application-for-marketing-authorisation/bioequivalence-and-labelling-of-medicines-with-regard-to- generic-substitution. Accessed 25 Jun. 2016
37. Wicker R, Mühlberg W, Platt D, Estler C-J (1986) Serum level, half-life and apparent volume of distribution of doxycycline in geriatric patients. Eur J Clin Pharmacol 30 (1):105-108. doi:10.1007/bf00614205
38. Cunha B A, Domenico P, Cunha C B (2000) Pharmacodynamics of doxycycline. Clin Microbiol Infect 6 (5): 270-273. doi:10.1046/j.1469-0691.2000.00058-2.x
39. The United States Pharmacopeia (USP) Standards, Published by the United States Pharmacopeial Convention, Inc., 12601 Twin Brook Parkway, Rockville, Md. 20852 USA (e.g. USP <711> Dissolution Standard)

In aspects of the present disclosure, the doxycycline dosage forms are expressed as an amount of doxycycline salt equivalent to achieve a stated amount of doxycycline base. For example, the disclosure provides various dosage forms comprising doxycycline salt that is present in an amount equivalent to 60, 90, or 120 mg of doxycycline base.

While this disclosure has been described with respect to various specific examples and embodiments, it is to be understood that the disclosure is not limited thereto and that it can be variously practiced within the scope of the recited claims.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A dosage form, comprising a plurality of modified release doxycycline salt pellets, wherein the doxycycline salt pellets comprise a doxycycline salt core and a controlled release polymer composition disposed over the core,
   wherein said controlled release polymer composition comprises a blend of hydroxypropyl methylcellulose phthalate and hydroxypropyl methyl cellulose;
   wherein said dosage form comprises doxycycline salt in an amount equivalent to 60, 90, or 120 mg of doxycycline base;
   wherein said dosage form comprising doxycycline salt maintains doxycycline base release levels measured under USP <711> conditions at pH 5 that provide a clinically effective plasma level of doxycycline base;

wherein said dosage form releases less than 15% of the doxycycline at pH 1.2 and less than 40% of the doxycycline at pH 4.5 after 60 minutes; and wherein after administration of a single dose under fasting conditions to a patient in need thereof, the average $AUC_{0-\infty}$ is 80% to 125% of 200-300 ng·hr/ml per mg of doxycycline base administered.

2. The dosage form of claim 1, wherein the average $AUC_{0-\infty}$ is 80% to 125% of 220-225 ng·hr/ml per mg of doxycycline base administered.

3. The dosage form of claim 1, wherein said dosage form comprises doxycycline salt in an amount equivalent to 60 mg of doxycycline base and after administration of a single dose under fasting conditions to a patient in need thereof, the average $AUC_{0-\infty}$ is 13345±1000 ng·hr/ml.

4. The dosage form of claim 1, wherein said dosage form comprises doxycycline salt in an amount equivalent to 120 mg of doxycycline base and after administration of a single dose under fasting conditions to a patient in need thereof, the average $AUC_{0-\infty}$ is 26690±1000 ng·hr/ml.

5. The dosage form of claim 1, wherein after administration of a single dose under fasting conditions to a patient in need thereof, the average $C_{max}$ is 80% to 125% of 10-20 ng/ml per mg of doxycycline base administered.

6. The dosage form of claim 5, wherein the average $C_{max}$ is 80% to 125% of 10-15 ng/ml per mg of doxycycline base administered.

7. The dosage form of claim 1, wherein said dosage form comprises doxycycline salt in an amount equivalent to 60 mg of doxycycline base and after administration of a single dose under fasting conditions to a patient in need thereof, the average $C_{max}$ is 809±100 ng/ml.

8. The dosage form of claim 1, wherein said dosage form comprises doxycycline salt in an amount equivalent to 120 mg of doxycycline base and after administration of a single dose under fasting conditions to a patient in need thereof, the average $C_{max}$ is 1619±100 ng/ml.

9. The dosage form of claim 1, wherein at pH 5 the normalized average release of doxycycline base measured under USP <711> conditions is at least one of:
less than 48% at 15 minutes;
less than 64% at 20 minutes; and
less than 72% at 25 minutes.

10. The dosage form of claim 1, wherein at pH 5 the normalized average release of doxycycline base measured under USP <711> conditions is at least one of:
30% to 48% at 15 minutes;
30% to 64% at 20 minutes; and
45% to 72% at 25 minutes.

11. The dosage form of claim 1, wherein at pH 5 the normalized average release of doxycycline base measured under USP <711> conditions is at least one of:
35% to 48% at 15 minutes;
40% to 64% at 20 minutes; and
50% to 72% at 25 minutes.

12. The dosage form of claim 1, wherein at pH 5 the normalized average release of doxycycline base measured under USP <711> conditions at 20 minutes ranges from 42% to 64%.

13. The dosage form of claim 1, wherein at pH 5 the normalized average release of doxycycline base measured under USP <711> conditions at 20 minutes ranges from 47% to 64%.

14. The dosage form of claim 1, wherein at pH 5 the normalized average release of doxycycline base measured under USP <711> conditions at 25 minutes ranges from 58% to 72%.

15. The dosage form of claim 1, wherein at pH 5 the normalized average release of doxycycline base measured under USP <711> conditions at 25 minutes ranges from 65% to 72%.

16. The dosage form of claim 1, wherein said doxycycline salt pellets are contained in a capsule or tablet.

17. The dosage form of claim 1, wherein the doxycycline salt is doxycycline hyclate.

18. The dosage form of claim 1, wherein the release of doxycycline base is measured under USP <711> conditions comprising: rotating the dosage form in a USP Apparatus 1 basket at 100 RPM, within 900 mL of a dissolution media comprising acid or buffer, which is held at a temperature of 37° C.

19. The dosage form of claim 18, wherein said dosage form is a tablet.

20. The dosage form of claim 1, wherein the release of doxycycline base is measured under USP <711> conditions comprising: rotating the dosage form in a USP Apparatus 1 basket at 50 RPM, within 900 mL of a dissolution media comprising acid or buffer, which is held at a temperature of 37° C.

21. The dosage form of claim 1, wherein the controlled release polymer composition further comprises a plasticizer.

22. The dosage form of claim 21, wherein the plasticizer is selected from the group consisting of citric acid esters, tartaric acid esters, glycerol, glycerol esters, phthalic acid esters, adipic acid esters, sebacic acid esters, polyethylene glycol esters, sorbitan esters, and combinations thereof.

23. The dosage form of claim 22, wherein the controlled release polymer composition consists essentially of hydroxypropyl methylcellulose phthalate, hydroxypropyl methyl cellulose, and triethylcitrate.

24. The dosage form of claim 1, wherein the ratio of hydroxypropyl methylcellulose phthalate to hydroxypropyl methylcellulose ranges from about 3.5:1 to about 6:1.

25. The dosage form of claim 1, wherein the ratio of hydroxypropyl methylcellulose phthalate to hydroxypropyl methylcellulose ranges from about 3.5:1 to about 6:1.

* * * * *